United States Patent
Morgenstern et al.

(10) Patent No.: US 6,489,118 B2
(45) Date of Patent: *Dec. 3, 2002

(54) ALLERGENIC PROTEINS AND PEPTIDES FROM DOG DANDER AND USES THEREFOR

(75) Inventors: Jay P. Morgenstern, Boston, MA (US); Christine B. Bizinkauskas, Marlborough, MA (US); Andrzej Konieczny, Arlington, MA (US); Andrew W. Brauer, Salem, MA (US)

(73) Assignee: ImmuLogic Pharmaceutical Corporation, Waltham, MA (US)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/374,671

(22) Filed: Aug. 16, 1999

(65) Prior Publication Data

US 2002/0012963 A1 Jan. 31, 2002

Related U.S. Application Data

(63) Continuation of application No. 08/491,861, filed on Oct. 27, 1995, now Pat. No. 5,939,283, which is a continuation of application No. PCT/US93/12468, filed on Dec. 30, 1993, which is a continuation-in-part of application No. 08/156,549, filed on Nov. 22, 1993, now abandoned, which is a continuation-in-part of application No. 07/999,712, filed on Dec. 31, 1992, now abandoned.

(51) Int. Cl.[7] .......................... G01N 33/53; A01N 37/18; A61K 38/00; C07K 14/00

(52) U.S. Cl. .............................. 435/7.1; 514/2; 514/12; 530/350

(58) Field of Search ................................ 536/23.5, 23.1; 435/69.1, 320.1, 325, 252.3, 7.1; 530/350; 514/2, 12; 424/184.1, 185.1, 275.1

(56) References Cited

U.S. PATENT DOCUMENTS 5,583,046 A * 12/1996 Valenta et al. ............ 435/320.1
5,891,716 A * 4/1999 Morgenstern et al. ...... 435/325

OTHER PUBLICATIONS

De Groot et al. (1991) "Affinity Purification of a Major and a Minor Allergen from Dog Extract: Serologic Activity of Affinity–Purified *Can f* I and of *Can f* I–Depleted Extract" *J. Allergy Clin. Immunol.* 87: 1056–1065.

Dybendal et al. (1989) "Dust from Carpeted and Smooth Floors" *Allergy* 44: 401–411.

Ford et al. (1989) "The Allergens of Dog I. Identification Using Crossed Radio–Immunoelectrophoresis" *Clin. Exp. Allergy* 19: 183–190.

Ford et al. (1992) "The Allergens of Dog II" *Clin. Exper. Allergy*, vol. 22: 793–803.

(List continued on next page.)

Primary Examiner—Karen Cochrane Carlson
Assistant Examiner—Rita Mitra
(74) Attorney, Agent, or Firm—Lahive & Cockfield, LLP

(57) ABSTRACT

Isolated nucleic acids encoding allergens of *Canis familiaris*, Canf I or Can f II, are disclosed. A cDNA encoding a peptide having a Can f I activity and a predicted molecular weight of about 19,200 daltons is also described. A cDNA encoding a peptide having Can f II activity and a predicted molecular weight of about 18,200 daltons is also disclosed. The nucleic acids can be used as probes to detect the presence of Can f I or Can f II nucleic acid in a sample or for the recombinant production of petides having a Can f I or Can f II activity. Peptides having a Can f I or Can f II activity can be used in compositions suitable for pharmaceutical administration or methods of diagnosing sensitivity to dog dander.

4 Claims, 38 Drawing Sheets

OTHER PUBLICATIONS

Griffith et al. (1992) "Expression and Genomic Structure of the Genes Encoding Fdl, The Major Allergen From the Domestic Cat" *Gene,* vol. 113:263–268.

Hedlin et al. (1991) "Immunotherapy with Cat—and Dog–Dander Extracts" *J. Alergy Clin. Immunol.* 87: 955–964.

Lowenstein et al. (1983) "Domestic Animal Allergens" *Proceedings 11th International Congress of Allergology and Clinical Immunology* (The Macmillan Press Ltd.) 545–548.

Redl et al. (1992) "cDNA Cloning and Sequencing Reveals Human Tear Prealbumin to be a Member of the Lipophilic–Ligand Carrier Protein Superfamily" *J. Biol. Chem.,* vol. 267: 20282–20287.

Schmale et al. (1990) "Possible Role for Salivary Gland Protein in Taste Reception Indicated by Homology to Lipophillic–Ligand Carrier Proteins" *Nature* 343: 366–369.

Schou et al. (1991) "Purification and Characterization of the Major Dog Allergen, Can f I" *Clin. and Exp. Allergy* 21: 321–328.

Simpson et al. (1984) "*In situ* Cyanogen Bromide Cleavage of N–Terminally Blocked Proteins in a Gas–Phase Sequencer" *Biochem. International* 8: 787–791.

Spitzauer et al. (1993) "Characterization of Dog Allergens by Means of Immunoblotting" *Int. Arch. Allergy Immunol.* 100: 60–67.

Taylor et al. (1978) "Immunotherapy in Cat–Induced Asthma" *J. Allergy. Clin. Immunol.* 61(5): 283–287.

Tizard (1988) *Immunotherapy: An Introduction* (Philadelphia, PA: Saunders College Publishing) $2^{nd}$ Ed.:18–26.

Uhlin et al. (1984) "Antigenic/Allergenic Composition of Poodle/Alsatian Dandruff Extract" *Allergy* 39: 125–133.

Vanto et al. (1983) "Dog Hypersensitivity in Asthmatic Children" *Acta Paediatr. Scand.,* 72: 571–575.

Wood et al. (1988) "Antigenic Analysis of Household Dust Samples" *Am. Rev. Respir. Dis.* 137: 358–363.

Yman et al. (1984) "Serum Albumin—An Important Allergen in Dog Epithelia Extracts" *Int. Arch. Allergy Appl. Immunol.* 44: 358–368.

\* cited by examiner

```
                                            W  Y  L  K  A  M  T
                                               c  c  a  g
                                         c
                              1A 5'-gggaattctggta tt  aa  atgac-3'
                                                  t  g  gc
                                                  c
                                EcoR I                t W  Y  L  K  A  M  T
                                               c  g  a  g
                                         c
                              1B 5'-gggaattctggta ct t  gc atgac-3'
                                                  t  a  g
                                                  c  c
                                EcoR I D  Q  E  V  P  E  K  P
                                     c  a  a  g  a  a  a
                                      a                          Dog Probe 1
                                5'-ga ca ga gt cctga aa cc-3'
                                   t     g  g  t  g
                                      c               g Y  I  L  Y  C  E  G
                                       a  a           g          Dog Probe 2
                                5'--tacattct ta tgtga gg-3'
                                          t              a
                                          c  c
                                          c M  I  L  K  A  Q  K  G
                            a     c  g  c     c                          2A
                                    c  a  c  c
                     3'tactataa tt cg gt tt cctagggg-5' AS
                                g  t  t  t
                                c M  I  L  K  A  Q  K  G
                            a     c  g  c     c                          2B
                                    c  a  c  c
                     3'tactatga tt cg gt tt cctagggg-5' AS
                                g  t  t  t
                                c                          BamH I Fig. 1A
```

```
         Y  Ia  L   Y   C   E   G
3' at a tataa c at a acact c cctagggg-5' AS    3A
       g     t  g         t BamH I
```

```
         Y  Ia  Lg  Y   C   E   G
3' at a tatga a at a acact c cctagggg-5' AS    3B
       g     t  g         t BamH I
             c
```

Fig 1B

```
              G  Q  R  V  V  F  I
XSD  5'-gggctcgaggccagcgtcgtgttcatc-3'
         Xho I Q  P  S  P  V  R  D
XSE  5'-gggctcgagcagccgtccccgtgagggac-3'
         Xho I Q   E   A   L   E   D   F
               a   a   g   g                t
5'-ca ga gc ctaga ga tt-3'  Dog Probe 4
       g  g    t  g  c
                  c ct              Bgl II
                                         agctctagagggg-5' JM3-3XB
                                     agXho I
3'-acgtcgccggcgtcgaaggag
3'-acgtcgccggcgtcgcggcgtcgaaggatcactcagcataagc-5' JM3-1
                          3'-ggatatcactcagcataagc-5' JM3
3'-acgtcgccggcgtcgaaggaggatcc-5' JM3-3Bam
                            BamH I
```

Fig. 2A

```
                Y  Ia  L   Y  C   E   G
         3' at a tataa c at a acact c cctagggg-5'    AS  3A
               g       t g         t BamH I
               g                   g Y  Ia  L g Y  C   E   G
         3' at a tatga a at a acact c cctagggg-5'    AS  3B
               g       t g         t BamH I
               g                   g
                       c
```

```
              10         20         30         40         50         60
     ATGAAGACCCTGCTCCTCACCATCGGCTTCAGCCTTCATTGCGATCCTGCAGGCCCAGGAT
     -26                                                  -10
      M  K  T  L  L  L  T  I  G  F  S  L  I  A  I  L  Q  A  Q  D 70         80         90        100        110        120
     ACCCCAGCCTTGGGAAAGGACACTGTGGCTGTGTCAGGGAAATGGTATCTGAAGGCCATG
                        1                               10
      T  P  A  L  G  K  D  T  V  A  V  S  G  K  W  Y  L  K  A  M 130        140        150        160        170        180
     ACAGCAGACCAGGAGGTGCCTGAGAAGCCTGACTCCGTCAGTCACTCCCATGATCCTCAAAGCC
                  20                              30
      T  A  D  Q  E  V  P  E  K  P  D  S  V  T  P  M  I  L  K  A 190        200        210        220        230        240
     CAGAAGGGGGGCAACCTGGAAGCCAAGATCACCATGCTGACAAATGGTCAGTGCCAGAAC
                    40                             50
      Q  K  G  G  N  L  E  A  K  I  T  M  L  T  N  G  Q  C  Q  N 250        260        270        280        290        300
     ATCACGGTGGTCCTGCACAAAACCTCTGAGCCTGGCAAATACACGGCATACGAGGGCCAG
                                   60                          70
      I  T  V  V  L  H  K  T  S  E  P  G  K  Y  T  A  Y  E  G  Q
```

Fig. 5A

```
      310        320        330        340        350        360
CGTGTCGTGTTCATCCAGCCGTCCCCGGTGAGGACCACTACATTCTCTACTGCGAGGGC
                                      80                    90
 R   V   V   F   I   Q   P   S   P   V   R   D   H   Y   I   L   Y   C   E   G 370        380        390        400        410        420
GAGCTCCATGGAGGCAGATCCGAATGGCCAAGCTTCTGGGAAGGATCCTGAGCAGAGC
                      100                            110
 E   L   H   G   R   Q   I   R   M   A   K   L   L   G   R   D   P   E   Q   S 430        440        450        460        470        480
CAAGAGGCCTTGGAGGATTTTCGGGAATTCTCAAGAGCCAAAGGATTGAACCAGGAGATT
                              120                            130
 Q   E   A   L   E   D   F   R   E   F   S   R   A   K   G   L   N   Q   E   I 490        500        510        520
TTGGAACTCGCGCAGAGCGAAACCTGCTCTCCAGGAGGACAGTAG
                      140
 L   E   L   A   Q   S   E   T   C   S   P   G   G   Q   -
```

Fig. 5B

SETTING OF COMPUTATION PARAMETERS

K-TUPLE VALUE : 1
GAP PENALTY : 30
WINDOW SIZE : 5
FILTERING LEVEL: 2.5
OPEN GAP COST : 25
UNIT GAP COST : 25

SETTING OF OTHER PARAMETERS

THE ALIGNMENT WAS DONE ON 3 PROTEIN SEQUENCES.
CHARACTER TO SHOW THAT A POSITION IN THE ALIGNMENT IS PERFECTLY CONSERVED: '*'
CHARACTER TO SHOW THAT A POSITION IS WELL CONSERVED: '.'

ALIGNMENT

```
CANF1    DTVAVSGKWYLKAMTADQEVPEKPDSVTPMILKAQKGGNLEAKITMLTNG            50
2CANF1   DTVAVSGKWYLKAMTADQEVPEKPDSVTPMILKAQKGGNLEAKITMLTNG            50
3CANF1   --------------------PEKPDSVTPMILKAQKGGNLEAKITMLTNG            30
                             *******************************

CANF1    QCQNITVVLHKTSEPGKYTAYEGQRVVFIQPSPVRDRYILYCEGDLLPQA            100
2CANF1   QCQNITVVLHKTSEPGKYTAYEGQRVVFIQPSPVRDHYILYCEGELHGR-            99
3CANF1   QCQNITVVLHKTSEPGKYTAYEGQRVVFIQPSPVRDHYILYCEGELHGRQ            80
         *********************************.********.  .

CANF1    HLLHPSCHHHSLLQAHHRLLLPHKKLLQGDPCVAQWFSACLGLRA                 145
2CANF1   QIRMAKLLGRDPEQAHHRLLLPHKKLLQGDPCVAQWFSACLGLRA                 144
3CANF1   IRMAKGLNQEILELAQS-----------------------ETCSPGGQ             105
          *                                           .
```

CONSENSUS LENGTH: 145
IDENTITY : 76 (52.4%)
SIMILARITY: 7 (4.8%)

Fig. 9

```
AP2     5' GGG TCT AGA GGT ACC GTC CG 3'

AT/AL:  5' GGG TCT AGA GGT ACC GTC CGA TCG ATC ATT 3'
                                    TAGC TAG TAAp 5'
                                          G
                                          C
                                      3'- T

APA     5'-GGG CTC GAG GTC GAG TTT TTT TTT TTT TTT TT (GAC)

D2-1:   5'-GGGGGATCC CAG ATC GGA CTT ATT GGA GGC-3'

D2-2:   5'-GGGGGATCC GGA GGC CAG GGC AAC GGA-2'

D2-3:   5'-GGGGGATCC AAC GGA GTG CCA CCT CCC-3'

D2-4:   5'-GGGGGAATTC GAG GAG CTG TCT GGG AGG TGG-3'

D2-5:   5'-GGGGGAATTC AGG TGG CAC TCC GTT GCC CTG-3'

D2-6:   5'-GGGGGAATTC GCC CTG GCC TCC AAC AAG TCC-3'

D2-9:   5'-GGGGGAATTC GAG GGA AAC CAT GAG GAG CC-3'

D2-11:5'-GGA CTT GTT GGA GGC CAG GGC-3'

D2-12:5'-GGGGGAATTC ATC AAA CCC TGG GGG CAC TT-3'

D2-13:5'-GGGGGGATCC AA GTG CCC CCA GGG TTT GAT-3'

D2-17:5'-CAC GGG GAT ATC CTT ATA CC-3'

D2-19:5'-G TAC AAC GAT GAC ACC AG-3'

D2-20:5'-TGT CCC CCG AGC CTA T-3'

D2-23:5'-TC CTA CTG CTG ACC GTG G-3'
```

Fig. 16

```
                                                              AGAGCTGGACCCGT    15
GTGTGTGCTGGCCAATGAGCCCTGGAGGGTCCGGCTCCAGAGTACCCTCTTGGCACAGGG    75
CCGAGTCCATGGGACAGATGAACTAGAGGACTCCATCGCTCCCACTGCCACGGGGCCG   135
GGTCACCAGACTCTGCAAGTCTCCAGCTGTCGCCAAACAGACAGAAGGTGCTGTGGAC   195

ATGCAGCTCCTACTGCTGACCGTGGGCCTGGCACTGATCTGTGGCCTCCAGGCTCAGGAG   255
 M  Q  L  L  L  L  T  V  G  L  A  L  I  C  G  L  Q  A  Q  E    1
-19                                  -10

GGAAACCATGAGGAGCCCCAGGAGGCCTAGAGAGGCCTAGAGGAGCTGTCTGGGAGTGGCACTCCGTT   315
 G  N  H  E  E  P  Q  E  A  *  E  G  L  E  E  L  S  G  R  W  H  S  V
                           10                              20

GCCCTGGCCTCCAACAAGTCCGATCTGATCAAACCCTGGGGCCACTTCAGGTTTCATC   375
 A  L  A  S  N  K  S  D  L  I  K  P  W  G  H  F  R  V  F  I
                  30                              40

CACAGCATGAGCGCAAAGGACGGCAACCTGCACGGGGATATCCTTATACCGCAGGACGGC   435
 H  S  M  S  A  K  D  G  N  L  H  G  D  I  L  I  P  Q  D  G
                  50                              60
```

Fig. 18A

```
CAGTGCGAGAAAGTCTCCCTCACTGCCGTTCAAGACTGCCACCAGCAACAAATTTGACCTG  495
 Q  C  E  K  V  S  L  T  A  F  K  T  A  T  S  N  K  F  D  L
                            70                            80

GAGTACTGGGGACACAATGACCTGTACCTGGCAGAGGTAGACCCCAAGAGCTACCTGATT  555
 E  Y  W  G  H  N  D  L  Y  L  A  E  V  D  P  K  S  Y  L  I
                            90                           100

CTCTACATGATCAACCAGTACAACGATGACACCAGCCTGGTGGCTCACTTGATGGTCCGG  615
 L  Y  M  I  N  Q  Y  N  D  D  T  S  L  V  A  H  L  M  V  R
                           110                           120

GACCTCAGCAGGCAGCAGGACTTCCTGCCGGCATTCGAATCTGTATGTGAAGACATCGGT  675
 D  L  S  R  Q  Q  D  F  L  P  A  F  E  S  V  C  E  D  I  G
                           130                           140

CTGCACAAGGACCAGATTGTGGTTCTGAGCGATGACGATCGCTGCCAGGGTTCCAGAGAC  735
 L  H  K  D  Q  I  V  V  L  S  D  D  D  R  C  Q  G  S  R  D
                           150                           160

TAGGGCCTCAGCCACGCCAAGCAGCAGGATCTCACCTGCCTGAGTACGGT            792
 *

Fig. 18B
``` rCanf2 VS NATIVE FORMATTED ALIGNMENT

```
rCanf2        MQLLLLTVGL ALICGLQAQE GNHEEPQGGL EELSGRWHSV ALASNKSDLI    50
CANF2 NATIVE  ---------- ---------E GNHEEPQGGL EELSGRWHSV ALASXKSDLI    31 rCanf2        KPWGHFRVFI HSMSAKDGNL HGDILIPQDG QCEKVSLTAF KTATSNKFDL   100
CANF2 NATIVE  XPWGHFR--- ---------- ---------- ---------- ----------    38 rCanf2        EYWGHNDLYL AEVDPKSYLI LYMINQYNDD TSLVAHLMVR DLSRQQDFLP   150
CANF2 NATIVE  ---------- ---------- ---------- ---------- ----------    38 rCanf2        AFESVCEDIG LHKDQIVVLS DDDRCQGSRD                         180
CANF2 NATIVE  ---------- ---------- ----------                          38
```

Fig. 19

UNTITLED-2 FORMATTED ALIGNMENT

```
Canf 2      MQ--LLLLTV GLALICGLQA QEGNHEEPQG GLEELSGRWH SVALASNKSD    48
RAT A2U     MKLLLLLLCL GLIILVC-GHA EEANSERGNL DVDKLNGDWF SIVVASNKRE   49
MUP6_MOUSE  MK-MLLLLCL GLIILVC-VHA EEASSTGRNF NVEKINGEWH TIILASDKRE   48

Canf 2      LIKPWGHFRV FIHSMSAKDG NLHGDILIPQ DGQCEKVSLT AFKTATSNKF    98
RAT A2U     KIEENGSMRV FMQHIDVLEN SLGFKLCIKE NGECRKLYSV AYKTPKIGEY    99
MUP6_MOUSE  KIEDNGNFRL FLEQIHVLEN SLVLKFHTVR DEECSELSMV ADKTEKAGEY    98

Canf 2      DLEYWGHNDL YLAEVDPKSY LILYMINQYN DDTSLVAHLM VRDLSRQQDF   148
RAT A2U     FLEYDGGNTF TILKTDYERY VMFHLVNVNN GEAFQLMELY GRTKDLSSDI   149
MUP6_MOUSE  SVTYDGFNTF TIPKTDYDNF LMAHLINEKD GETFQLMGLY GREPDLMSDI   148

Canf 2      LPAFESVCED IGLHKDQTVV LSDDDRCQGS RD                      180
RAT A2U     KEKFAKLCEA HGITRDNIID LTKTDRCLQA RG                      181
MUP_6 MOUSE KERFAQLCEE HGILRENIID LSNANRCLQA RE                     180
```

Fig. 21

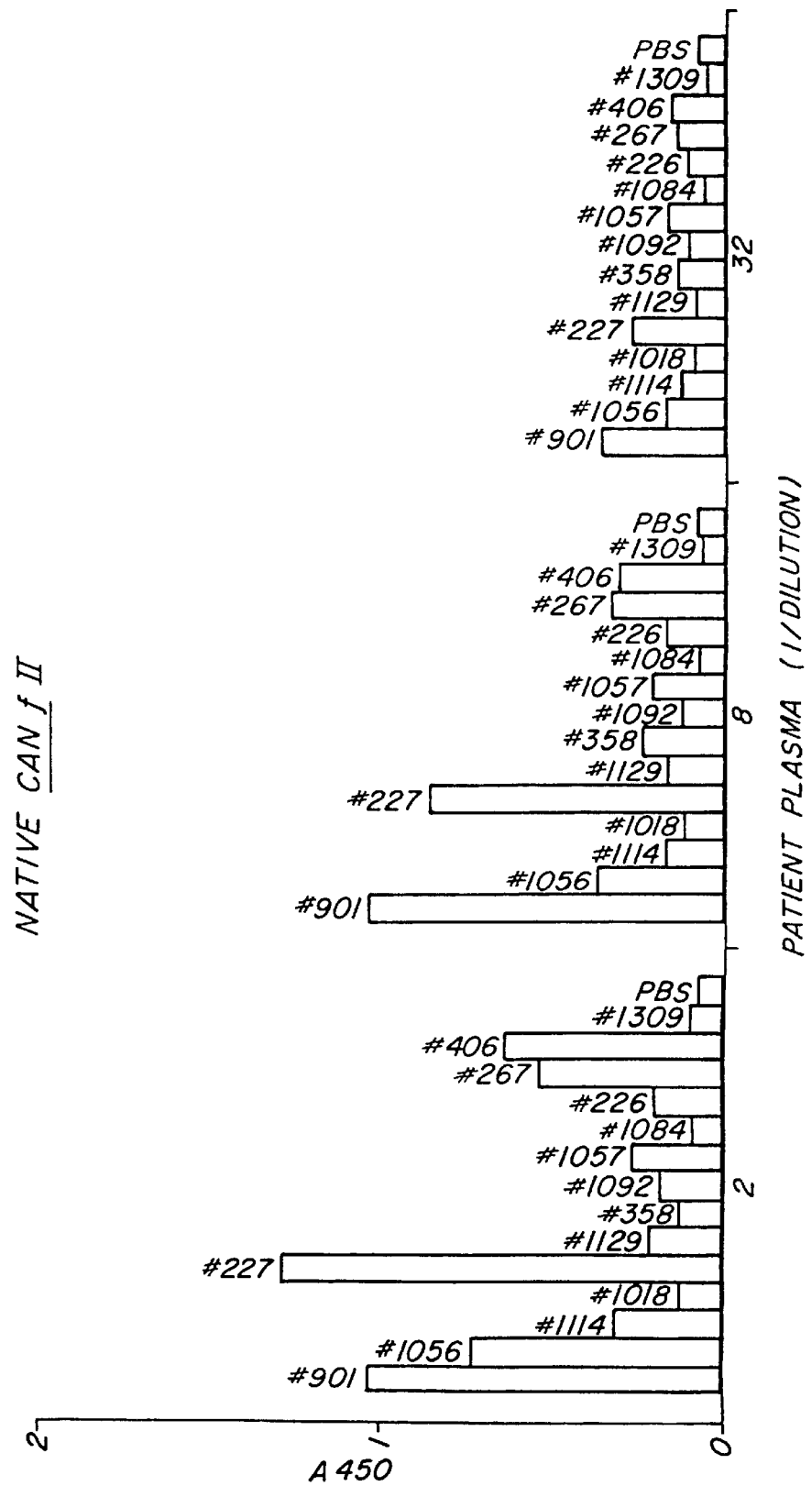
Fig. 22A (PART 1)

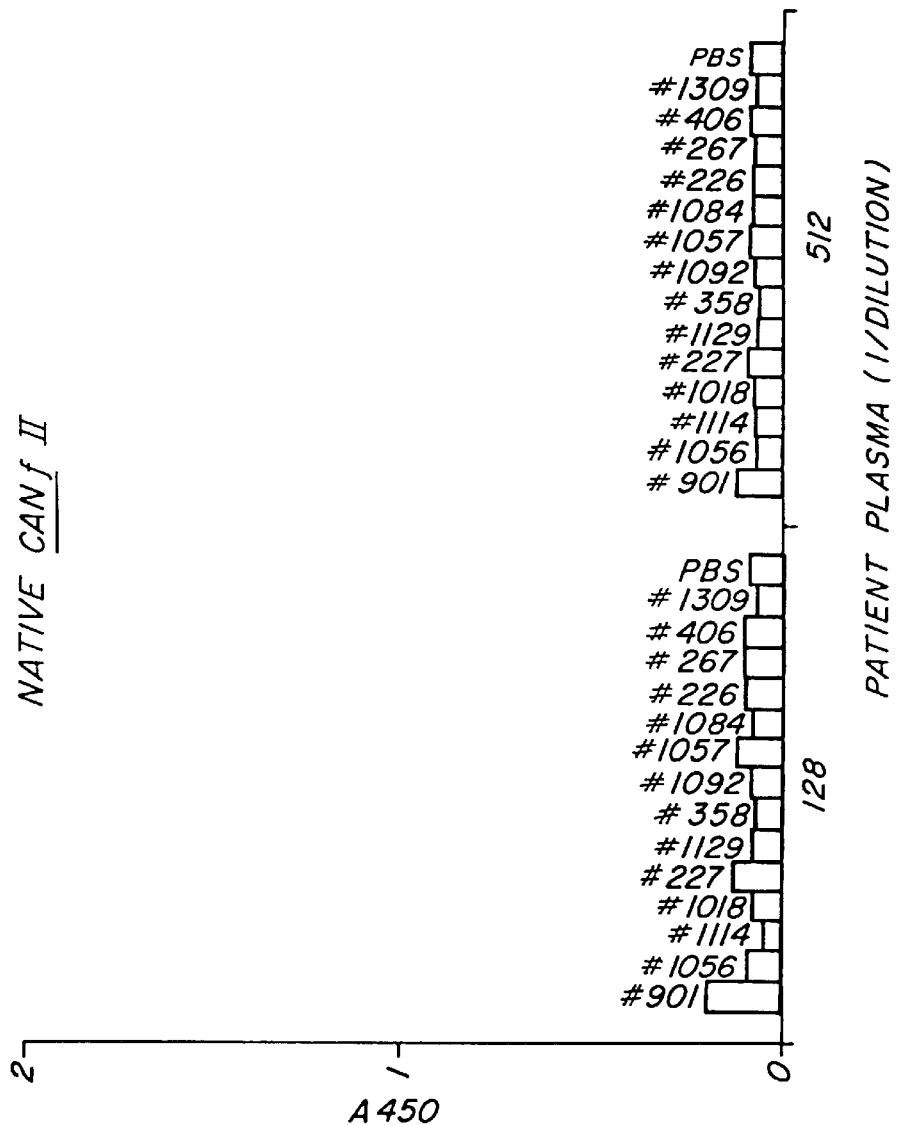
Fig. 22A (PART 2)

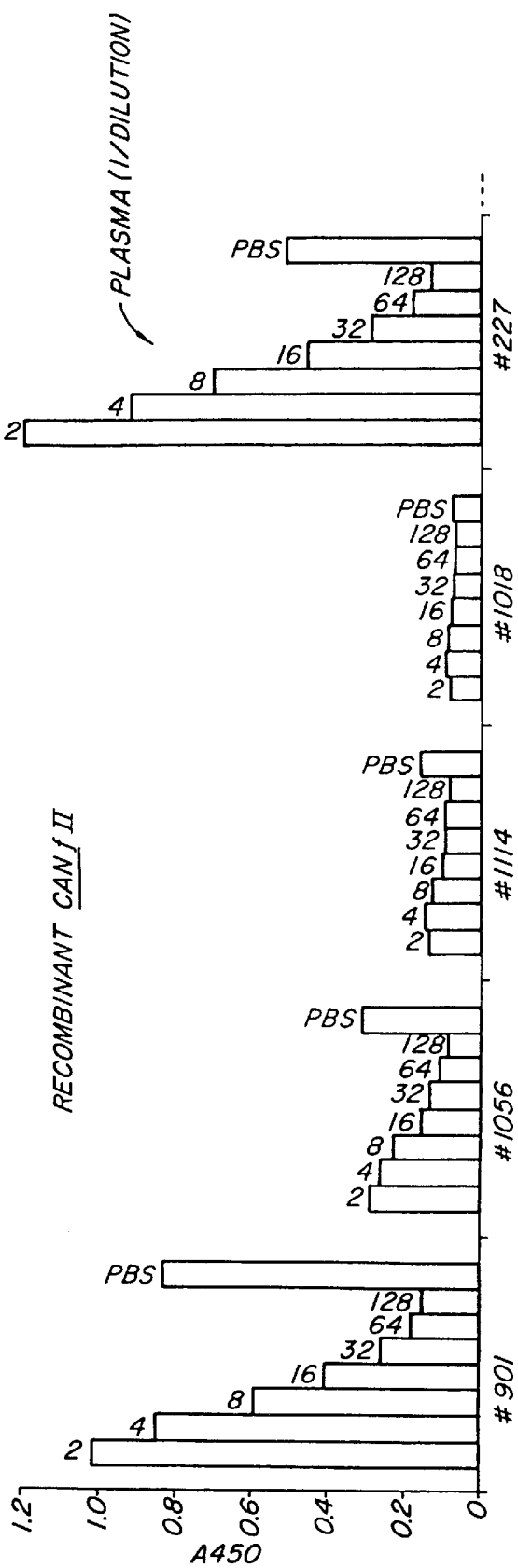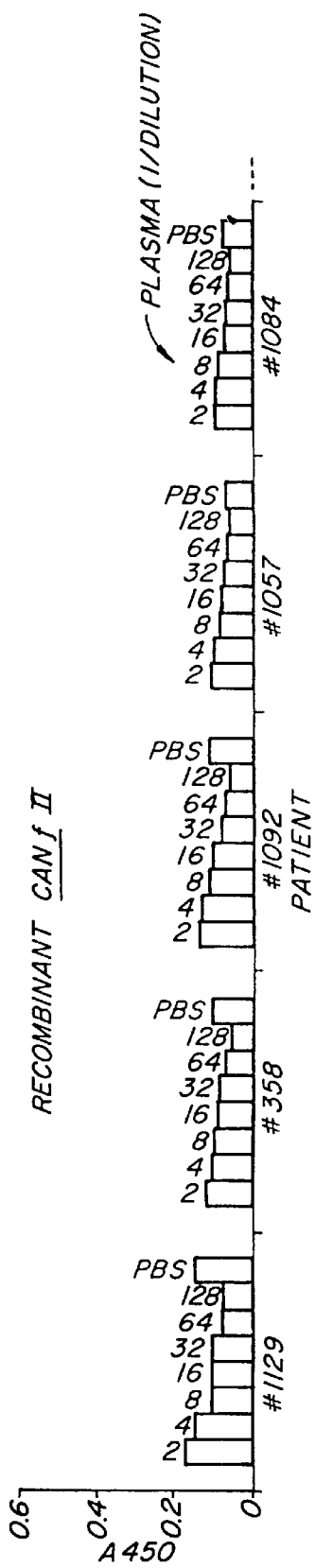
Fig. 22B (PART 1)
Fig. 22B (PART 2)

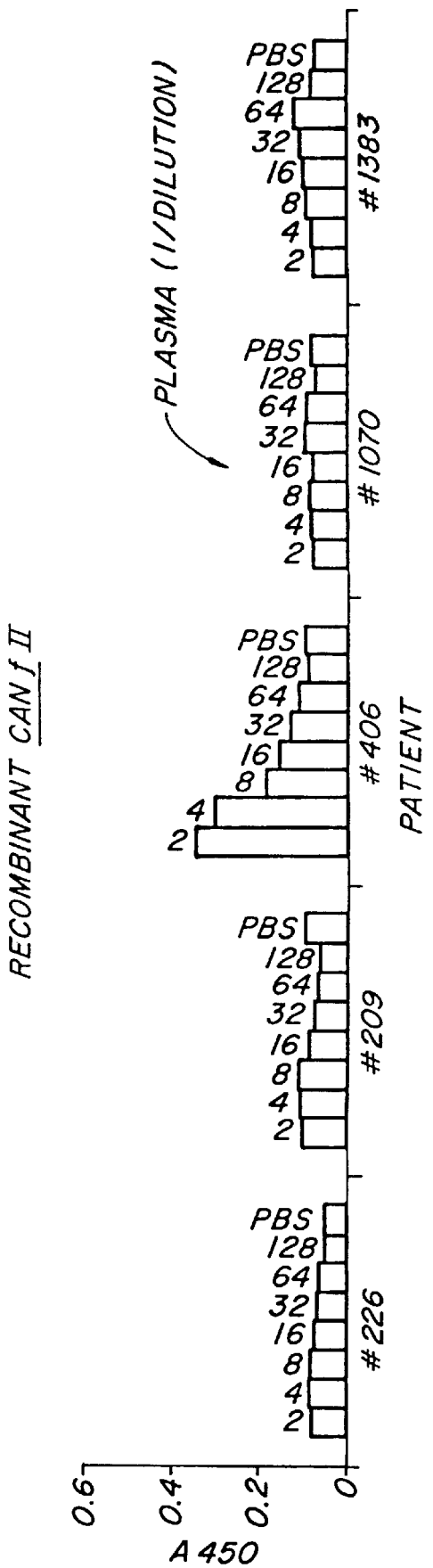
Fig. 22B (PART 3)

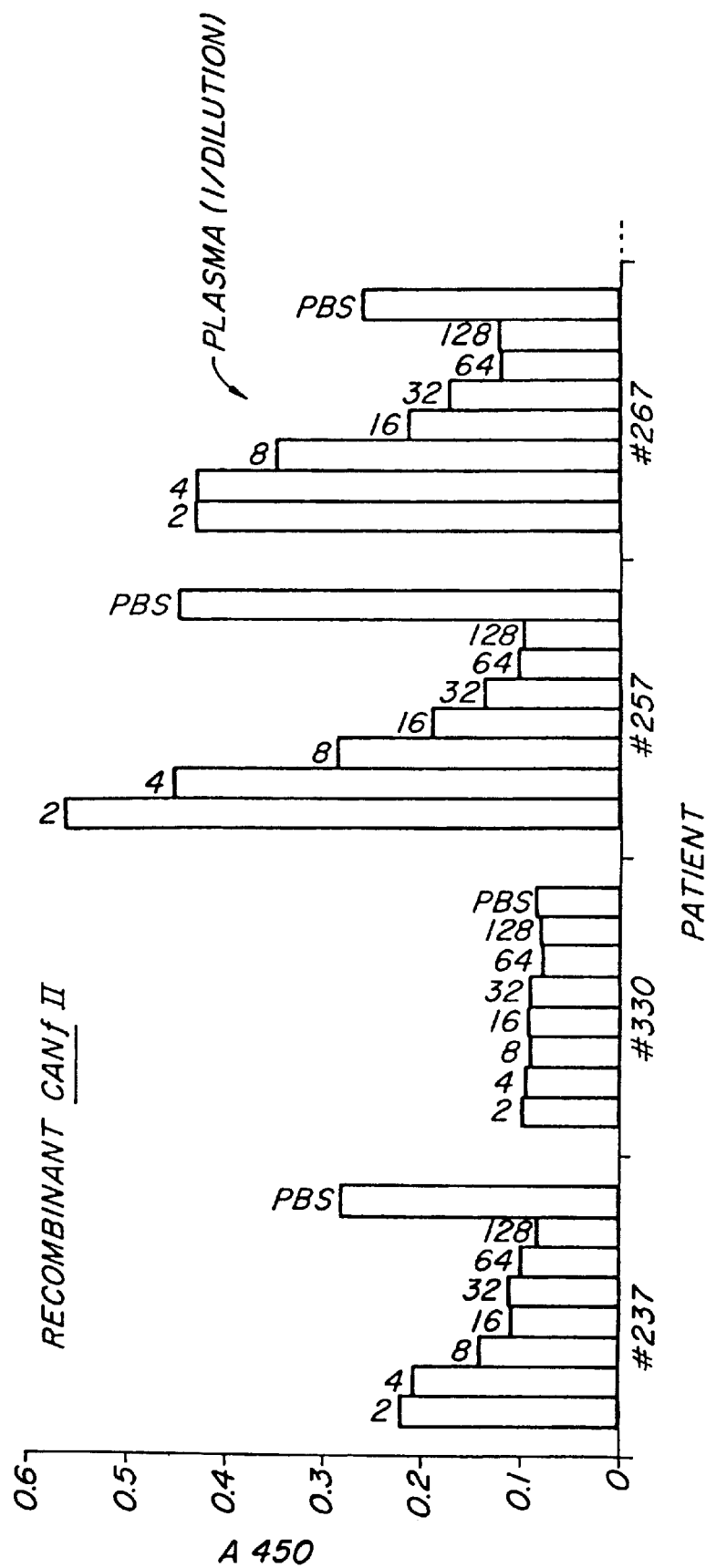
Fig. 22C (PART 1)

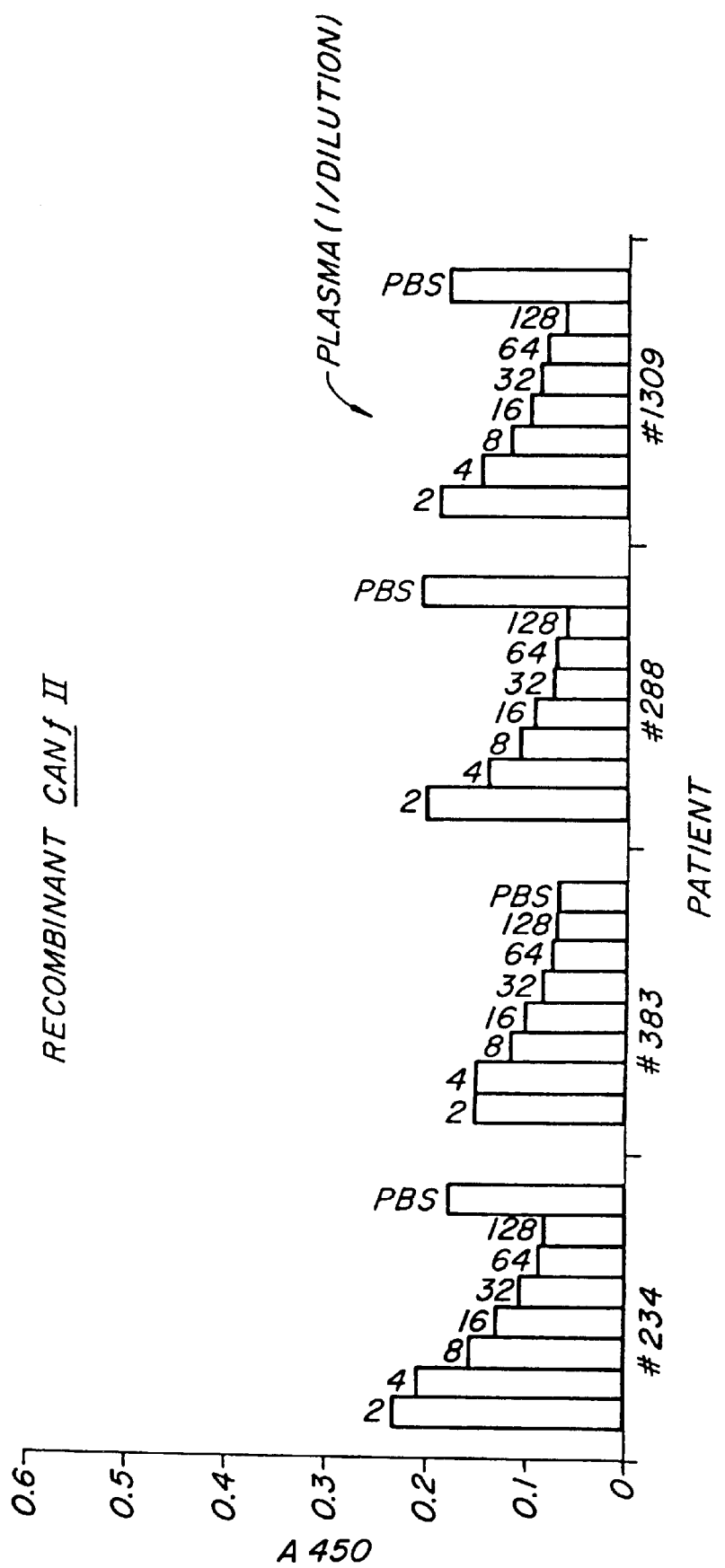
Fig. 22C (PART 2)

| | | | | | |
|---|---|---|---|---|---|
| 1a cons | ---------- | ---------- | ---------- | ---------- | ---------- | |
| 1c cons | .......... | .......... | .......... | .......... | .......... | |
| 1j cons | ---------- | ---------- | ---------- | ---------- | ---------- | |
| Consensus | AGAGCTGGAC | CCGTGTGTGT | GCTGGCCAAT | GAGCCCTGGA | GGGTCCGGCT | 50 |
| 1a cons | ---------- | ---------- | ---------- | ---------- | ---------- | |
| 1c cons | .......... | .......... | .......... | .......... | .......... | |
| 1j cons | ---------- | ---------- | ---------- | ---------- | ---------- | |
| Consensus | CCAGAGTACC | CTCTTGGCAC | AGGGCCGAGT | CCATCGGGAC | AGATGAACCT | 100 |
| 1a cons | ---------- | ---------- | ---------- | ---------- | ---------- | |
| 1c cons | .......... | .......... | .......... | .......... | .......... | |
| 1j cons | ---------- | ---------- | ---------- | ---------- | ---------- | |
| Consensus | AGAGGACTCC | ACTGCCCCTCC | CATCCACGGG | GCCGGGTCAC | CAGACTCTGC | 150 |
| 1a cons | ---------- | ---------- | ---------- | ---------- | ---------- | |
| 1c cons | .......... | .......... | .......... | .......... | .......... | |
| 1j cons | ---------- | ---------- | ---------- | ---------- | ---------- | |
| Consensus | AAGTCTCCAG | CTGTCGCCAA | ACCCAGACAG | AAGGTGCTGT | GGACATGCAG | 200 |
| 1a cons | ----....A. | ..CTT.T..  | ........TT | .......... | .......... | 45 |
| 1c cons | .......T.| --.TGA.C..  | ........CC | .......... | .......... | 246 |
| 1j cons | .......T.. | --TGA.C.-- | ........CC | .......... | .......... | 49 |
| Consensus | CTCCTACWGC | ACYKWCYGTC | TGGGYYTGGC | ACTGATCTGT | GGCCTCCAGG | 250 |

Fig. 23A

```
1a cons    ........................................................    95
1c cons    ........................................................    296
1j cons    ........................................................    99
Consensus  CTCAGGAGGG AAACCATGAG GAGCCCCAGG GAGGCCTAGA GGAGCTGTCT        300

1a cons    .........T ........T. ........C. .........         145
1c cons    ..................................                346
1j cons    ..................................                149
Consensus  GGGAGGTGGC ACTCCGTTGC CCTGGCCTCC AACAAGTCCG ATCTGAYCAA        350

1a cons    ..................................                195
1c cons    ..................................                396
1j cons    ..................................                199
Consensus  ACCCTGGGGG CACTTCAGGG TTTTCATCCA CAGCATGAGC GCAAAGGACG        400

1a cons    G.........                                         245
1c cons    G.........                                         246
1j cons    T.........                                         249
Consensus  KCAACCTGCA CGGGGATATC CTTATACCGC AGGACGGCCA GTGCGAGAAA        450

1a cons    ..................................                295
1c cons    ..................................                496
1j cons    ..................................                299
Consensus  GTCTCCCTCA CTGCGTTCAA GACTGCCACC AGCAACAAAT TTGACCTGGA        500
```

Fig. 23B

| | | |
|---|---|---|
| 1a cons | ................................................. | 345 |
| 1c cons | ................................................. | 546 |
| 1j cons | ................................................. | 349 |
| Consensus | GTACTGGGGA CACAATGACC TGTACCTGGC AGAGGTAGAC CCCAAGAGCT | 550 |
| 1a cons | ................................................. | 395 |
| 1c cons | ................................................. | 596 |
| 1j cons | ................................................. | 399 |
| Consensus | ACCTGATTCT CTACATGATC AACCAGTACA ACGATGACAC CAGCCTGGTG | 600 |
| 1a cons | ........C........................................ | 445 |
| 1c cons | ........T........................................ | 646 |
| 1j cons | ........C........................................ | 449 |
| Consensus | GCTCACYTGA TGGTCCGGGA CCTCAGCAGG CAGCAGGACT TCCTGCCGGC | 650 |
| 1a cons | ................................................. | 495 |
| 1c cons | ................................................. | 696 |
| 1j cons | ................................................. | 499 |
| Consensus | ATTCGAATCT GTATGTGAAG ACATCGGTCT GCACAAGGAC CAGATTGTGG | 700 |
| 1a cons | ................................................. | 545 |
| 1c cons | ................................................. | 746 |
| 1j cons | ................................................. | 549 |
| Consensus | TTCTGAGCGA TGACGATCGC TGCCAGGGTT CCAGAGACTA GGGCCTCAGC | 750 |

Fig. 23C

```
1a cons    . . . . . . . . .T . . . . . . . . . . . . . . . . . . . . . . . . . . . . . . . . . . . . . . . . . . . . . . . . . . . .   595
1c cons    . . . . . . . . .-—————————————————————————————————————————————————————  785
1j cons    . . . . . . . . .C . . . . . . . . . . . . . . . . . . . . . . . . . . . . . . . . . . . . . . . . . . . . . . . . . . . .   599
Consensus  CYACGCAGAG AGCCAAGCAG CAGGATCTCA CCTGCCTGAG GACTCAGACC   800

1a cons    . . . . . . . . . . . . . .G. . . . . . . . . . . . . . . . . . . . . . . . . . . . . . . . . . . . . .   645
1c cons    ——————————— . . . .T————— ——————————— ——————————— ———————————   791
1j cons    ——————————— . . . .G————— ——————————— ——————————— ———————————   649
Consensus  TATAGGCTCG GKGGACACCG TACTCAGCTC TGCGTCCCTC TCTGCGAACC   850

1a cons    . . . . . . . . . . . . . . . . . . . . . . . . . . . . . . . . . . . . . . . . . . . . . . . . . . . . . . . . . . . . . .   695
1c cons    ——————————— ——————————— ——————————— ——————————— ———————————   791
1j cons    ——————————— ——————————— ——————————— ——————————— ———————————   699
Consensus  CTCCAGGTGA TCCCAGCAAC AACACCCACC TGCGCTTCCA TGTGCGGCCC   900

1a cons    . . . . . . . . . . . . . . . . . . . . . . . . . . . . . . . . . . . . . . . . . . . . . . . . . . . . . . . . . . . . . .   745
1c cons    ——————————— ——————————— ——————————— ——————————— ———————————   791
1j cons    ——————————— ——————————— ——————————— ——————————— ———————————   749
Consensus  TGTCCAGCCT GCGCCCACTC CCTGCCTGGG CAGCCACACA CTCCCCAGCC   950

1a cons    . . . . . . . . . . . . . . . . . . . . . . . . . . . . . . . . . . . . . . . . . . . . . . . . . . . . . . . . . . . . . .   793
1c cons    ——————————— ——————————— ——————————— ——————————— ———————————   791
1j cons    . . . . . . . . . . . . . . . . . . . . . . . . . . . . . . . . . . . . . . . . . . .—————— ——————————— ———————————   774
Consensus  CCCTGCTATG GTCCCTCCTC GCATAATAAA GGACATTCCG TTCAAAAA    998
```

Fig. 23D

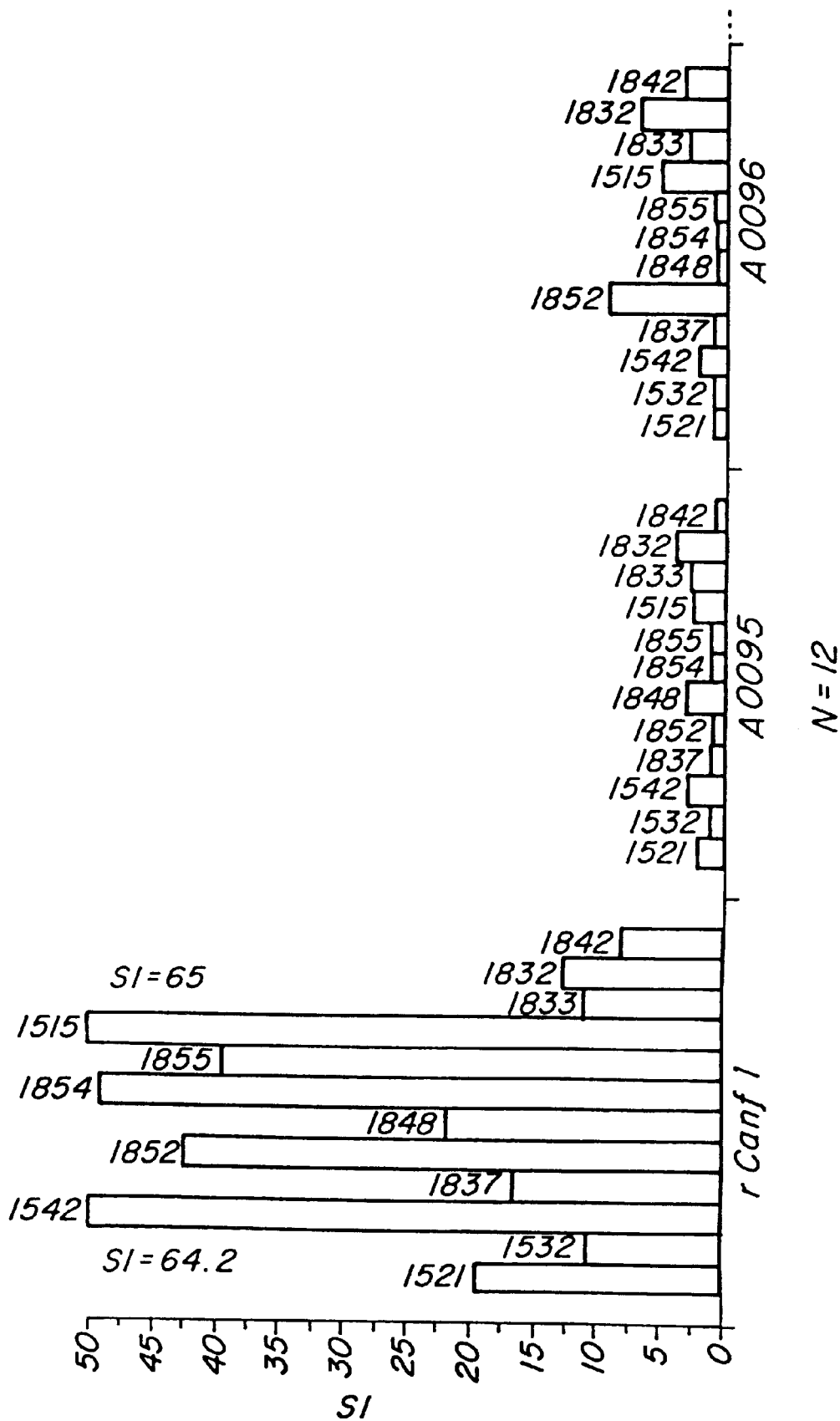
Fig. 24 (PART 1)

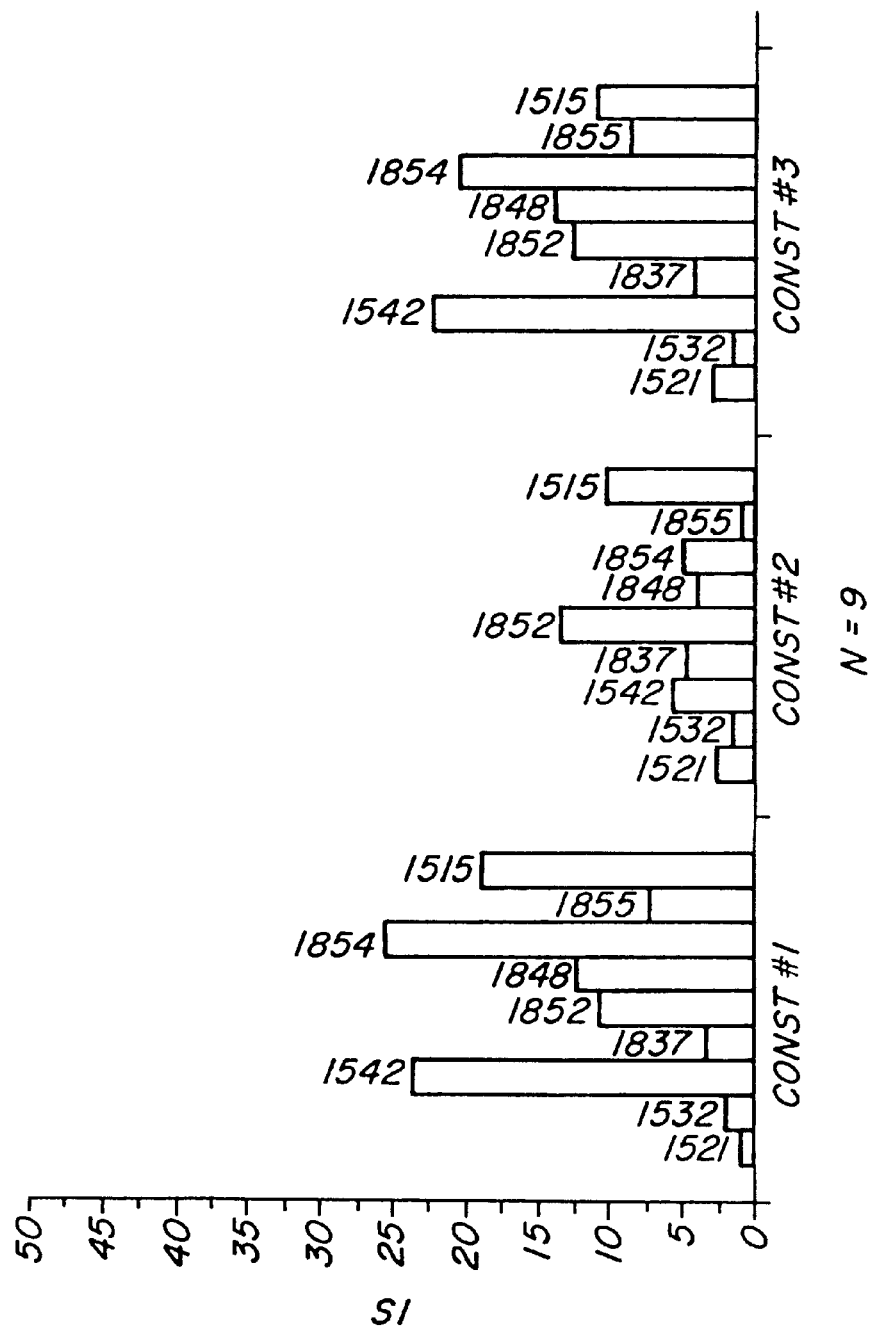
Fig. 24 (PART 2)

ALLERGENIC PROTEINS AND PEPTIDES FROM DOG DANDER AND USES THEREFOR

This application is a continuation application of Ser. No. 08/491,861 filed on Oct. 27, 1995, now U.S. Pat. No. 5,939,283 which in turn is a continuation application of Ser. No. PCT/US93/12468 filed on Dec. 30, 1993, which is a continuation-in-part of 08/156,549 filed on Nov. 22, 1993, now abandoned, which is a continuation-in-part of 07/999,712 filed on Dec. 31, 1992 now abandoned. The contents of all of the aforementioned application(s) are hereby incorporated by reference.

BACKGROUND OF THE INVENTION

Approximately 10% of the population become hypersensitized (allergic) upon exposure to antigens from a variety of environmental sources. Those antigens that induce immediate and/or delayed types of hypersensitivity are known as allergens (King, T. P., (1976) *Adv. Immunol.*, 23:77–105. These include products of grasses, trees, weeds, animal dander, insects, food, drugs, and chemicals. Genetic predisposition of an individual is believed to play a role in the development of immediate allergenic responses (Young, R. P. et al., (1990) *Clin. Sci.*, 79:19a) such as atopy and anaphylaxis whose symptoms include hay fever, asthma, and hives.

The antibodies involved in atopic allergy belong primarily to the IgE class of immunoglobulins. IgE binds to basophils, mast cells and dendritic cells via a specific, high-affinity receptor FcεRI (Kinet, J. P., (1990) *Curr. Opin. Immunol.*, 2:499–505). Upon combination of an allergen acting as a ligand with its cognate receptor IgE, FCεRI bound to the IgE may be cross-linked on the cell surface, resulting in physiological manifestations of the IgE-allergen interaction. These physiological effects include the release of, among other substances, histamine, serotonin, heparin, chemotactic factor(s) for eosinophilic leukocytes and/or leukotrienes C4, D4, and E4, which cause prolonged constriction of bronchial smooth muscle cells (Hood, L. E. et al., *Immunology* (2nd ed.), The Benjamin/Cumming Publishing Co., Inc. (1984)). Hence, the ultimate consequence of the interaction of an allergen with IgE are allergic symptoms triggered by release of the aforementioned mediators. Such symptoms may be systemic or local in nature, depending on the route of entry of the antigen and the pattern of deposition of IgE on mast cells or basophils. Local manifestations generally occur on epithelial surfaces at the site of entry of the allergen. Systemic effects can induce anaphylaxis (anaphylactic shock) which results from IgE-basophil response to circulating (intravascular) antigen.

The pet dog (*Canis familiaris*) is kept in households the world over. In houses and public schools where dogs have been kept on a regular basis, dog dander allergens can be detected in dust samples (Wood, R. A. et al., (1988) *Am Rev Respir. Dis.*, 137:358–363, and Dybendal, T. et al., (1989) *Allergy*, 44:401–411). The prevalence of allergy to dogs as assessed by skin prick test is approximately 15% (Haahtela, T. et al., (1981) *Allergy*, 36:251-256, and de Groot, H. et al., (1991) *J. Allergy Clin. Immunol.*, 87:1056–1065). In one study, sensitivity to dog allergen(s) was detected in 40% of asthmatic children, even though dogs were not kept as pets in their homes (Vanto, T. and Koivikko, A., (1983) *Acta Paediatr Scand.*, 72:571–575).

Treatment of patients with dog allergy by administration of dog dander extracts has not proven to be as efficacious as treatment of cat allergic patients with cat dander extracts (Hedlin, G. et al.,(1991) *J. Allergy Clin Immunol.*, 87:955–964). As with any desensitization scheme involving injection of increasing doses of allergen(s), there are the drawbacks of potential anaphylaxis during treatment, and the possible necessity of continuing therapy over a period of several years to build up sufficient tolerance that results in significant diminution of clinical symptoms.

Dog hair and dander extracts are complex mixtures containing a number of allergenic proteins. (Loewenstein, H et al., (1982) *Proceedings 11th International Congress of Allergology and Clinical Immunology*, London, pp 545–548; Uchlin, T et al., (1984) *Allergy*, 39:125–133; Yman, L. et al., (1984) *Int. Arch. Allergy Appl. Immunol.U.* 44:358–368; Spitzauer, S. et al., (1993) *Int. Arch. Allergy Immunol.*, 100:60–67). Two allergens present in dog hair/dander have been purified using immunoaffinity chromatography. A major allergen from dog, Can f I (Nomenclature according to the criteria of the IUIS (Marsh, D. G. et al., (1988) *Clin. Allergy*, 18:201–209; Ag13 according to original nomenclature), has been partially purified by two groups (Schou, C. et al., (1991) *Clin. and Exp. Allergy*, 21:321-328 and de Groot et al., supra). Both groups, partially purified Can f I was established as an allergen by CRIE analysis (Ford A. W. et al., (1989) *Clin. Exp. Allergy*, 19:183–190), and then rabbits or Balb/b mice were immunized to obtain polyclonal or monoclonal antibodies against the allergen, respectively. Immunoaffinity purified Can f I (~25 kD in molecular weight, with a minor component ~18 kD) which elicited a high frequency of positive skin prick tests among dog allergic patients was able to deplete 50–70% of IgE binding to dog dander extracts in RAST (radioallergosorbent test) analysis. While de Groot et al. did not attempt to determine any amino acid sequence of Can f I, Schou et al. found the amino terminus of their immunoaffinity purified Can f I was blocked. Hence, no amino acid sequence of Can f I is presently in the public domain.

The presence of a second (minor) allergen in dog extract was detected by binding of IgE antibodies to dog dander/hair extracts by several groups (de Groot et al., supra, Schou, C. et al., supra and Spitzauer et al., (1993) *Int. Arch. Allergy Immunol.*, 100:60–67). The molecular weight of a minor allergen was reported to be 18 kD (Schou et al., supra), 19 kD (Spitzauer et al., supra) and 27 kd (de Groot et el., supra). It is difficult however to correlate these results since only one group (de Groot et al., supra) affinity purified an allergen designated Can f II (originally named Dog 2 allergen). Can f II was purified from dog dander extracts in a manner analogous to Can f I using monoclonal antibodies generated to a second allergen present in extracts (de Groot et al., supra). Molecular weight of Can f II reported by this group as ~27 kD was later verified to be ~24 kD (Aalberse, R. C. personal communication). Purified Can f II allergen was found to react with IgE of only 66% of dog allergic patients. In RAST analysis, Can f II allergen was able to compete with 23% of the IgE directed against dog dander extract. The amino acid sequence of Can f II has not been previously determined.

Many patients with sensitivity to dog dander allergens are treated currently by administration of small, gradually increasing doses of dog dander extracts. Use of these extracts has multiple drawbacks, including potential anaphylaxis during treatment and the necessity of continuing therapy, often for a period of several years to build up sufficient tolerance and significant diminution of clinical symptoms. The ability to substitute compositions of at least the major dog dander allergens, such as Can f I and Can f II, would overcome several of these drawbacks. Thus, a source of pure allergen that could be provided in quantity for use as a diagnostic or therapeutic reagent and therapeutic methods that would overcome the drawbacks associated with dog dander extracts are highly desirable.

SUMMARY OF THE INVENTION

This invention provides isolated nucleic acids encoding peptides having at least one biological activity of Can f I or Can f II, protein allergens of the species *Canis familiaris*. Preferred nucleic acids are cDNAs having a nucleotide sequence shown in FIG. 5 (SEQ ID NO: 1)(Can f I) and FIG. 18 (SEQ ID NO: 67) (Can f II). The invention also pertains to peptides encoded by all or a portion of such cDNAs (SEQ ID NO: 1 and SEQ ID NO: 67) and having at least one biological activity of Can f I or Can f II. Also contemplated are isolated nucleic acids which hybridize under high stringency conditions (e.g., equivalent to 20–27° C. below Tm and 1 M NaCl ) to a nucleic acid having a nucleotide sequence shown in FIG. 5 (SEQ ID NO: 1) or FIG. 18 (SEQ ID NO: 67) or which encodes a peptide comprising all or a portion of an amino acid sequence of FIG. 5 (SEQ ID NO: 2)(Can f I) or FIG. 18 (SEQ ID NO: 68)(Can f II). Nucleic acids which encode peptides having an activity of Can f I or Can f II and having at least 50% homology with a sequence shown in FIG. 5 (SEQ ID NO: 2)(Can f I) or FIG. 18 (SEQ ID NO: 68)(Can f II) are also featured. Peptides having a Can f I or Can f II activity produced by recombinant expression of a nucleic acid of the invention, and peptides having a Can f I or Can f II activity prepared by chemical synthesis are also featured by this invention. Preferred peptides have the ability to induce a T cell response, which may include T cell stimulation (measured by, for example, T cell proliferation or cytokine secretion) or T cell nonresponsiveness (i.e., contact with the peptide or a complex of the peptide with an MHC molecule of an antigen presenting cell induces the T cell to become unresponsive to stimulatory signals or incapable of proliferation). Other preferred peptides, either apart from or in addition to the ability to induce a T cell response, have the ability to bind the dog dander specific IgE of dog dander-allergic subjects. Such peptides are useful in diagnosing sensitivity to dog dander in a subject. Still other peptides, either apart from or in addition to the ability to induce a T cell response, have a significantly reduced or negligible ability to bind dog dander-allergic IgE. Such peptides are particularly useful as therapeutic agents.

Other preferred peptides comprise an amino acid sequence shown in FIG. 5 (SEQ ID NO: 2) (Can f I) or FIG. 18 (SEQ ID NO: 68)(Can f II). In one embodiment, peptides having a Can f I or Can f II activity and comprising a portion of the amino acid sequence of FIG. 5 (SEQ ID NO: 2) or FIG. 18 (SEQ ID NO: 68) are at least about 8–30 amino acids in length, preferably about 10–20 amino acids in length, and most preferably about 10–16 amino acids in length.

Another aspect of the invention features antibodies specifically reactive with a peptide having a Can f I or Can f II activity. A peptide having an activity of Can f I or Can f II can be used in compositions suitable for pharmaceutical administration. For example, such compositions can be used in a manner similar to dog dander extracts to treat or prevent allergic reactions to dog dander in a subject. Nucleic acids of the invention and peptides having an activity of Can f I or Can f II can be also used for diagnosing sensitivity in a subject to a dog dander.

BRIEF DESCRIPTION OF THE DRAWINGS

FIG. 1 shows degenerate primer pairs based on residues 9–15 and 30–37 of the mature Can f I protein used in the MOPAC technique of PCR amplification. Two internal degenerate oligonucleotide probes based on Can f I protein residues 17–24 (Dog Probe 1) and 88–94 (Dog Probe 2) are shown.

FIG. 2 shows oligonucleotide primers used in a RACE PCR protocol to obtain the 3' portion of the Can f I cDNA. A degenerate oligonucleotide probe (Dog Probe 4) is also shown.

FIG. 3 shows primers used in an anchored PCR technique to determine the 5' end of the Can f I cDNA. A degenerate oligonucleotide probe, Dog Probe 0, based on residues 9–17 of the Can f protein is shown.

FIG. 5 is the cDNA sequence and deduced amino acid sequence of Can f I.

FIG. 9 shows the alignment of three partial 3° Can f I cDNA sequences (Can f I, 2Can f I and 3Can f I). An (*) indicates that the position in the alignment is perfectly conserved and a (.) indicates that the position is well conserved. A (-) was inserted where necessary for purposes of alignment.

FIG. 16 is the nucleotide sequence of primers used in cloning Can f II cDNA.

FIG. 18 is the cDNA sequence and deduced amino acid sequence (from Clone 1c) of Can f II.

FIG. 19 is a comparison of the deduced amino acid sequence of Can f II based on the cDNA sequence of clone 1c and a portion of the native Can f II determined by protein sequencing of the N-terminus. The amino acid residues of a signal peptide are numbered −19 to −1.

FIG. 21 is a comparison of the amino acid sequence of Can f II with homologus proteins MUP 6 Mouse and Rat A2U. The alignment was made with GeneWorks program. The signal sequences are underlined. Amino acid residues which are identical in all three proteins are boxed.

FIGS. 22A–C are graphic representations of a direct binding assays of human IgE binding to native Can f II and recombinant Can f II.

FIG. 23 is the nucleotide consensus sequence among cDNA clones 1a, 1c and 1j encoding partial or full length Can f II.

FIG. 24 is a graphic representation depicting the response of T cell lines from 12 patients primed in vitro with recombinant Can f I (rCan f I) and analyzed for response to rCan f I and various peptides derived from Can f I by stimulation index. A stimulation index equal to or greater than two times the background is considered "positive."

DETAILED DESCRIPTION OF THE INVENTION

Figure 4:
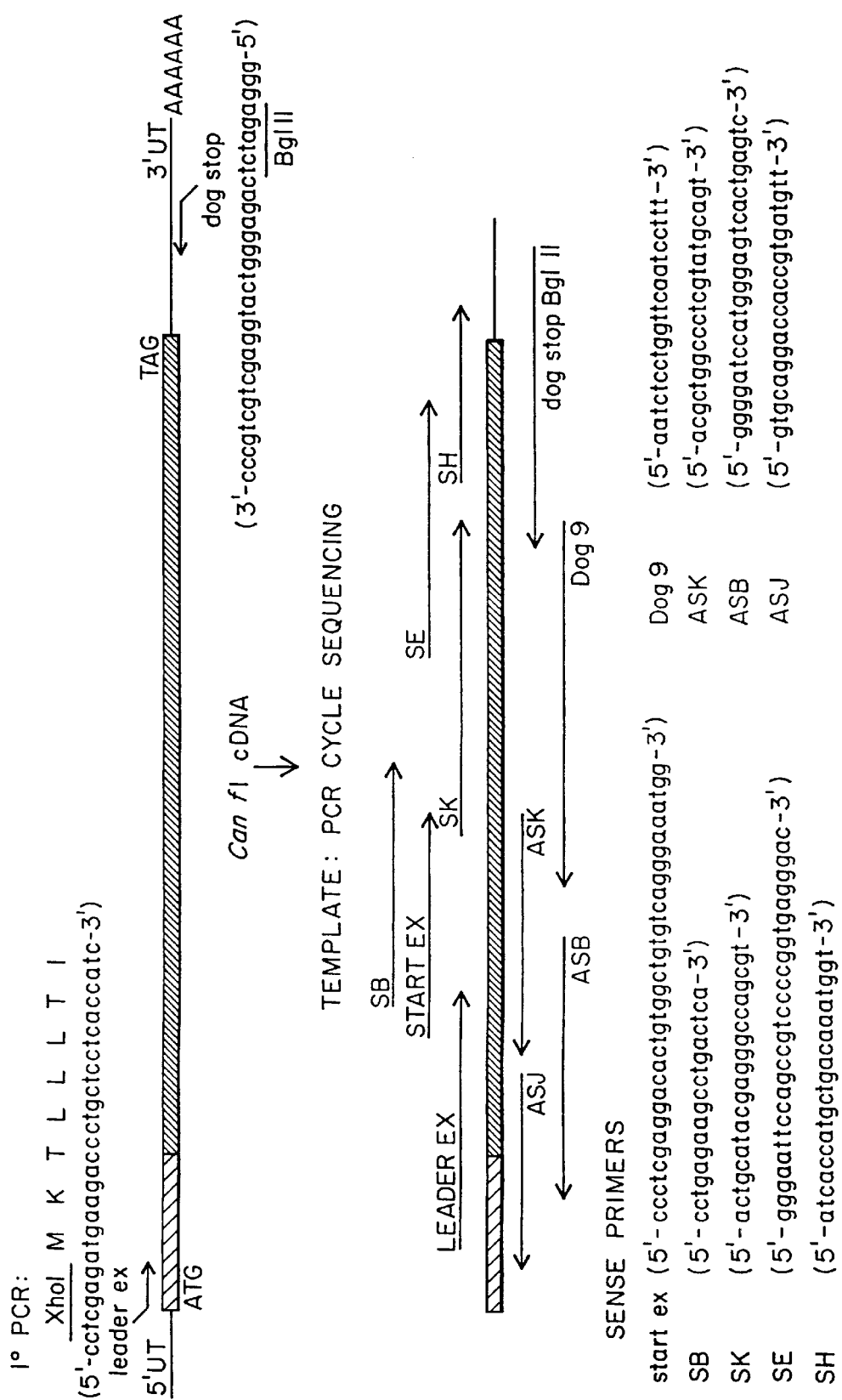
FIG. 4 is a schematic representation of a PCR sequencing strategy used to obtain the sequence of the mature Can f I protein from both strands of amplified cDNA.

This invention pertains to isolated nucleic acids encoding peptides having at least one biological activity of Can f I or Can f II, allergens of the species *Canis familiaris*. Preferably, the nucleic acid is a cDNA comprising a nucleotide sequence shown in FIG. 5 (SEQ ID NO: 1) (Can f I) or FIG. 18 (SEQ ID NO:67) (Can f II).

The cDNA shown in FIG. 5 (SEQ ID NO: 1) encodes a Can f I peptide which includes a 26 amino acid leader sequence encoded by base 1 through base 78. This leader sequence is not found in the mature Can f I protein, which is encoded by bases 79 through 525. The deduced amino acid sequence of Can f I based on this cDNA is also shown in FIG. 5 (SEQ ID NO: 2). The cDNA encodes a mature peptide having a predicted molecular weight of 19.2 kDa, with a pI of 5.53 and a single potential N-linked glycosylation site. A culture of *E. coli* transfected with an expression vector containing the cDNA encoding Can f I was deposited under the Budapest Treaty with the American Type Culture Collection on Dec. 22, 1992 and assigned accession number 69167.

The cDNA shown in FIG. 18 (SEQ ID NO: 67) encodes a Can f II peptide which includes a 19 amino acid leader sequence encoded by base 195 through base 251. This leader sequence is not found in the mature Can f II protein, which is encoded by bases 252 through 734. The deduced amino acid sequence of Can f II based on this cDNA is shown in FIG. 18 (SEQ ID NO: 68). The cDNA encodes a Can f II peptide having a predicted molecular weight of 18.229 kDa, with a pI of 4.54 for a mature recombinant Can f II protein and a pI of 4.44 for a full length (including signal sequence), recombinant Can f II protein, and a single potential N-linked glycosylation site. N-linked glycosylation may increase the molecular weight of the peptide and may alter the pI of the mature protein. A culture of *E. coli* transfected with an expression vector containing the cDNA encoding Can f II was deposited under the Budapest Treaty with the American Type Culture Collection on Dec. 29, 1993 and assigned accession number 69167.

Accordingly, one aspect of this invention pertains to isolated nucleic acids comprising nucleotide sequences encoding Can f I or Can f II, fragments thereof encoding peptides having at least one biological activity of Can f I or Can f II, and/or equivalents of such nucleic acids. The term nucleic acid as used herein is intended to include such fragments and equivalents. The term equivalent is intended to include nucleotide sequences encoding functionally equivalent Can f I or Can f II proteins or functionally equivalent peptides having an activity of Can f I or Can f II. As defined herein, a peptide having an activity of Can f I or Can f II has at least one biological activity of the Can f I or Can f II allergen. Equivalent nucleotide sequences will include sequences that differ by one or more nucleotide substitutions, additions or deletions, such as allelic variants, and will also include sequences that differ from the nucleotide sequence encoding Can f I or Can f II shown in FIG. 5 (SEQ ID NO: 1) or FIG. 18 (SEQ ID NO: 67) due to the degeneracy of the genetic code. Equivalents will also include nucleotide sequences that hybridize under stringent conditions (i.e., equivalent to about 20–27° C. below melting temperature ($T_m$) and about 1M salt) to the nucleotide sequence of Can f I shown in FIG. 5 (SEQ ID NO: 1) or Can f II shown in FIG. 18 (SEQ ID NO: 67).

Peptides referred to herein as having an activity of Can f I or Can f II or having a Can f I or Can f II activity are defined herein as peptides that have an amino acid sequence corresponding to all or a portion of the amino acid sequence of Can f I or Can f II shown in FIG. 5 (SEQ ID NO: 2) or FIG. 18 (SEQ ID NO: 68) which peptide has at least one biological activity of Can f I or Can f II. For example, a peptide having an activity of Can f I or Can f II may have the ability to induce a response in Can f I or Can f II restricted T cells such as stimulation (e.g., T cell proliferation or cytokine secretion) or to induce T cell non-responsiveness. Alternatively, or additionally, a peptide having an activity of Can f I or Can f II may have the ability to bind (to be recognized by) immunoglobulin E (IgE) antibodies of dog dander-allergic subjects. Peptides which bind IgE are useful in methods of detecting allergic sensitivity to Can f I or Can f II in a subject. Peptides that do not bind IgE, or bind IgE to a lesser extent than a purified, native Can f I or Can f II protein binds IgE are particularly useful as therapeutic agents.

In one embodiment, the nucleic acid is a cDNA encoding a peptide having an activity of Can f I or Can f II. Preferably, the nucleic acid is a cDNA molecule comprising at least a portion of the nucleotide sequence encoding Can f I or Can f II, shown in FIG. 5 (SEQ ID NO:1) and FIG. 18 (SEQ ID NO: 67). A preferred portion of the cDNA molecules of FIG. 5 and FIG. 18 includes the coding region of the molecule.

In another embodiment, the nucleic acid of the invention encodes a peptide having an activity of Can f I or Can f II and comprising an amino acid sequence shown in FIG. 5 (SEQ ID NO:2) (Can f I) or FIG. 18 (SEQ ID NO: 68) (Can f II). Preferred nucleic acids encode a peptide having a Can f I or Can f II activity and having at least about 50% homology, more preferably at least about 60% homology and most preferably at least about 70% homology with the sequence shown in FIG. 5 (SEQ ID NO: 1) (Can f I) or FIG. 18 (SEQ ID NO: 67) (Can f II). Nucleic acids which encode peptides having a Can f I or Can f II activity and having at least about 90%, more preferably at least about 95%, and most preferably at least about 98–99% homology with a sequence set forth in FIG. 5 (SEQ ID NO: 2) (Can f I) or FIG. 18 (SEQ ID NO: 68) (Can f II) are also within the scope of the invention. Homology refers to sequence similarity between two peptides having an activity of Can f I or Can f II or between two nucleic acid molecules. Homology can be determined by comparing a position in each sequence which may be aligned for purposes of comparison. When a position in the compared sequence is occupied by the same base or amino acid, then the molecules are homologous at that position. A degree of homology between sequences is a function of the number of matching or homologous positions shared by the sequences.

Another aspect of the invention provides a nucleic acid which hybridizes under high or low stringency conditions to a nucleic acid which encodes a peptide having all or a portion of an amino acid sequence shown in FIG. 5 (SEQ ID NO: 2) (Can f I) or FIG. 18 (SEQ ID NO: 68) (Can f II). Appropriate stringency conditions which promote DNA hybridization, for example, 6.0×sodium chloride/sodium citrate (SSC) at about 45° C., followed by a wash of 2.0×SSC at 50° are known to those skilled in the art or can be found in *Current Protocols in Molecular Biology*, John Wiley & Sons, N.Y. (1989), 6.3.1–6.3.6. For example, the salt concentration in the wash step can be selected from a low stringency of about 2.0×SSC at 50° C. to a high stringency of about 0.2×SSC at 50° C. In addition, the temperature in the wash step can be increased from low stringency conditions at room temperature, about 22° C., to high stringency conditions at about 65° C.

Isolated nucleic acids encoding peptides having an activity of Can f I or Can f II, as described herein, and having a sequence which differs from the nucleotide sequences shown in FIG. 5 (SEQ ID NO: 1) and FIG. 18 (SEQ ID NO: 67) due to degeneracy in the genetic code are also within the scope of the invention. Such nucleic acids encode functionally equivalent peptides (i.e., a peptide having an activity of Can f I or Can f II) but differ in sequence from the sequences of FIG. 5 and FIG. 18 due to degeneracy in the genetic code. For example, a number of amino acids are designated by more than one triplet. Codons that specify the same amino acid, or synonyms (for example, CAU and CAC are synonyms for histidine) may result in "silent" mutations which do not affect the amino acid sequence of the Can f I or Can f II protein. However, it is expected that DNA sequence polymorphisms that do lead to changes in the amino acid sequence of Can f I or Can f II will exist within the dog dander population. One skilled in the art will appreciate that these variations in one or more nucleotides (up to about 3–4% of the nucleotides) of the nucleic acids encoding peptides having an activity of Can f I or Can f II may exist among individual pet dogs due to natural allelic variation. Any and all such nucleotide variations and resulting amino acid polymorphisms are within the scope of this invention. Furthermore, there may be one or more isoforms or related, cross-reacting family members of Can f I or Can f II. Such isoforms or family members are defined as proteins related in function and amino acid sequence to Can f I or Can f II, but encoded by genes at different loci.

Fragments of the nucleic acid encoding Can f I or Can f II are also within the scope of the invention. As used herein, a fragment of the nucleic acid encoding Can f I or Can f II refers to a nucleotide sequence having fewer nucleotides than the nucleotide sequence encoding the entire amino acid sequence of Can f I or Can f II protein and which encodes a peptide having an activity of Can f I or Can f II (i.e., a peptide having at least one biological activity of the Can f I or Can f II allergen) as defined herein.

Preferred nucleic acid fragments encode peptides of at least about 10 amino acid residues in length, preferably about 10–20 amino acid residues in length, and more preferably about 12–16 amino acid residues in length. Nucleic acid fragments which encode peptides having a Can f I activity of at least about 30 amino acid residues in length, at least about 40 amino acid residues in length, at least about 60 amino acid residues in length, at least about 80 amino acid residues in length, at least about 100 amino acid residues in length, and at least about 140 residues in length or more are also within the scope of this invention. Nucleic acid fragments which encode peptides having a Can f II activity of at least about 30 amino acid residues in length, at least about 40 amino acid residues in length, at least about 60 amino acid residues in length, at least about 80 amino acid residues in length, at least about 100 amino acid residues in length, at least about 140 residues in length, and at least about 160 amino acid residues in length or more are also within the scope of this invention.

Nucleic acid fragments within the scope of the invention include those capable of hybridizing under high or low stringency conditions with nucleic acids from other animal species for use in screening protocols to detect Can f I or Can f II or allergens that are cross-reactive with Can f I or Can f II. Generally, the nucleic acid encoding a peptide having an activity of Can f I or Can f II will be selected from the bases encoding the mature protein, however, in some instances it may be desirable to select all or part of a peptide from the leader sequence portion of the nucleic acids of the invention. Nucleic acids within the scope of the invention may also contain linker sequences, modified restriction endonuclease sites and other sequences useful for molecular cloning, expression or purification of recombinant peptides having an activity of Can f I or Can f II.

A nucleic acid encoding a peptide having an activity of Can f I or Can f II may be obtained from mRNA present in salivary glands or other organs of the pet dog *Canis familiaris*. It should also be possible to obtain nucleic acids encoding Can f I or Can f II from *Canis familiaris* genomic DNA. For example, the gene encoding Can f I or Can f II can be cloned from either a cDNA or a genomic library in accordance with protocols herein described. A cDNA encoding Can f I or Can f II can be obtained by isolating total mRNA from *Canis familiaris*. Double stranded cDNAs can then be prepared from the total mRNA. Subsequently, the cDNAs can be inserted into a suitable plasmid or bacteriophage vector using any one of a number of known techniques. Genes encoding Can f I or Can f II can also be cloned using established polymerase chain reaction techniques in accordance with the nucleotide sequence information provided by the invention. The nucleic acids of the invention can be DNA or RNA. A preferred nucleic acid is a cDNA encoding Can f I or Can f II having the sequence depicted in FIG. 5 (SEQ ID NO: 1) (Can f I) or FIG. 18 (SEQ ID NO: 67) (Can f II).

This invention also provides expression vectors containing a nucleic acid encoding a peptide having an activity of Can f I or Can f II, operably linked to at least one regulatory sequence. Operably linked is intended to mean that the nucleotide sequence is linked to a regulatory sequence in a manner which allows expression of the nucleotide sequence. Regulatory sequences are art-recognized and are selected to direct expression of the peptide having an activity of Can f I or Can f II. Accordingly, the term regulatory sequence includes promoters, enhancers and other expression control elements. Such regulatory sequences are described in Goeddel; *Gene Expression Technology: Methods in Enzymology* 185, Academic Press, San Diego, Calif. (1990). It should be understood that the design of the expression vector may depend on such factors as the choice of the host cell to be transformed and/or the type of protein desired to be expressed. In one embodiment, the expression vector includes a DNA encoding a peptide having an activity of Can f I or Can f II. Such expression vectors can be used to transfect cells to thereby produce proteins or peptides, including fusion proteins or peptides encoded by nucleic acids as described herein.

This invention further pertains to a host cell transfected to express a peptide having an activity of Can f I or Can f II. The host cell may be any procaryotic or eucaryotic cell. For example, a peptide having an activity of Can f I or Can f II may be expressed in bacterial cells such as *E. coli*, insect cells (baculovirus), yeast, or mammalian cells such as Chinese hamster ovary cells (CHO). Other suitable host cells can be found in Goeddel, (1990) supra or known to those skilled in the art.

Expression in eucaryotic cells such as mammalian, yeast, or insect cells can lead to partial or complete glycosylation and/or formation of relevant inter- or intra-chain disulfide bonds of recombinant protein. Examples of vectors for expression in yeast *S. cerivisae* include pYepSec1 (Baldari. et al., (1987) *Embo J.,* 6:229–234), pMFa (Kurjan and Herskowitz, (1982) *Cell,* 30:933–943), pJRY88 (Schultz et al., (1987) *Gene,* 54:113–123), and pYES2 (Invitrogen Corporation, San Diego, Calif.). Baculovirus vectors available for expression of proteins in cultured insect cells (SF 9 cells) include the pAc series (Smith et al., (1983) Mol. *Cell Biol.,* 3:2156–2165) and the pVL series (Lucklow, V. A., and Summers, M.D., (1989) *Virology,* 170:31–39). Generally COS cells (Gluzman, Y., (1981) *Cell,* 23:175 –182) are used in conjunction with such vectors as pCDM 8 (Aruffo, A. and Seed, B., (1987) *Proc. Natl. Acad. Sci. USA,* 84:8573–8577) for transient amplification/expression in mammalian cells, while CHO (dhfr- Chinese Hamster Ovary) cells are used with vectors such as pMT2PC (Kaufman et al., (1987) *EMBO J.,* 6:187–195) for stable amplification/expression in mammalian cells. Vector DNA can be introduced into mammalian cells via conventional techniques such as calcium phosphate or calcium chloride co-precipitation, DEAE-dextran-mediated transfection, or electroporation. Suitable methods for transforming host cells can be found in Sambrook et al., (*Molecular Cloning: A Laboratory Manual,* 2nd Edition, Cold Spring Harbor Laboratory press (1989)), and other laboratory textbooks.

Expression in procaryotes is most often carried out in *E. coli* with either fusion or non-fusion inducible expression vectors. Fusion vectors usually add a number of NH2 terminal amino acids to the expressed target gene. These NH2 terminal amino acids often are referred to as a reporter group. Such reporter groups usually serve two purposes: 1) to increase the solubility of the target recombinant protein; and 2) to aid in the purification of the target recombinant protein by acting as a ligand in affinity purification. Often, in fusion expression vectors, a proteolytic cleavage site is introduced at the junction of the reporter group and the target recombinant protein to enable separation of the target recombinant protein from the reporter group subsequent to purification of the fusion protein. Such enzymes, and their cognate recognition sequences, include Factor Xa, thrombin and enterokinase. Typical fusion expression vectors include pGEX (Amrad Corp., Melbourne, Australia), pMAL (New England Biolabs, Beverly, Mass.) and pRIT5 (Pharmacia, Piscataway, N.J.) which fuse glutathione S-transferase, maltose E binding protein, or protein A, respectively, to the target recombinant protein.

Inducible non-fusion expression vectors include pTrc (Amann et al., (1988) Gene, 69:301–315) and pET 11d (Studier et al., *Gene Expression Technology: Methods in Enzymology,* 185, Academic Press, San Diego, Calif. (1990) 60–89). While target gene expression relies on host RNA polymerase transcription from the hybrid trp-lac fusion promoter in pTrc, expression of target genes inserted into pET 11d relies on transcription from the T7 gn10-lac 0 fusion promoter mediated by coexpressed viral RNA polymerase (T7 gn1). This viral polymerase is supplied by host strains BL21(DE3) or HMS174(DE3) from a resident λ prophage harboring a T7 gn1 under the transcriptional control of the lacUV 5 promoter.

One strategy to maximize recombinant Can f I or Can f II expression in *E. coli* is to express the protein in a host bacteria with an impaired capacity to proteolytically cleave the recombinant protein (Gottesman, S., *Gene Expression Technology: Methods in Enzymology,* 185, Academic Press, San Diego, Calif. (1990) 119–128). Another strategy would be to alter the nucleic acid encoding the Can f I or Can f II protein to be inserted into an expression vector so that the individual codons for each amino acid would be those preferentially utilized in highly expressed *E. coli* proteins (Wada et al., (1992) *Nuc. Acids Res.,* 20:2111–2118). Such alteration of nucleic acids of the invention can be carried out by standard DNA synthesis techniques.

The nucleic acids of the invention can also be chemically synthesized using standard techniques. Various methods of chemically synthesizing polydeoxynucleotides are known, including solid-phase synthesis which, like peptide synthesis, has been fully automated in commercially available DNA synthesizers (See e.g., Itakura et al., U.S. Pat. No. 4,598,049; Caruthers et al., U.S. Pat. No. 4,458,066; and Itakura, U.S. Pat. Nos. 4,401,796 and 4,373,071, incorporated by reference herein).

The present invention further pertains to methods of producing peptides that have an activity of Can f I or Can f II. For example, a host cell transfected with a nucleic acid vector directing expression of a nucleotide sequence encoding a peptide having an activity of Can f I or Can f II can be cultured under appropriate conditions to allow expression of the peptide to occur. The peptide may be secreted and isolated from a mixture of cells and medium containing the peptide having an activity of Can f I or Can f II. Alternatively, the peptide may be retained cytoplasmically and the cells harvested, lysed and the protein isolated. A cell culture includes host cells, media and other byproducts. Suitable media for cell culture are well known in the art. The peptide having an activity of Can f I or Can f II can be isolated from cell culture medium, host cells, or both using techniques known in the art for purifying proteins including ion-exchange chromatography, gel filtration chromatography, ultrafiltration, electrophoresis, and immunoaffinity purification with antibodies specific for a peptide having an activity of Can f I or Can f II.

Another aspect of the invention pertains to isolated peptides having an activity of Can f I or Can f II. A peptide having an activity of Can f I or Can f II has at least one biological activity of the Can f I or Can f II allergen. For example, a peptide having an activity of Can f I or Can f II may have the ability to induce a response in Can f I or Can f II specific T cells such as stimulation (T cell proliferation or cytokine secretion) or to induce T cell non-responsiveness. In one embodiment, a peptide having an activity of Can f I or Can f II stimulates T cells as evidenced by, for example, T cell proliferation or cytokine secretion. In another embodiment, peptides having a Can f I or Can f II activity induce T cell non-responsiveness in which T cells are unresponsive to a subsequent challenge with a Can f I or Can f II peptide following exposure to the peptide. In yet another embodiment, a peptide having a Can f I or Can f II activity has reduced IgE binding activity compared to purified, native Can f I or Can f II protein. A peptide having an activity of Can f I or Can f II may differ in amino acid sequence from the Can f I or Can f II sequence depicted in FIG. 5 (SEQ ID NO:2) (Can f I) or FIG. 18 (SEQ ID NO: 68) (Can f II) but such differences result in a modified protein which functions in the same or similar manner as a native Can f I or Can f II protein or which has the same or similar characteristics of a native Can f Ior Can f II protein. Various modifications of the Can f I or Can f II protein to produce these and other functionally equivalent peptides are described in detail herein. The term peptide, as used herein, refers to peptides, proteins, and polypeptides.

A peptide can be produced by modification of the amino acid sequence of the Can f I or Can f II protein shown in FIG. 5 (SEQ ID NO: 2) (Can f I) or FIG. 18 (SEQ ID NO: 68) (Can f II), such as a substitution, addition, or deletion of an amino acid residue which is not directly involved in the function of the protein. Peptides of the invention can be at least about 10 amino acid residues in length, preferably about 10–20 amino acid residues in length, and more preferably about 10–16 amino acid residues in length. Peptides having an activity of Can f I or Can f II and which are at least about 30 amino acid residues in length, at least about 40 amino acid residues in length, at least about 60 amino acid residues in length, at least about 80 amino acid residues in length, and at least about 100 amino acid residues in length are also included within the scope of this invention.

Another embodiment of the invention provides a substantially pure preparation of a peptide having an activity of Can f I or Can f II. Such a preparation is substantially free of proteins and peptides with which the peptide naturally occurs (i.e., other canine peptides), either in a cell or when secreted by a cell.

The term isolated as used herein refers to a nucleic acid or peptide that is substantially free of cellular material or culture medium when produced by recombinant DNA techniques, or chemical precursors or other chemicals when chemically synthesized. Such proteins or peptides are also characterized as being free of all other dog dander proteins. Accordingly, an isolated peptide having an activity of Can f I or Can f II is produced recombinantly or synthetically and is substantially free of cellular material and culture medium or substantially free of chemical precursors or other chemicals and is substantially free of all other dog proteins. An isolated nucleic acid is also free of sequences which naturally flank the nucleic acid (i.e., sequences located at the 5' and 3' ends of the nucleic acid) in the organism from which the nucleic acid is derived.

Peptides having an activity of Can f I or Can f II can be obtained, for example, by screening peptides recombinantly produced from the corresponding fragment of the nucleic acid of Can f I or Can f II encoding such peptides. In addition, fragments can be chemically synthesized using techniques known in the art such as conventional Merrifield solid phase f-Moc or t-Boc chemistry. For example, the Can f I or Can f II protein may be arbitrarily divided into fragments of desired length with no overlap of the fragments, or preferably divided into overlapping fragments of a desired length. The fragments can be produced (recombinantly or by chemical synthesis) and tested to identify those peptides having a Can f I or Can f II activity (i.e., the ability to induce a T cell response such as stimulation (proliferation, cytokine secretion), nonresponsiveness, and/or has reduced IgE binding activity).

In one embodiment, peptides having an activity of Can f I or Can f II can be identified by the ability of the peptide to stimulate T cells or to induce T cell non-responsiveness. Peptides which stimulate T cells, as determined by, for example, T cell proliferation or cytokine secretion are defined herein as comprising at least one T cell epitope. T cell epitopes are believed to be involved in initiation and perpetuation of the immune response to the protein allergen which is responsible for the clinical symptoms of allergy. These T cell epitopes are thought to trigger early events at the level of the T helper cell by binding to an appropriate HLA molecule on the surface of an antigen presenting cell, thereby stimulating the T cell subpopulation with the relevant T cell receptor for the epitope. These events lead to T cell proliferation, lymphokine secretion, local inflammatory reactions, recruitment of additional immune cells to the site of antigen/T cell interaction, and activation of the B cell cascade, leading to the production of antibodies. One isotype of these antibodies, IgE, is fundamentally important to the development of allergic symptoms and its production is influenced early in the cascade of events at the level of the T helper cell, by the nature of the lymphokines secreted. A T cell epitope is the basic element, or smallest unit of recognition by a T cell receptor, where the epitope comprises amino acids essential to receptor recognition. Amino acid sequences which mimic those of the T cell epitopes and which modify the allergic response to protein allergens are within the scope of this invention.

Screening peptides for those which retain a Can f I or Can f II activity as described herein can be accomplished using one or more of several different assays. For example, in vitro, Can f I or Can f II T cell stimulatory activity is assayed by contacting a peptide known or suspected of having a Can f I or Can f II activity with an antigen presenting cell which presents appropriate MHC molecules in a T cell culture. Presentation of a peptide having a Can f I or Can f II activity in association with appropriate MHC molecules to T cells in conjunction with the necessary costimulation has the effect of transmitting a signal to the T cell that induces the production of increased levels of cytokines, particularly of interleukin-2 and interleukin-4. The culture supernatant can be obtained and assayed for interleukin-2 or other known cytokines. For example, any one of several conventional assays for interleukin-2 can be employed, such as the assay described in *Proc. Natl. Acad. Sci USA,* 86:1333 (1989) the pertinent portions of which are incorporated herein by reference. A kit for an assay for the production of interferon is also available from Genzyme Corporation (Cambridge, Mass.).

Alternatively, a common assay for T cell proliferation entails measuring tritiated thymidine incorporation. The proliferation of T cells can be measured in vitro by determining the amount of ³H-labeled thymidine incorporated into the replicating DNA of cultured cells. Therefore, the rate of DNA synthesis and, in turn, the rate of cell division can be quantified.

In one embodiment, peptides which have Can f I or Can f II T cell stimulating activity (i.e., the peptide comprises at least one T cell epitope) can be identified using an algorithm which predicts the presence of T cell epitopes in a protein sequence, such as the algorithm described by Hill et al., *Journal of Immunology*, 147:189–197 (1991). The algorithm of Hill et al. predicts the location of T cell epitopes in a protein by the presence of certain patterns within the sequence which are likely to bind MHC and therefore may contain T cell epitopes. Based on the Hill et al. algorithm, two 13 amino acid peptides (discussed in Example 10) have been identified and produced synthetically. Such peptides were tested for T cell activity as described above (e.g., by measuring cellular uptake of tritiated thymidine). Specifically, in Example 10, human T cell stimulating activity was tested by culturing T cells obtained from an individual sensitive to Can f I (i.e., an individual who has an IgE mediated immune response to Can f I) with a peptide derived from Can f I and proliferation of T cells in response to the peptide was determined, e.g., by measuring cellular uptake of tritiated thymidine. Stimulation indices for responses by T cells to peptides were calculated as the maximum CPM in response to a peptide divided by the control CPM. A stimulation index (S.I.) equal to or greater than two times the background level was considered "positive". Positive results were used to calculate the mean stimulation index for each peptide for the group of patients tested (See FIG. 25). Preferred peptides of this invention comprise at least one T cell epitope and have a mean T cell stimulation index of greater than or equal to 2.0. A peptide having a mean T cell stimulation index of greater than or equal to 2.0 in a significant number of dog dander allergen sensitive patients tested is considered useful as a therapeutic agent. Preferred peptides have a mean T cell stimulation index of at least 2.5, more preferably at least 3.0, more preferably at least 3.5, more preferably at least 4.0, more preferably at least 5.0 and most preferably at least about 6. For example, peptides having a Can f I activity and having a mean T cell stimulation index of at least 5, as indicated by data shown in FIG. 25, include Construct 1 (SEQ ID NO: 105), Construct 2 (SEQ ID NO: 106), and Construct 3 (SEQ ID NO:107). T cell epitopes can also be predicted and determined as described above for peptides derived from Can f II.

Figure 10:
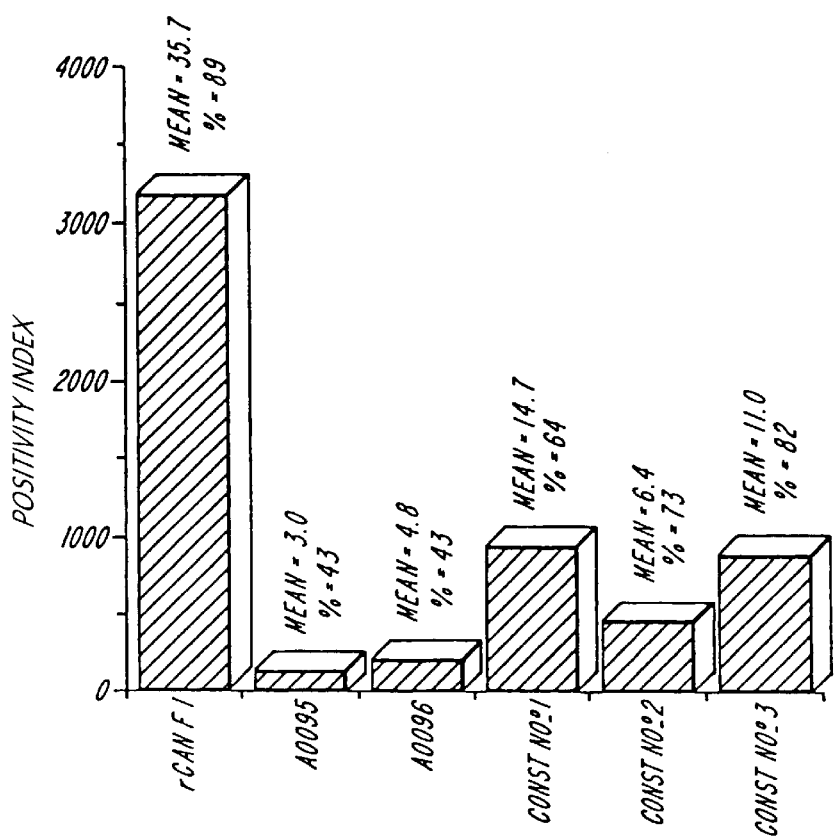
FIG. 10 is a graphic representation depicting the response of T cell lines from patients primed in vitro with recombinant Can f I (rCan f I) and analyzed for response to rCan f I and various peptides derived from Can f I by positivity index (% of patients who positively responded multiplied by the mean stimulation index).
Figure 25:
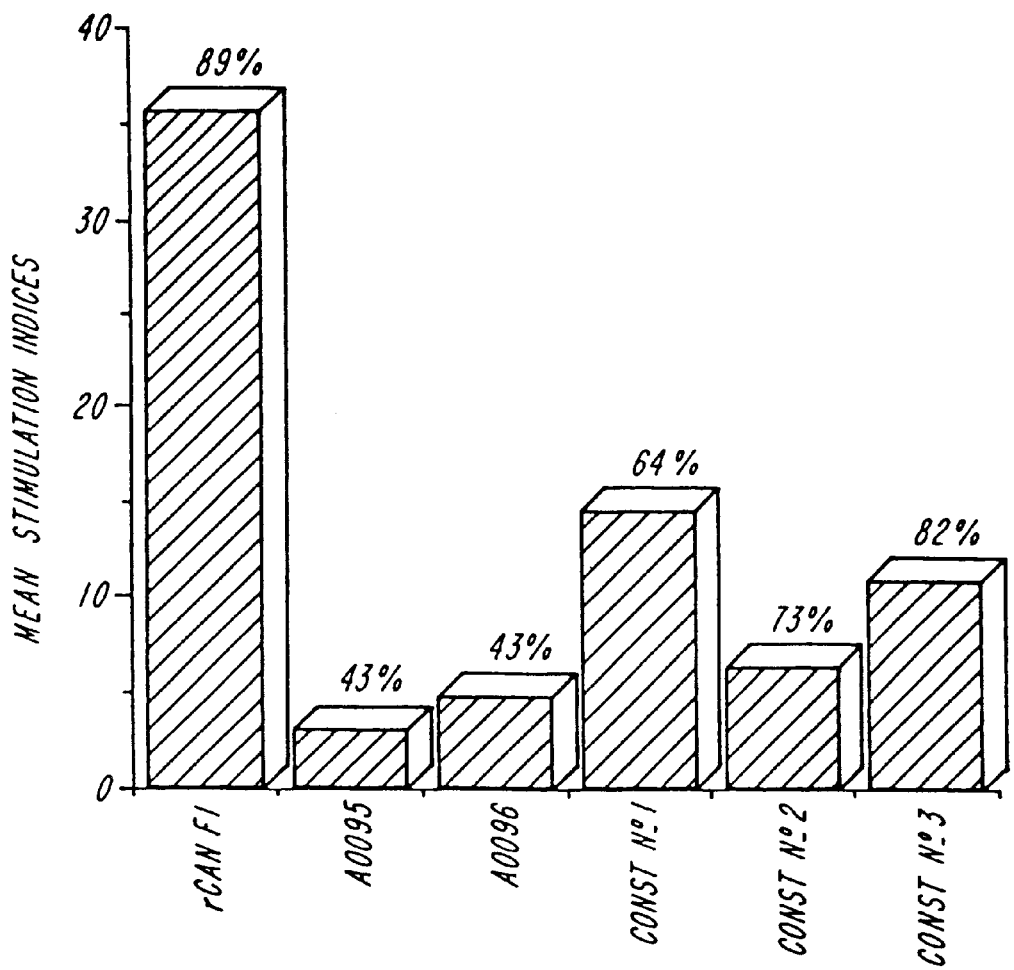
FIG. 25 is a graphic representation depicting the response of T cell lines from 12 patients primed in vitro with recombinant Can f I (rCan f I) and analyzed for response to rCan f I and various peptides derived from Can f I by mean stimulation index for the group of patients with positive responses to the peptides.

In addition, preferred peptides have a positivity index (P.I.) of at least about 60, more preferably about 100, more preferably at least about 200 and most preferably at least about 300. The positivity index for a peptide is determined by multiplying the mean T cell stimulation index by the percent of individuals, in a population of individuals sensitive to dog dander allergens (e.g., preferably a population of at least 12 individuals, more preferably a population of at least 30 individuals or more), who have a T cell stimulation index to such peptide of at least 2.0. Thus, the positivity index represents both the strength of a T cell response to a peptide (S.I.) and the frequency of a T cell response to a peptide in a population of individuals sensitive to dog dander allergens. In FIG. 10, the bar represents the positivity index and the percent of individuals tested who have a T cell stimulation index of at least 2.0 to various peptides derived from Can f I. For example, as shown in FIG. 25, Peptide A0095 has a mean S.I. of 3.0 and 43% of positive responses in the group of individuals tested resulting in a positivity index of 129.

In order to determine precise T cell epitopes by, for example, fine mapping techniques, a peptide having Can f I or Can f II T cell stimulating activity and thus comprising at least one T cell epitope as determined by T cell biology techniques is modified by addition or deletion of amino acid residues at either the amino or carboxy terminus of the peptide and tested to determine a change in T cell reactivity to the modified peptide. Following this technique, peptides are selected and produced recombinantly or synthetically. Peptides are selected based on various factors, including the strength of the T cell response to the peptide (e.g., stimulation index), the frequency of the T cell response to the peptide in a population of individuals sensitive to dog dander allergens, and the potential cross-reactivity of the peptide with other dog dander allergens. The physical and chemical properties of these selected peptides (e.g., solubility, stability) are examined to determine whether the peptides are suitable for use in therapeutic compositions or whether the peptides require modification as described herein. The ability of the selected peptides or selected modified peptides to stimulate human T cells (e.g., induce proliferation, lymphokine secretion) is then determined as described herein.

In another embodiment, a peptide having a Can f I or Can f II activity is screened for the ability to induce T cell non-responsiveness. The ability of a peptide known to stimulate T cells (as determined by one or more of the above described assays), to inhibit or completely block the activity of purified native Can f I or Can f II or portion thereof and induce a state of non-responsiveness can be determined using subsequent attempts at stimulation of the T cells with antigen presenting cells that present native Can f I or Can f II or peptide having a Can f I or Can f II activity following exposure to the peptide, having a Can f I or Can f II activity. If the T cells are unresponsive to the subsequent activation attempts, as determined by interleukin-2 synthesis and/or T cell proliferation, a state of non-responsiveness has been induced. See, e.g., Gimmi et al., (1993) *Proc. Natl. Acad. Sci USA*, 90:6586–6590; and Schwartz (1990) *Science*, 248:1349–1356, for assay systems that can be used as the basis for an assay in accordance with the present invention.

In yet another embodiment, peptides having a Can f I or Can f II activity are identified by IgE binding activity. For therapeutic purposes, peptides of the invention preferably do not bind IgE specific for a dog dander allergen, or bind such IgE to a substantially lesser extent than the corresponding purified native dog dander allergen binds such IgE. Reduced IgE binding activity refers to IgE binding activity that is less than that of purified native Can f I or Can f II protein. If a peptide having a Can f I or Can f II activity is to be used as a diagnostic reagent, it is not necessary that the peptide have reduced IgE binding activity compared to the native Can f I or Can f II allergen. IgE binding activity of peptides can be determined by, for example, an enzyme-linked immunosorbent assay (ELISA) using, for example, sera obtained from a subject, (i.e., an allergic subject) that has been previously exposed to the native Can f I or Can f II allergen. Briefly, the peptide suspected of having a Can f I or Can f II activity is coated onto wells of a microtiter plate. After washing and blocking the wells, antibody solution consisting of the plasma of an allergic subject who has been exposed to a peptide suspected of having a Can f I or Can f II activity is incubated in the wells. The plasma is generally depleted of IgG before incubation. A labeled secondary antibody is added to the wells and incubated. The amount of IgE binding is then quantified and compared to the amount of IgE bound by a purified, native Can f I or Can f II protein. Alternatively, the IgE binding activity of a peptide can be determined by Western blot analysis. For example, a peptide suspected of having a Can f I or Can f II activity is run on a polyacrylamide gel using SDS-PAGE. The peptide is then transferred to nitrocellulose and subsequently incubated with sera from an allergic subject. After incubation with a labeled secondary antibody, the amount of IgE bound is then determined and quantified.

Another assay which can be used to determine the IgE binding activity of a peptide is a competition ELISA assay. Briefly, an IgE antibody pool is generated by combining plasma from dog dander allergic subjects that have been shown by direct ELISA to have IgE reactive with native Can f I or Can f II. This pool is used in ELISA competition assays to compare IgE binding of native Can f I or Can f II and a peptide suspected of having a Can f I or Can f II activity. IgE binding for the native Can f I or Can f II protein and a peptide suspected of having a Can f I or Can f II activity is determined and quantified.

If a peptide having an activity of Can f I or Can f II binds IgE, and is to be used as a therapeutic agent, it is preferable that such binding does not result in the release of mediators (e.g., histamines) from mast cells or basophils. To determine whether a peptide which binds IgE results in the release of mediators, a histamine release assay can be performed using standard reagents and protocols obtained, for example, from Amac, Inc. (Westbrook, Me.). Briefly, a buffered solution of a peptide suspected of having a Can f I or Can f II activity is combined with an equal volume of whole heparinized blood from an allergic subject. After mixing and incubation, the cells are pelleted and the supernatants are processed and analyzed using a radioimmunoassay to determine the amount of histamine released.

Peptides having an activity of Can f I or Can f II which are to be used as therapeutic agents are preferably tested in mammalian models of dog dander atopy, such as the mouse model disclosed in Tamura et al., (1986) *Microbiol. Immunol.*, 30:883–896, or in U.S. Pat. No. 4,939,239, or in the primate model disclosed in Chiba et al., (1990) *Int. Arch. Allergy Immunol.*, 93:83–88. Initial screening for IgE binding to a peptide having an activity of Can f I or Can f II may be performed by scratch tests or intradermal skin tests on laboratory animals or human volunteers, or in in vitro systems such as RAST, RAST inhibition, ELISA assay, RIA (radioimmunoassay), or a histamine release assay, as described above.

It is possible to modify the structure of a peptide having an activity of Can f I or Can f II for such purposes as increasing solubility, enhancing therapeutic or prophylactic efficacy, or stability (e.g., shelf life ex vivo and resistance to proteolytic degradation in vivo). Such modified peptides are considered functional equivalents of peptides having an activity of Can f I or Can f II as defined herein. A modified peptide can be produced in which the amino acid sequence has been altered, such as by amino acid substitution, deletion, or addition, to modify immunogenicity and/or reduce allergenicity, or to which a component has been added for the same purpose.

For example, a peptide having an activity of Can f I or Can f II can be modified so that it maintains the ability to induce T cell non-responsiveness and bind MHC proteins without the ability to induce a strong proliferative response or possibly, any proliferative response when administered in immunogenic form. In this instance, critical binding residues for T cell receptor function can be determined using known techniques (e.g., substitution of each residue and determination of the presence or absence of T cell reactivity). Those residues shown to be essential to interact with the T cell receptor can be modified by replacing the essential amino acid with another, preferably similar amino acid residue (a conservative substitution) whose presence is shown to enhance, diminish but not eliminate, or not affect T cell reactivity. In addition, those amino acid residues which are not essential for T cell receptor interaction can be modified by being replaced by another amino acid whose incorporation may enhance, diminish but not eliminate, or not affect T cell reactivity, but does not eliminate binding to relevant MHC.

Additionally, a peptide having an activity of Can f I or Can f II can be modified by replacing an amino acid shown to be essential to interact with the MHC protein complex with another, preferably similar amino acid residue (conservative substitution) whose presence is shown to enhance, diminish but not eliminate, or not affect T cell activity. In addition, amino acid residues which are not essential for interaction with the MHC protein complex but which still bind the MHC protein complex can be modified by being replaced by another amino acid whose incorporation may enhance, not affect, or diminish but not eliminate T cell reactivity. Preferred amino acid substitutions for non-essential amino acids include, but are not limited to substitutions with alanine, glutamic acid, or a methyl amino acid.

Another example of modification of a peptide having an activity of Can f I or Can f II is substitution of cysteine residues preferably with alanine, serine, threonine, leucine or glutamic acid residues to minimize dimerization via disulfide linkages. In addition, amino acid side chains of fragments of the protein of the invention can be chemically modified. Another modification is cyclization of the peptide.

In order to enhance stability and/or reactivity, a peptide having an activity of Can f I or Can f II can be modified to incorporate one or more polymorphisms in the amino acid sequence of the protein allergen resulting from any natural allelic variation. Additionally, D-amino acids, non-natural amino acids, or non-amino acid analogs can be substituted or added to produce a modified protein within the scope of this invention. Furthermore, a peptide having an activity of Can f I or Can f II can be modified using polyethylene glycol (PEG) according to the method of A. Sehon and co-workers (Wie et al., supra) to produce a protein conjugated with PEG. In addition, PEG can be added during chemical synthesis of the protein. Other modifications of a peptide having an activity of Can f I or Can f II include reduction/alkylation (Tarr, *Methods of Protein Microcharacterization*, J. E. Silver ed., Humana Press, Clifton N.J. 155–194 (1986)); acylation (Tarr, supra); chemical coupling to an appropriate carrier (Mishell and Shiigi, eds, *Selected Methods in Cellular Immunology*, W H Freeman, San Francisco, Calif. (1980), U.S. Pat. No. 4,939,239; or mild formalin treatment (Marsh, (1971) *Int. Arch. of Allergy and Appl. Immunol.*, 41:199–215).

To facilitate purification and potentially increase solubility of a peptide having an activity of Can f I or Can f II, it is possible to add an amino acid fusion moiety to the peptide backbone. For example, hexa-histidine can be added to the protein for purification by immobilized metal ion affinity chromatography (Hochuli, E. et al., (1988) *Bio/Technology*, 6:1321–1325). In addition, to facilitate isolation of peptides free of irrelevant sequences, specific endoprotease cleavage sites can be introduced between the sequences of the fusion moiety and the peptide. In order to successfully desensitize a subject to Can f I or Can f II protein or related allergen, it may be necessary to increase the solubility of the protein by adding functional groups to the protein, or by omitting hydrophobic regions of the protein.

To potentially aid proper antigen processing of T cell epitopes within Can f I or Can f II, canonical protease sensitive sites can be engineered between regions, each comprising at least one T cell epitope via recombinant or synthetic methods. For example, charged amino acid pairs, such as KK or RR, can be introduced between regions within a protein or fragment during recombinant construction thereof. The resulting peptide can be rendered sensitive to cleavage by cathepsin and/or other trypsin-like enzymes which would generate portions of the protein containing one or more T cell epitopes. In addition, such charged amino acid residues can result in an increase in the solubility of the peptide.

Site-directed mutagenesis of a nucleic acid encoding a peptide having an activity of Can f I or Can f II can be used to modify the structure of the peptide by methods known in the art. Such methods may, among others, include polymerase chain reaction (PCR) with oligonucleotide primers bearing one or more mutations (Ho et al., (1989) *Gene*, 77:51–59) or total synthesis of mutated genes (Hostomsky, Z. et al., (1989) *Biochem. Biophys. Res. Comm*, 161:1056–1063). To enhance recombinant protein expression, the aforementioned methods can be applied to change the codons present in the cDNA sequence of the invention to those preferentially utilized by the host cell in which the recombinant protein is being expressed (Wada et al., supra).

Another aspect of the invention pertains to an antibody specifically reactive with a peptide having an activity of Can f I or Can f II. The antibodies of this invention can be used to standardize allergen extracts or to isolate the naturally-occurring or native form of Can f I or Can f II. For example, by using peptides having an activity of Can f I or Can f II based on the cDNA sequence of Can f I or Can f II, anti-protein/anti-peptide antisera or monoclonal antibodies can be made using standard methods. A mammal such as a mouse, a hamster or rabbit can be immunized with an immunogenic form of the peptide (e.g., Can f I or Can f II protein or an antigenic fragment which is capable of eliciting an antibody response). Techniques for conferring immunogenicity on a protein or peptide include conjugation to carriers or other techniques well known in the art. A peptide having an activity of Can f I or Can f II can be administered in the presence of adjuvant. The progress of immunization can be monitored by detection of antibody titers in plasma or serum. Standard ELISA or other immunoassay can be used with the immunogen as antigen to assess the levels of antibodies.

Following immunization, anti-Can f I or anti-Can f II antisera can be obtained and, if desired, polyclonal anti-Can f I or anti-Can f II antibodies isolated from the serum. To produce monoclonal antibodies, antibody producing cells (lymphocytes) can be harvested from an immunized animal and fused by standard somatic cell fusion procedures with immortalizing cells such as myeloma cells to yield hybridoma cells. Such techniques are well known in the art, for example the hybridoma technique originally developed by Kohler and Milstein, (1975) *Nature*, 256:495–497) as well as other techniques such as the human B cell hybridoma technique (Kozbar et al., (1983) *Immunology Today*, 4:72) and the EBV-hybridoma technique to produce human monoclonal antibodies (Cole et al., (1985) *Monoclonal Antibodies and Cancer Therapy*, Alan R. Liss, Inc. pp. 77–96). Hybridoma cells can be screened immunochemically for production of antibodies specifically reactive with a peptide having an activity of Can f I or Can f II and the monoclonal antibodies isolated.

The term antibody as used herein is intended to include fragments thereof which are also specifically reactive with the peptide having an activity of Can f I or Can f II. Antibodies can be fragmented using conventional techniques and the fragments screened for utility in the same manner as described above for whole antibodies. For example, F(ab')$_2$ fragments can be generated by treating antibody with pepsin. The resulting F(ab')$_2$ fragment can be treated to reduce disulfide bridges to produce Fab' fragments. The antibody of the present invention is further intended to include bispecific and chimeric molecules having an anti-Can f I or anti-Can f II portion.

Another aspect of this invention provides T cell clones and soluble T cell receptors specifically reactive with a peptide having an activity of Can f I or Can f II. Monoclonal T cell populations (i.e., T cells genetically identical to one another and expressing identical T cell receptors) can be derived from an individual sensitive to Can f I or Can f II, followed by repetitive in vitro stimulation with a Can f I or Can f II protein or peptide having an activity of Can f I or Can f II in the presence of MHC-matched antigen-presenting cells. Single Can f I or Can f II MHC responsive cells can then be cloned by limiting dilution and permanent lines expanded and maintained by periodic in vitro restimulation. Alternatively, Can f I or Can f II specific T-T hybridomas can be produced by a technique similar to B cell hybridoma production. For example, a mammal, such as a mouse, is immunized with a peptide having an activity of Can f I or Can f II, T cells are then purified and fused with an autonomously growing T cell tumor line. From the resulting hybridomas, cells responding to a peptide having an activity of Can f I or Can f II are selected and cloned. Procedures from propagating monoclonal T cell populations are described in *Cellular and Molecular Immunology* (Abul K. Abbas et al. ed.), W. B. Saunders Company, Philadelphia, Pa. (1991) page 139. Soluble T cell receptors specifically reactive with a peptide having an activity of Can f I or Can f II can be obtained by immunoprecipitation using an antibody against the T cell receptor as described in *Immunology: A Synthesis* (Second Edition), Edward S. Golub et al., ed., Sinauer Associates, Inc., Sunderland, Mass. (1991) pages 366–269.

T cell clones specifically reactive with a peptide having an activity of Can f I or Can f II can be used to isolate and molecularly clone the gene encoding the relevant T cell receptor. In addition, a soluble T cell receptor specifically reactive with a peptide having an activity of Can f I or Can f II can be used to interfere with or inhibit antigen-dependent activation of the relevant T cell subpopulation, for example, by administration to an individual sensitive to Can f I or Can f II. Antibodies specifically reactive with such a T cell receptor can be produced according to the techniques described herein. Such antibodies can be used to block or interfere with the T cell interaction with peptides presented by MHC.

Exposure of allergic subjects to peptides having an activity of Can f I or Can f II and which have T cell stimulating activity, may cause the appropriate T cell subpopulations to become non-responsive to the respective protein allergen (e.g., fail to stimulate an immune response upon such exposure). In addition, such administration may modify the lymphokine secretion profile as compared with exposure to the naturally-occurring protein allergen or portion thereof (e.g., result in a decrease of IL-4 and/or an increase in IL-2).

Furthermore, exposure to peptides having an activity of Can f I or Can f II which have T cell stimulating activity may influence T cell subpopulations which normally participate in the response to the allergen such that these T cells are drawn away from the site(s) of normal exposure to the allergen (e.g., nasal mucosa, skin, and lung) towards the site(s) of therapeutic administration of the protein or fragment derived therefrom. This redistribution of T cell subpopulations may ameliorate or reduce the ability of an individual's immune system to stimulate the usual immune response at the site of normal exposure to the allergen, resulting in a diminution in allergic symptoms.

A peptide having an activity of Can f I or Can f II when administered to a subject sensitive to dog dander allergens is capable of modifying the B cell response, T cell response, or both the B cell and the T cell response of the subject to the allergen. As used herein, modification of the allergic response of a subject to a dog dander allergen can be defined as non-responsiveness or diminution in symptoms to the allergen, as determined by standard clinical procedures (See e.g., Varney et al., (1990) *British Medical Journal,* 302:265–269), including diminution in dog dander induced asthmatic symptoms. As referred to herein, a diminution in symptoms includes any reduction in the allergic response of a subject to the allergen following a treatment regimen with a peptide of the invention. This diminution in symptoms may be determined subjectively (e.g., the patient feels more comfortable upon exposure to the allergen), or clinically, such as with a standard skin test.

Peptides or antibodies of the present invention can also be used for detecting and diagnosing sensitivity to Can f I or Can f II. For example, this could be done by combining blood or blood products obtained from a subject to be assessed for sensitivity with peptide having an activity of Can f I or Can f II, under conditions appropriate for binding of components in the blood (e.g., antibodies, T cells, B cells) with the peptide(s) and determining the extent to which such binding occurs. Other diagnostic methods for allergic diseases which the peptides or antibodies of the present invention can be used include radio-allergosorbent test (RAST), paper radioimmunosorbent test (PRIST), enzyme linked immunosorbent assay (ELISA), radioimmunoassays (RIA), immuno-radiometric assays (IRMA), luminescence immunoassays (LIA), histamine release assays and IgE immunoblots.

The present invention further provides methods of detecting and treating sensitivity in a subject to Can f I or Can f II. The presence in subjects of IgE specific for Can f I or Can f II and the ability of T cells of the subjects to respond to T cell epitopes of Can f I or Can f II can be determined by administering to the subject an Immediate Type Hypersensitivity test and/or a Delayed Type Hypersensitivity test (See e.g., *Immunology (*1985) Roitt, I. M., Brostoff, J., Male, D. K. (eds), C. V. Mosby Co., Gower Medical Publishing, London, N.Y., pp. 19.2–19.18; pp.22.1–22.10) utilizing a peptide having an activity of Can f I or Can f II, or a modified form of a peptide having an activity of Can f I or Can f II, each of which binds IgE specific for the allergen. The same subjects are administered a Delayed Type Hypersensitivity test prior to, simultaneously with, or subsequent to administration of the Immediate Type Hypersensitivity test. Of course, if the Immediate Type Hypersensitivity test is administered prior to the Delayed Type Hypersensitivity test, the Delayed Type Hypersensitivity test would be given to those subjects exhibiting a specific Immediate Type Hypersensitivity reaction. The Delayed Type Hypersensitivity test utilizes a peptide having an activity of Can f I or Can f II which has human T cell stimulating activity and which does not bind IgE specific for the allergen in a substantial percentage of the population of subjects sensitive to the allergen (e.g., at least about 75%). Those subjects found to have both a specific Immediate type Hypersensitivity reaction and a specific Delayed Type Hypersensitivity reaction are administered an amount of a composition suitable for pharmaceutical administration. The composition comprises the peptide having an activity of Can f I or Can f II as used in the Delayed Type Hypersensitivity test and a pharmaceutically acceptable carrier or diluent.

A peptide having an activity of Can f I or Can f II can be used in methods of diagnosing, treating, and preventing allergic reactions to a dog dander allergen or a cross-reactive protein allergen. Thus, the present invention provides compositions suitable for pharmaceutical administration comprising an amount of at least one peptide having an activity of Can f I or Can f II and a pharmaceutically acceptable carrier. Administration of the compositions of the present invention to a subject to be desensitized can be carried out using known procedures, at dosages and for periods of time effective to reduce sensitivity (i.e., reduce the allergic response) of the subject to a dog dander allergen. The term subject is intended to include living organisms in which an immune response can be elicited, e.g., mammals. Examples of subjects include humans, dogs, cats, mice, rats, and transgenic species thereof. An amount of at least one peptide having an activity of Can f I or Can f II necessary to achieve a therapeutic effect may vary according to factors such as the degree of sensitivity of the subject to dog dander, the age, sex, and weight of the subject, and the ability of a peptide having an activity of Can f I or Can f II to elicit an antigenic response in the subject. Dosage regima may be adjusted to provide the optimum therapeutic response. For example, several divided doses may be administered daily or the dose may be proportionally reduced as indicated by the exigencies of the therapeutic situation.

The active compound (i.e., a peptide having an activity of Can f I or Can f II) may be administered in a convenient manner such as by injection (subcutaneous, intravenous, etc.), oral administration, inhalation, transdermal application, or rectal administration. Depending on the route of administration, the active compound may be coated in a material to protect the compound from the action of enzymes, acids and other natural conditions which may inactivate the compound.

To administer a peptide having an activity of Can f I or Can f II by other than parenteral administration, it may be necessary to coat the peptide with, or co-administer the peptide with, a material to prevent its inactivation. For example, a peptide having an activity of Can f I or Can f II may be administered to an individual in an appropriate carrier, diluent or adjuvant, co-administered with enzyme inhibitors or in an appropriate carrier such as liposomes. Pharmaceutically acceptable diluents include saline and aqueous buffer solutions. Adjuvant is used in its broadest sense and includes any immune stimulating compound such as interferon. Adjuvants contemplated herein include resorcinols, non-ionic surfactants such as polyoxyethylene oleyl ether and n-hexadecyl polyethylene ether. Enzyme inhibitors include pancreatic trypsin inhibitor, diisopropylfluorophosphate (DEP) and trasylol. Liposomes include water-in-oil-in-water CGF emulsions as well as conventional liposomes (Strejan et al., (1984) *J. Neuroimmunol.,* 7:27). For purposes of inducing T cell nonresponsiveness, the composition is preferably administered in non-immunogenic form, e.g., one that does not contain adjuvant.

The active compound may also be administered parenterally or intraperitoneally. Dispersions can also be prepared in glycerol, liquid polyethylene glycols, and mixtures thereof and in oils. Under ordinary conditions of storage and use, these preparations may contain a preservative to prevent the growth of microorganisms.

Pharmaceutical compositions suitable for injectable use include sterile aqueous solutions (where water soluble) or dispersions and sterile powders for the extemporaneous preparation of sterile injectable solutions or dispersion. In all cases, the composition must be sterile and must be fluid to the extent that easy syringability exists. It must be stable under the conditions of manufacture and storage and must be preserved against the contaminating action of microorganisms such as bacteria and fungi. The carrier can be a solvent or dispersion medium containing, for example, water, ethanol, polyol (for example, glycerol, propylene glycol, and liquid polyetheylene glycol, and the like), suitable mixtures thereof, and vegetable oils. The proper fluidity can be maintained, for example, by the use of a coating such as lecithin, by the maintenance of the required particle size in the case of dispersion and by the use of surfactants. Prevention of the action of microorganisms can be achieved by various antibacterial and antifungal agents, for example, parabens, chlorobutanol, phenol, ascorbic acid, thimerosal, and the like. In many cases, it will be preferable to include isotonic agents, for example, sugars, polyalcohols such as mannitol, sorbitol, sodium chloride in the composition. Prolonged absorption of the injectable compositions can be brought about by including in the composition an agent which delays absorption, for example, aluminum monostearate and gelatin.

Sterile injectable solutions can be prepared by incorporating active compound (i.e., a peptide having an activity of Can f I or Can f II) in the required amount in an appropriate solvent with one or a combination of ingredients enumerated above, as required, followed by filtered sterilization. Generally, dispersions are prepared by incorporating the active compound into a sterile vehicle which contains a basic dispersion medium and the required other ingredients from those enumerated above. In the case of sterile powders for the preparation of sterile injectable solutions, the preferred methods of preparation are vacuum drying and freeze-drying which yields a powder of the active ingredient (i.e., at least one peptide having an activity of Can f I or Can f II) plus any additional desired ingredient from a previously sterile-filtered solution thereof.

When the peptide having an activity of Can f I or Can f II is suitably protected, as described above, the peptide may be orally administered, for example, with an inert diluent or an assimilable edible carrier. The peptide and other ingredients may also be enclosed in a hard or soft shell gelatin capsule, compressed into tablets, or incorporated directly into the individual's diet. For oral therapeutic administration, the active compound may be incorporated with excipients and used in the form of ingestible tablets, buccal tablets, troches, capsules, elixirs, suspensions, syrups, wafers, and the like. The percentage of the compositions and preparations may, of course, be varied and may conveniently be between about 5 to about 80% of the weight of the unit. The amount of active compound in such therapeutically useful compositions is such that a suitable dosage will be obtained.

As used herein "pharmaceutically acceptable carrier" includes any and all solvents, dispersion media, coatings, antibacterial and antifungal agents, isotonic and absorption delaying agents, and the like. The use of such media and agents for pharmaceutically active substances is well known in the art. Except insofar as any conventional media or agent is incompatible with the active compound, use thereof in the therapeutic compositions is contemplated. Supplementary active compounds can also be incorporated into the compositions.

It is especially advantageous to formulate parenteral compositions in dosage unit form for ease of administration and uniformity of dosage. Dosage unit form as used herein refers to physically discrete units suited as unitary dosages for the mammalian subjects to be treated; each unit containing a predetermined quantity of active compound calculated to produce the desired therapeutic effect in association with the required pharmaceutical carrier. The specification for the dosage unit forms of the invention are dictated by and directly dependent on (a) the unique characteristics of the active compound and the particular therapeutic effect to be achieved, and (b) the limitations inherent in the art of compounding such an active compound for the treatment of sensitivity in subjects.

The present invention also provides a composition comprising at least two peptides having an activity of Can f I or Can f II (e.g., a physical mixture of at least two peptides), each having T cell stimulating activity. For example, at least two peptides each having as activity of Can f I can be combined or at least two peptides each having an activity of Can f II can be combined, or at least one peptide having an activity of Can f I and at least one peptide having an activity of Can f II can be combined and administered. Alternatively, a peptide having at least two regions, each having T cell stimulating activity (i.e., each region comprising at least one T cell epitope) can be administered to an allergic subject. Such a peptide can have at least two regions derived from the same allergen, Can f I or Can f II, or a combination of Can f I and Can f II. A composition of two peptides or a peptide having at least two regions can be administered to a subject in the form of a composition with a pharmaceutically acceptable carrier as hereinbefore described. An amount of one or more of such compositions can be administered simultaneously or sequentially to a subject sensitive to a dog dander allergen to treat such sensitivity.

The cDNA (or the mRNA which served as a template during reverse transcription) encoding a peptide having an activity of Can f I or Can f II can be used to identify similar nucleic acid sequences in any variety or type of animal and, thus, to molecularly clone genes which have sufficient sequence homology to hybridize to the cDNA encoding a peptide having an activity of Can f I or Can f II. Thus, the present invention includes not only peptides having an activity of Can f I or Can f II, but also other proteins which may be allergens encoded by DNA which hybridizes to DNA of the present invention.

Isolated peptides that are immunologically related to Can f I or Can f II, such as by antibody cross-reactivity or T cell cross-reactivity, other than those already identified, are within the scope of the invention. Such peptides bind antibodies specific for the protein and peptides of the invention, or stimulate T cells specific for the protein and peptides of this invention.

A peptide having an activity of Can f I or Can f II (i.e., Can f I or Can f II produced recombinantly or by chemical synthesis) is free of all other dog dander proteins and, thus, is useful in the standardization of allergen extracts which are key reagents for the diagnosis and treatment of dog dander hypersensitivity. In addition, such a peptide is of a consistent, well-defined composition and biological activity for use in preparations which can be administered for therapeutic purposes (e.g., to modify the allergic response of a subject sensitive to dog dander). Such peptides can also be used to study the mechanism of immunotherapy of *Canis familiaris* allergy and to design modified derivatives or analogs useful in immunotherapy.

Work by others has shown that high doses of allergen extracts generally produce the best results during immunotherapy (i.e., best symptom relief). However, many subjects are unable to tolerate large doses of such extracts due to systemic reactions elicited by the allergens and other components within these preparations. A peptide having an activity of Can f I or Can f II of the invention has the advantage of being free of all other dander protein. Thus, such a peptide can be administered for therapeutic purposes.

It is now also possible to design an agent or a drug capable of blocking or inhibiting the ability of a dog dander allergen to induce an allergic reaction in sensitive subjects. Such agents could be designed, for example, in such a manner that they would bind to relevant anti-Can f I or anti-Can f II IgE molecules, thus preventing IgE-allergen binding, and subsequent mast cell/basophil degranulation. Alternatively, such agents could bind to cellular components of the immune system, resulting in suppression or desensitization of the allergic responses to dog dander allergens. A non-restrictive example of this is the use of peptides including B or T cell epitopes of Can f I or Can f II, or modifications thereof, based on the cDNA protein structure of Can f I or Can f II to suppress the allergic response to a dog dander allergen. This could be carried out by defining the structures of fragments encoding B and T cell epitopes which affect B and T cell function in in vitro studies with blood components from subjects sensitive to dog dander.

The invention is further illustrated by the following examples which should not be construed as further limiting the subject invention. The contents of all references and published patent applications cited throughout this application are hereby incorporated by reference.

EXAMPLE 1

Protein Sequence Analysis of Purified Can f I

Affinity purified Can f I protein was obtained from Dr. Aalberse (de Groot, H. et al., supra). An Applied Biosystems Model 477A gas phase sequencer with on-line phynylthiohydantoin (HTH) amino acid analysis (Model 120A) was used to sequence the purified Can f I protein. A modification of the extraction program, multiple butylchloride extractions, was used to improve the amino acid recovery. O-phthaladehyde (OPA) was used in blocking of primary amines when proline was located at the amino terminus. Brauer, A. W., et al., (1984) *Anal. Biochemistry*, 137:134, 142. In situ alkylation was performed by using the non-nucleophilic reductant, tributylphosphine with concomitant alkylation by 4-vinyl pyridine in ethylmorpholine buffer. Andrews, P. C. and Dixon, J. E., (1987) *Anal. Biochemistry*, 161:524–528.

Using this methodology, the sequence of the N-terminus of the Can f I protein was determined, contrary to previous reports that the N-terminus is blocked (Schou, C. et al., supra). The N-terminal sequence of 65 amino acid residues which was identified through multiple N-terminal sequence analysis in conjunction with OPA blocking of contaminating signal represents a novel protein sequence (FIG. 5). The Can f I protein sequence was confirmed and expanded by sequence analysis of CNBr cleaved peptides. In situ CNBr digestion of Can f I on the sequence glass filter disk provided additional protein sequence information. Simpson, R. J. and Nice, E. C., (1984) *Biochem. International*, 8:787–791. Prior to the in situ CNBr cleavage, forty-four cycles of amino acid sequencing were performed and then the protein sample was treated with OPA to block all amino groups. After five hours of in situ CNBr digestion, three major sequences were identified corresponding to the sequences after Met46, Met30 and an unknown Met, later shown to be Met103. An additional OPA block after cycle 18 (before Pro65) extended the sequence to Asp86. Sequence analysis of CNBr peptide fragments isolated by HPLC (Applied Biosystem, Inc., Model 130, C8 Column) further extended the N-terminal sequence to ninety-four amino acid residues. In situ CNBr cleavage in conjunction with OPA blocking also identified a 39 amino acid residue peptide (residues 104–142). A potential N-glycosylation site was found in the cDNA deduced amino acid sequence, Asn54-Ile55-Thr56. The protein sequence analysis identified the Ile55 and Thr56 of Can f I, however, nothing could be identified at the position 54. This suggests that post-translation modification occurs at Asn54 of Can f I and the modification is stable to the trifluoroacetic acid treatment during protein sequencing.

EXAMPLE 2

Extraction of mRNA From Canine Parotid Glands and Cloning of Can f I

A pair of fresh parotid glands from a single outbred dog were obtained from the Tufts University School of Veterinary Medicine (Worcester, Mass.) and, washed in phosphate buffered saline, and immediately frozen on dry ice. RNA was extracted essentially as described in the literature (Chirgwin, J. M. et al., (1979) *Biochemistry*, 18:5294–5299.). One gland was pulverized to a powder with a mortar and pestle frozen in liquid N2, and suspended in 25 ml of GTC buffer (50% w/v guanidine thiocynate, 0.5% w/v Na lauryl sarcosine, 0.7% v/v β-mercaptoethanol, 0.1% v/v Sigma Antifoam A, 25 mM Na citrate, pH 7.0) and vortexed until dissolved. Genomic DNA present in the solution was sheared by forcing the solution through a 16 gauge needle until the viscosity of the solution no longer decreased. The sheared solution was centrifuged at 3 K rpm for 5 minutes at room temperature. The supernatant was then sheared further through a 23 gauge needle until its viscosity no longer decreased, and cleared by centrifugation at 5 K rpm for 5 minutes at room temperature. The solution was layered onto a CsCl cushion (5.7 M CsCl, 10 mM EDTA pH 7.5) and ultracentrifuged in a Beckman SW 41 Ti rotor at 35 K rpm for 16 hours at 20° C. The supernatant was discarded and the RNA pellet washed in 70% EtOH then resuspended in 0.3 M NaOAc, 10 mM EDTA, 0.1% SDS. Two volumes of absolute EtOH were added, and precipitation carried out on dry ice. RNA was pelleted by centrifugation, 70% EtOH washed, and resuspended in TES (10 mM Tris, 1 mM EDTA, 0.1% SDS). The final yield was ~1.8 mg.

Single strand total dog parotid gland cDNA was synthesized using the above RNA preparation as a template in reverse transcription. 4 μg of total RNA were EtOH precipitated (using glycogen as carrier: molecular biology grade Boerhinger Manheim), 70% EtOH washed, and resuspended in 10 μl of dH2O. Oligo dT(12–18) was added to 50 μg/ml and the RNA denatured at 70° C. for 5 minutes. The reaction was quick chilled on ice and 1 μl (40 units) of RNAsin (Promega) was added as a prophylactic against contaminating RNases. The components from the BRL Superscript™ Reverse Transcriptase Kit were added as follows: 4 μl 5×buffer, 2 µl 0.1 M DTT, 1 µl 10 mM dNTP mix. After warming the reaction to 37° C., 1 µl (200 units) of Superscript™ Reverse Transcriptase was added, and the reaction allowed to proceed for one hour at 37° C. Reverse transcription was terminated by incubation at 70° C. for 15 minutes, and the reaction stored at −20° C.

Initially the MOPAC (mixed oligonucleotides primed amplification of cDNA) technique of PCR amplification (Lee, C. C. et al., (1988) *Science,* 239:1288–1291) was used to obtain a partial cDNA of Can f I encoding amino acids 14 to 29 of the mature protein. Using dog parotid cDNA as a template with degenerate primer pairs (synthesized on an Applied Biosystems 392) based on residues 9 to 15 (SEQ ID NO:3) [FIG. 1, S1A (SEQ ID NO:4) or S1B (SEQ ID NO:5)] and 30 to 37 (SEQ ID NO:10) [Figure 1, AS2A (SEQ ID NO: 11) or AS2B (SEQ ID NO: 12)] of mature Can f I, a DNA fragment of the predicted size (~3×28 amino acids, or 84 bp) could be amplified using a PCR kit (GeneAmp kit, Perkin Elmer Cetus, Norwalk, Conn.) in conjunction with the following program in an MJ Research Minicycler: 40 ×(92° C. 30 seconds/55° C. 1 minutes/75° C. 1 minutes). The primer pair 5' S1B/3' AS2B amplified the predicted fragment with the greatest efficiency, inferring that in both coding regions, the leucine residue was encoded by CTX rather than TT(A or G). As a test of its authenticity, the amplified fragment hybridized on a Southern blot to an internal degenerate oligonucleotide probe Dog probe 1 (SEQ ID NO:7), [based on Can f I residues 17 to 24, (SEQ ID NO:6)] that had been end labeled with γ-32P ATP using T4 polynucleotide kinase. After subcloning of the amplified fragment into Bluescript KS plasmid vector (Stratagene, San Diego, Calif.), it was sequenced using a Sanger dideoxy termination kit (USB Cleveland, Ohio) and shown to correctly encode residues 16 to 29 of mature Can f I.

Similarly, when amino acid sequence analysis of purified Can f I yielded sequence information extending to residue 94 of the mature protein, new primer pairs were used in MOPAC PCR amplification of an extended partial Can f I cDNA (residues 14 to 87). The 5' or sense primers SA (residues 14 to 20) and SB (residues 21 to 27) were a nested pair based on the known Can f I partial cDNA sequence, while the 3' or antisense primers, AS3A (SEQ ID NO:13) (FIG. 1) and AS3B (SEQ ID NO:14) (FIG. 1) were degenerate oligonucleotides based on residues 88 to 94. In sequential rounds of PCR (1/100th of the first reaction was used as template for the second reaction) using conditions described above in a pair of successive reactions using nested 5' sense oligos in conjunction with a single 3' antisense degenerate primer, a DNA fragment of the predicted size (~3×80 amino acids, or 240 bp) could be amplified. Degenerate 3' antisense oligo AS3B was more efficient in collaborating with the successive pairs of 5' sense oligos to amplify the partial internal Can f I cDNA than oligo AS3A, again suggesting that the leucine residue was encoded by CTX rather than TT(A or G). The 240 bp DNA fragment was subcloned into Bluescript KS plasmid vector and sequenced as described above. It too proved to be an authentic Can f I cDNA. The missing residue in the amino acid sequence of Can f I at residue 54 was determined to be an asparagine on the grounds that: 1) no amino acid signal was found at residue 54 during protein sequence analysis; and 2) the asparagine residue resides within a consensus sequence for N-linked glycosylation (N54 I55 T56). These data strongly suggest that the N54 residue is modified by N-linked glycosylation.

To obtain the 3' portion of the Can f I cDNA, the RACE (Rapid Amplification of cDNA ends) PCR protocol was employed (Frohman, M. A. et al., (1988) *Proc. Natl. Acad. Sci.,* 85:8998–9002). First strand cDNA synthesis from total dog parotid RNA was carried out as described above, except that the JM3 oligonucleotide was substituted for oligo dT as the primer in the reaction. The JM3 primer (SEQ ID NO:22) has an arbitrary tract of ~40 nucleotides encoded 5' of an oligo dT tract (FIG. 2). Hence, upon priming of poly A+RNA to make cDNA, this known nucleotide tag is covalently linked to the 5' end of the nascent cDNA transcripts. Using nested 5' primers, SD (residues 73–79 (SEQ ID NO: 15)) and SE (residues 80–86 (SEQ ID NO:17)), based on known Can f I cDNA sequence from MOPAC PCR analysis and nested primers based on the known JM3 primer sequence (JM3-1 (SEQ ID NO:23) and JM3-3 Bam (SEQ ID NO:24)) in PCR amplification as above (except the PCR program was 40×[92° C. 30 seconds/60° C. 1 minutes/75° C. 1 minutes]), a DNA fragment ~500 bp in length was amplified. When probed against a kinase labeled degenerate oligonucleotide, Dog Probe 2 (SEQ ID NO:9) [residues 88 to 94 of mature Can f I (SEQ ID NO:8)], this band proved positive for hybridization. Upon subcloning into plasmid vector and DNA sequence analysis, three different partial 3° Can f I cDNAs were identified: Can f I (SEQ ID NO:61), 2Can f I (SEQ ID NO:62), and 3Can f I (SEQ ID NO:63), each as shown in FIG. 9. 2Can f I had a sequence that encoded a methionine residue followed by an asparagine-proline pair. These landmark residues for protein sequence analysis predicted: 1) a CNBr fragment with the NH2 terminal sequence MAKLLGRDPEQ . . . (SEQ ID NO:64); 2) an acid sensitive cleavage site at the DP pair; and 3) a proline residue which should prove refractory to OPA treatment and yield amino acid sequence data where all other NH2 termini would be blocked by the treatment. Indeed, further protein sequence analysis of purified Can f I did identify a CNBr fragment that in conjunction with OPA blockage at the internal proline residue had the sequence (M)AKLLGRDPEQSQEALEDF()EFS() AKGLNQEILELAQS(E)T (SEQ ID NO:65). Acid cleavage of the purified protein yielded a peptide with the sequence (D)PEQS(E)EA (SEQ ID NO:66). These complimentary data from protein sequence analysis and partial cDNA cloning of Can f I indicated that the authentic 3' end of the Can f I cDNA may not have been isolated.

Comparison of the amino acid sequence data from sequencing purified Can f I and those encoded by the partial cDNAs 2Can f I and 3Can f I inferred the origin of the multiple species of 3' cDNAs may have been alternative splicing of the nascent Can f I transcript (note how in partial cDNA 3Can f I residues from the NH2 terminus of the CNBr fragment are found linked to the fragment's COOH terminal residues without the intervening residues). In contrast to this hypothesis of multiple cDNAs originating at the level of alternative splicing, the above PCR amplification of the 3' end of the Can f I cDNA produced a single prominent DNA fragment ~500 bp in length. However, the three partial 3' cDNAs were either significantly longer or shorter than 500 bp. This suggested rare partial cDNAs were being subcloned, perhaps because the authentic Can f I cDNA harbored the restrictions site(s) encoded at the ends of the primers used in subcloning of DNA fragments that arise from PCR amplification. Hence, when digesting the PCR product representing the authentic Can f I cDNA with restriction endonucleases (in this case 5' EcoR I and 3' BamH I) one would 1) cut the authentic Can f I cDNA into at least two pieces, and 2) bias towards subcloning rare cDNAs that had arisen from alternative splicing of the nascent Can f I RNA transcripts that had exons containing EcoR I and/or BamH I sites deleted. To address this situation, new primers with different restriction enzyme sites at their 5' ends were synthesized and used in RACE PCR of the 3' end of the Can f I cDNA. The JM3-3 oligo was resynthesized with a Bgl II linked to its 5' end [JM3–3XB (SEQ ID NO:21)] (FIG. 2), while the 5' primers SD and SE were resynthesized with Xho I sites at their 5' ends [XSD (SEQ ID NO: 16) and XSE (SEQ ID NO: 18)] (FIG. 2). After nested PCR of JM3 primed total dog parotid cDNA using these new primers and the previous amplification conditions, the intact 3' end of the Can f I cDNA (which hybridized to kinase labeled Dog Probe 4, [(SEQ ID NO:20), residues 115–121 of mature Can f I (SEQ ID NO:19) (FIG. 2)] was subcloned and sequenced. The translated amino acid sequence of the partial cDNA corresponded directly with the protein sequence data and extended it a further 6 amino acids before encountering a stop codon. As the cloning artifacts had predicted, both EcoR I and BamH I sites were found in the coding region of the intact 3' Can f I cDNA.

Figure 3:
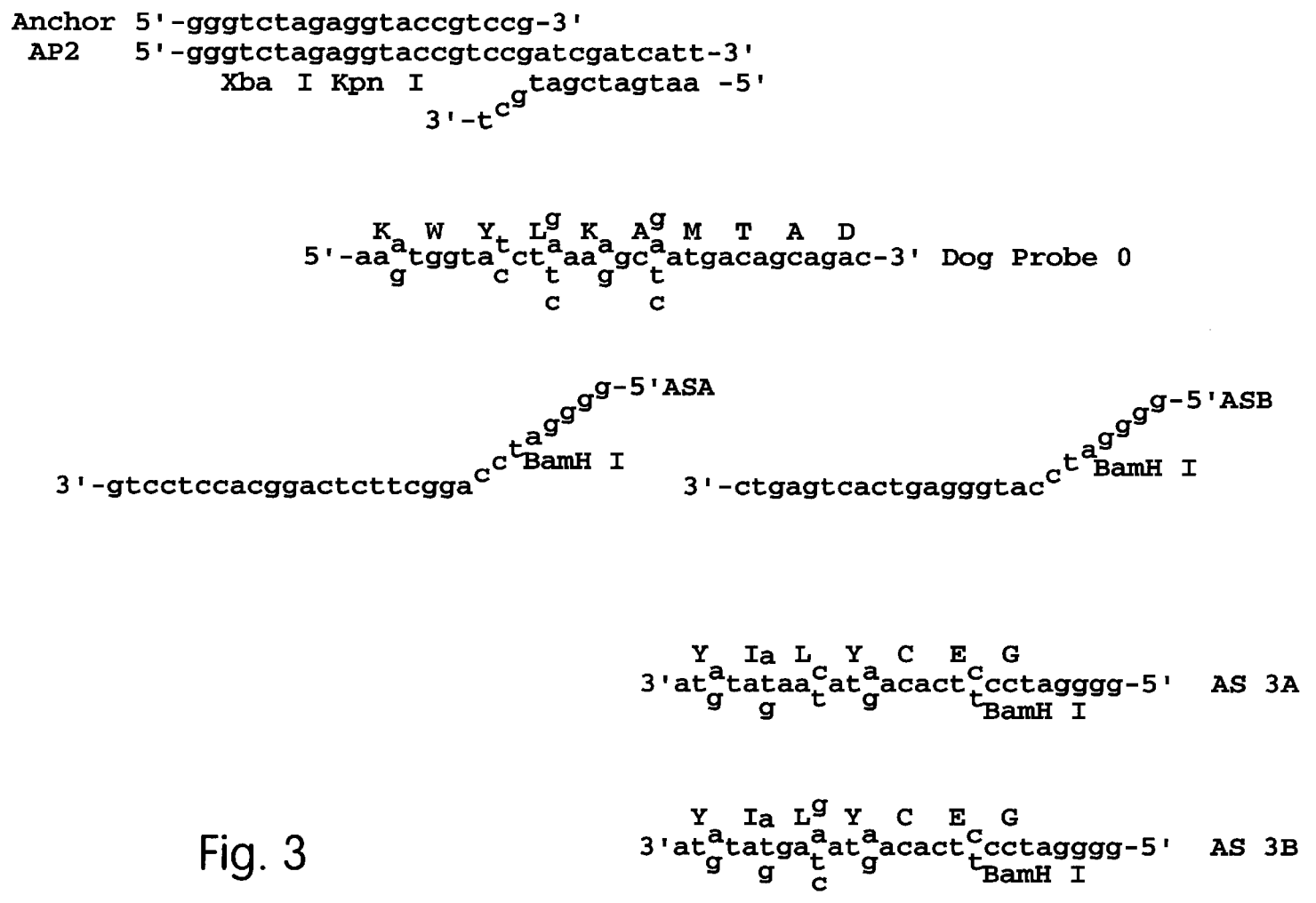

The 5' end of the Can f I cDNA was cloned using an anchored PCR technique (Roux, K. H. and Dhanarajan, P., (1990) Biotechniques, 8:48–57; Rafnar, T. et al., (1991) J. Biol. Chem., 266:1229–1236). Double strand dog parotid cDNA was synthesized using a kit (BRL Superscript cDNA Synthesis System) employing the method of RNase H priming of the second strand of cDNA synthesis (Gubler, U., and Hoffman, B. J., (1983) Gene, 25:263–269). The blunt double stranded cDNA was ligated to an anchor adapter, thereby placing a known sequence at the 5' ends of cDNAs (SEQ ID NO:25; SEQ ID NO:26; and SEQ ID NO:27) (see FIG. 3). A primer based on the anchor sequence was used as a 5' sense primer (AP) in conjunction with a nested pair of 3' antisense primers, ASA (SEQ ID NO:3 1) [residues 18 to 24 (SEQ ID NO:30)] and ASB (SEQ ID NO:33) [residues 25 to 30 (SEQ ID NO:32)] based on known Can f I cDNA sequence from MOPAC PCR in sequential rounds of PCR (40×[92° C. 30 seconds/60° C. 1 minutes/75° C. 1 minutes]) to amplify the 5' end of the Can f I cDNA (1° reaction ds anchored cDNA template with 5' AP/3' ASB primers: 2° reaction 1/100th 1° reaction template with 5' AP/3' ASA primers). Agarose gel electrophoresis analysis of the 2° reaction revealed a broad band ~300 bp in length, which in Southern blot analysis hybridized to a 32P kinased degenerate oligonucleotide probe, Dog Probe 0 (SEQ ID NO:29) (FIG. 3), based on residues 9 to 17 (SEQ ID NO:28) of mature Can f I. The amplified fragment was subcloned into Bluescript KS plasmid and subjected to DNA sequence analysis. It's authenticity as the 5' end of the Can f I cDNA was confirmed by the presence of the first 13 residues of mature Can f I protein at the 3' end of the partial cDNA. Sequence of the longest partial 5' cDNA extended a further 126 bp and encoded a 26 amino acid leader sequence not found in mature Can f I. Although no in-frame stop codons were found 5' of the presumed initiator methionine codon (M-26), it is presumed to be the true initiator codon and not just an internal methionine residue because: 1) it is embedded within a consensus sequence for translation initiation in mammalian cells (Kozak, M., (1986) Cell, 44:283–292); and 2) the predicted leader sequence is highly homologous to the leader sequences of proteins that are highly related to Can f I (see below).

A contiguous Can f I cDNA was then amplified and both strands directly sequenced as a PCR product to confirm the coding sequence of the molecule. To minimize the possibility of introducing errors in the amplified cDNA during the PCR reaction, Pfu I DNA polymerase (Stratagene, San Diego, Calif.) was used to amplify the coding cDNA. Pfu I DNA polymerase has been documented to introduce an order of magnitude fewer errors than Taq DNA polymerase during PCR (Lundberg, K. S., (1991) Gene, 108:1–4). Direct sequencing of non-cloned DNA fragments from PCR reactions should also obviate any errors made by DNA polymerases during PCR since such errors will be scattered at random throughout the population of PCR products (Gyllensten, U. B., and Ehrlich, H. A., (1988) Proc. Natl. Acad. Sci. USA, 85:7652–7656). Primers used in the amplification/sequencing included the 5' sense leader ex oligo (SEQ ID NO:35) [residues -26 to -20 of Can f I (SEQ ID NO:34)] and the 3' antisense stop Bgl II oligo (SEQ ID NO:36) [a 24-mer 40 bp 3' of the stop codon of Can f I] (FIG. 4). A program of 40×(95° C. 30 seconds/60° C. 45 seconds/75° C. 45 seconds) was used with the aforementioned primers and Pfu I DNA polymerase to amplify a DNA fragment ~600 bp in length, which was subsequently isolated as a band on a 0.6% low melt agarose gel. This gel slice was melted at 70° C. and used as template for PCR sequencing using 32P labelled oligonucleotides as primers and a commercially available kit (AmpliTaq Cycle Sequencing Kit, Perkin Elmer Cetus, Norwalk, Conn.). A program of 30×(95° C. 30 seconds/60° or 68° C. 30 seconds) was used for the cycle sequencing. The PCR sequencing strategy to obtain unambiguous sequence of the mature Can f I protein from both strands of the amplified cDNA is depicted in FIG. 4 with the following sense primers: start ex (SEQ ID NO:37); SB (SEQ ID NO:38); SK (SEQ ID NO:39); SE (SEQ ID NO:40); and SH (SEQ ID NO:41), and the following antisense primers: Dog 9 (SEQ ID NO:42); ASK (SEQ ID NO:43); ASB (SEQ ID NO:44); and ASJ (SEQ ID NO:45). PCR cycle sequencing analysis of amplified cDNA encoding the mature Can f I protein served to confirm the DNA sequence obtained previously from cloned partial cDNAs of Can f I, FIG. 4.

In order to infer the possible biological function of Can f I, its amino acid sequence was compared to those in the GenBank, GenBankUpdate, EMBL, and EMBL Update sequence data bases (as of Jun. 25, 1992) using the NCBI BLAST network service (Altschul, S. F., et al., (1990) J. Mol Biol., 215:403–410). Can f I precursor protein (including the signal sequence not found in mature Can f I protein) displayed strong homology to three proteins: 1) Human von Ebner's gland protein; 2) Rat (VEG) von Ebner's gland protein precursor (Hartwig, S., et al., (1990) Nature, 343:366–369); and 3) Rat odorant-binding protein (Pevsner, J., et al., (1988) Science, 241:336–339). von Ebner's gland is a sublingual gland and secretes an abundant protein into the saliva speculated to be involved in potentiating the sense of taste involving hydrophobic molecules. von Ebner's gland protein belongs to a superfamily of of lipophilic molecule carriers (Godovac-Zimmermann, J., (1988) Trends Biochem. Sci., 13:64–66). The homology between Can f I and the human and rat von Ebner's gland proteins indicates that Can f I may be the canine homolog of von Ebner's gland protein. Additional data indicates that Can f I mRNA is expressed predominantly in the tongue epithelial tissue where von Ebner's glands are localized and only at a very low level (not detectable by Northern blot analysis) in parotid glands.

EXAMPLE 3

Protein Sequence Analysis of Purified Can f II

Affinity purified Can f II protein was obtained from Dr. Aalberse (de Groot, H. et al., supra). An Applied Biosystems Model 477A gas phase sequencer with on-line phynylthiohydantoin (HTH) amino acid analysis (Model 120A) was used to sequence the purified Can f II protein. A modification of the extraction program, multiple butylchloride extractions, was used to improve the amino acid recovery. O-phthaladehyde (OPA) was used in blocking of primary amines when proline was located at the amino terminus. Brauer, A. W., et al., (1984) *Anal. Biochemistry*, 137:134, 142. In situ alkylation was performed by using the non-nucleophilic reductant, tributylphosphine with concomitant alkylation by 4-vinyl pyridine in ethylmorpholine buffer. Andrews, P. C. and Dixon, J. E., (1987) *Anal. Biochemistry*, 161:524–528.

Using this methodology, the sequence of the N-terminus of the Can f II protein was determined. The N-terminal sequence of 38 amino acid residues which was identified through multiple N-terminal sequence analysis in conjunction with OPA blocking of contaminating signal represents a novel protein sequence FIG. 19 (SEQ ID NO: 88).

EXAMPLE 4

Extraction of mRNA From Canine Parotid Glands and Cloning of Can f II

Figure 14:
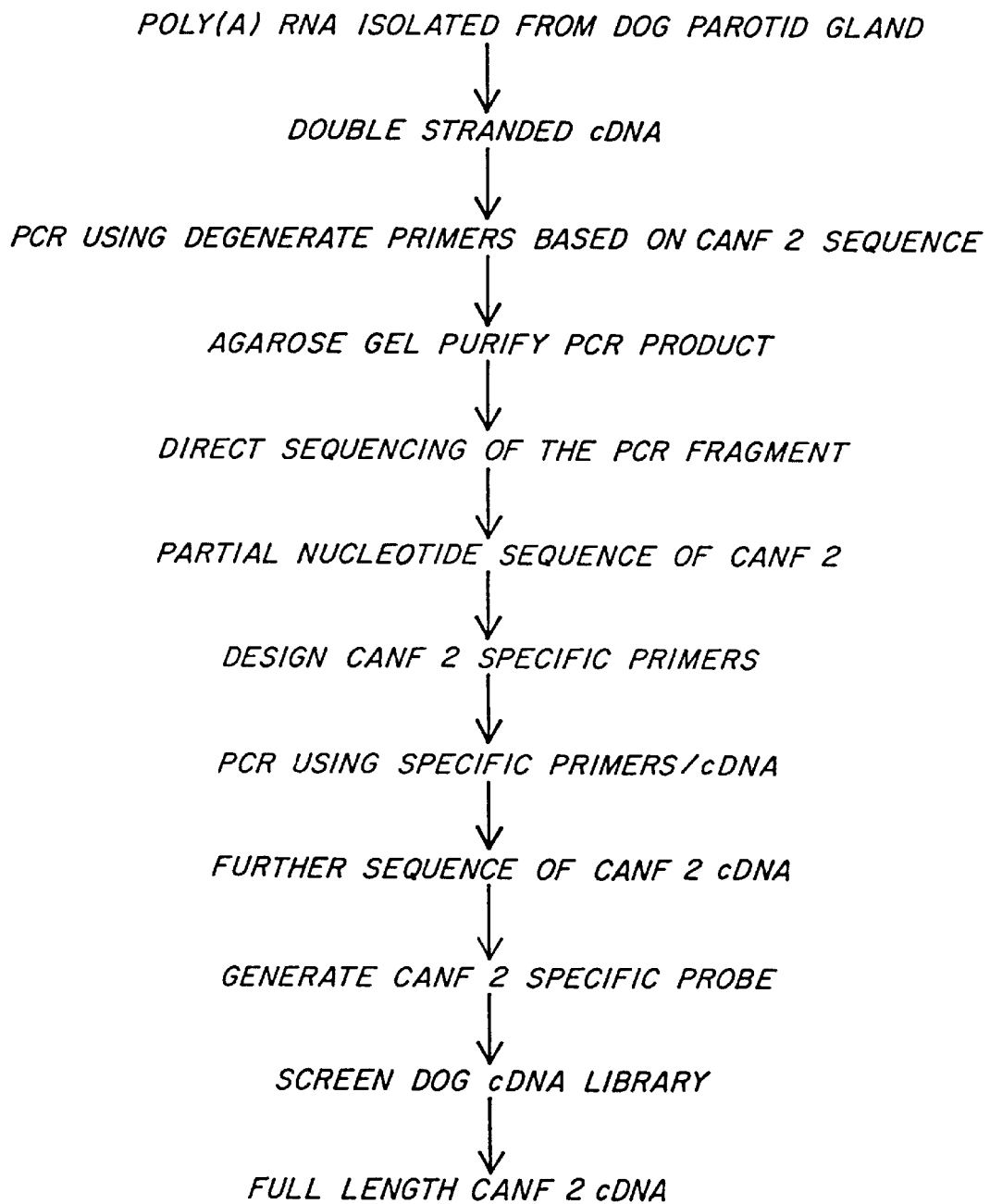
FIG. 14 is a schematic representation of the strategy used to clone Can f II cDNA.

The strategy used to clone Can f II is schematically drawn in FIG. 14. cDNA was synthesized using the above preparation as a template in reverse transcription. In the next step ds cDNA was used as a template for PCR along with degenerate primers which were designed based on amino acid sequence of Can f II and oriented to amplify a fragment of Can f II cDNA. PCR product was gel purified and than subjected to direct sequencing. The nucleotide sequence confirmed that the PCR product represents a fragment of Can f II cDNA. Further polymerase chain reactions were performed using Can f II specific primers in order to obtain a longer fragment which was subsequently used as a probe to screen a dog cDNA library. Positive clones were identified, plaque purified, sequenced and full length Can f II cDNA was obtained.

Fresh parotid glands from a single outbred dog were obtained from the Tufts University School of Veterinary Medicine (Worcester, Mass.), washed in phosphate buffered saline, and immediately frozen on dry ice. RNA was extracted essentially as described in the literature (Chirgwin, J. M. et al., (1979) *Biochemistry*, 18:5294–5299.). Two glands (approx. 50 g) were pulverized to a powder with a mortar and pestle frozen in liquid N2, and suspended in 25 ml of GTC buffer (50% w/v guanidine thiocynate, 0.5% w/v Na lauryl sarcosine, 0.7% v/v b-mercaptoethanol, 0.1% v/v Sigma Antifoam A (Sigma, St. Louis Mo.), 25 mM Na citrate, pH 7.0) and vortexed until dissolved. Genomic DNA present in the solution was sheared by forcing the solution through a 16 gauge needle until the viscosity of the solution no longer decreased. The sheared solution was centrifuged at 3K rpm for 5 minutes at room temperature. The supernatant was then sheared further through a 23 gauge needle until its viscosity no longer decreased, and cleared by centrifugation at 5 K rpm for 5 minutes at room temperature. The solution was layered onto a CsCl cushion (5.7 M CsCl, 10 mM EDTA pH 7.5) and centrifuged in a Beckman SW 41 Ti rotor at 35K rpm for 16 hours at 17° C. The supernatant was discarded and the RNA pellet washed in 70% EtOH then resuspended in 0.3 M NaOAc, 10 mM EDTA, 0.1% SDS. Two volumes of absolute EtOH were added, and precipitation carried out on dry ice. RNA was pelleted by centrifugation, 70% EtOH washed, and resuspended in TES (10 mM Tris, 1 mM EDTA, 0.1% SDS). The final yield was ~5.3 mg of total RNA. mRNA was isolated from total RNA by chromatography on oligo(dT) cellulose using the method described by Aviv, H. and Leder, P. (*Proc. Natl. Acad. Sci. USA,* (1972) 69:1408). 20 µg of poly (A) RNA was obtained from 1.7 mg of total RNA.

The conversion of gland poly(A) mRNA into double stranded cDNA was carried out using standard procedure (Ausubel et al., (1993) *Current Protocols in Molecular Biology*, John Wiley & Sons). First, poly(A)RNA was copied onto cDNA was using Amersham cDNA Synthesis System Plus according to the manufacturer's procedure. 4 µg of poly (A) RNA was used as a template and oligo dT(12–18) was used to prime first strand synthesis. The RNA in RNA/DNA hybrid was than removed by RNaseH and the second strand was synthesized by DNA Polymerase I. Double stranded cDNA was completed and made blunt by T4 DNA polymerase and *E. coli* DNA ligase according to Gubler, U. and Hoffman, B. J., (1983) *Gene*, 25:263).

Initially, PCR amplification (Mullis, K. B. and Faloona, F., (1987) *Methods Enzymol*, 155:355–360) was used to obtain a partial cDNA of Can f II encoding amino acids 16 to 29 (SEQ ID NO: 97) of the mature protein. Using dog parotid cDNA as a template with degenerate primer pairs (synthesized on an Applied Biosystems 392) based on residues 3 to 6 (S1A) (FIG. 13) (SEQ ID NO: 91) and (S1B) (FIG. 13) (SEQ ID NO: 92) and on residues 33 to 38 (ASP2A) (FIG. 13) (SEQ. ID NO: 93) and (ASP2B) (FIG. 13) (SEQ ID NO: 94) of mature Can f II, a DNA fragment of the predicted size (~120 bp) was amplified using a PCR kit (GeneAmp kit, Perkin Elmer Cetus, Norwalk, Conn.). Conditions for the reaction were: denaturation for 1 minute at 94° C.; annealing for 1 minute at 42° C. and polymerization for 1 minute at 72° C. The cycle was repeated 30 times. As a test of its authenticity, the amplified fragment was subjected to direct sequencing using a commercially available kit (AmpliTaq Cycle Sequencing Kit, Perkin Elmer Cetus, Norwalk, Conn.) according to the instructions supplied. Primers used in the amplification/sequencing (which included S1A, S1B, ASP2A and ASP2B) had been end labeled with γ-32P ATP using T4 polynucleotide kinase. The following program of 19 cycles (denaturation at 95° C. for 1 minute; annealing at 50° C. for 1 minute and extension at 72° C. for 15 seconds) was used for the cycle sequencing in a MJ Research Minicycler. The nucleotide sequence of about 40 nucleotides of the fragment was shown to correctly encode residues 16 to 29 of mature Can f II (SEQ ID NO: 97). The missing residue in the amino acid sequence of a native protein at the position 26 was found to be asparagine.

Figure 15A:
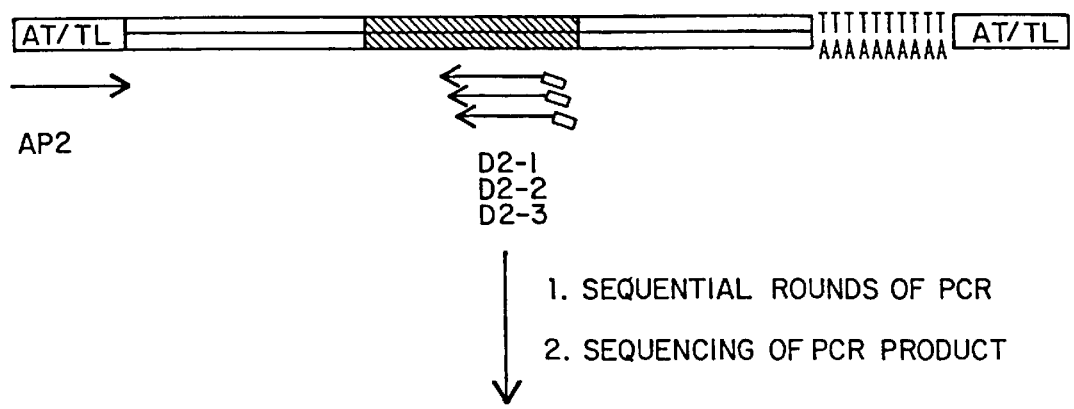
FIG. 15 is a schematic representation of the strategy used to clone the 5' (A) and 3' (B) portions of Can f II cDNA flanking the sequence encoding a portion of the amino acid sequence (shaded) of native Can f II.
Figure 15B:
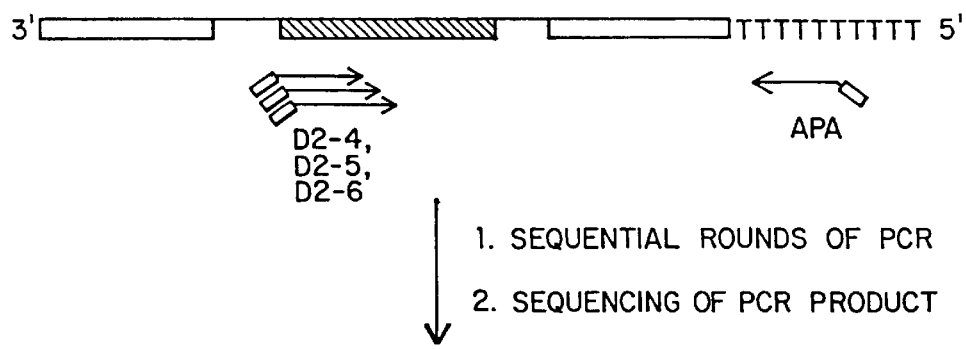

In order to generate a Can f II specific probe long enough (>100 bp) to be used to screen a cDNA library, the 5' and 3' ends of the Can f II cDNA were cloned using an anchored PCR technique (Roux, K. H. and Dhanarajan, P., (1990) *Biotechniques*, 8:48–57; Rafnar., T. et al., (1991) *J. Biol. Chem.*, 266:1229–1236) (FIG. 15). Double stranded dog cDNA was synthesized as described above. The blunt double stranded cDNA was than ligated to an anchor adapter AT/AL (FIG. 16; SEQ ID NO: 96 and 102) thereby placing a known sequence at 5' and 3' ends of cDNAs (FIG. 15A). In order to obtain the 5' end of Can f II cDNA, a primer based on the anchor sequence AP2 (FIG. 16) (SEQ ID NO: 95) was used as a 5' primer in conjunction with 3' antisense primers, D2–1 (residues 22 to 30) (FIGS. 13 and 16) (SEQ ID NO: 74), D2–2 (residues 17 to 25) (FIGS. 13 and 16) (SEQ ID NO: 75) and D2–3 (residues 16 to 21) (FIGS. 13 and 16) (SEQ ID NO: 76) based on known Can f II cDNA sequence obtained from initial PCR. Sequential rounds of PCR (40× [92° C. 30 seconds/60° C. 1 minute/75° C. 1 minute]) were carried out to amplify the 5' end of the Can f II cDNA. In the 1° reaction, double stranded anchored cDNA was used as a template along with 5' AP2/3' D2–1 primers; in the 2° reaction 1/20th of the 1° reaction mixture was used with 5' AP2/3' D2–2 primers; in the 3° reaction 1/20th of 2° reaction mixture was used with AP2/D2–3 primers). 1% agarose gel electrophoresis of the reaction products revealed the presence of a single band of ~300 bp long. As expected from the position of primers (see FIG. 15), the 2° and 3° reactions products migrated faster than 1° reaction product. The amplified fragment from the 3° reaction was gel purified and subjected to DNA sequence analysis. It's authenticity as the 5' end of the Can f II cDNA was confirmed by the presence of the first N-terminal residues of mature Can f II protein (FIG. 15A, shaded residues). The 5' portion of cDNA (FIG. 15A) (SEQ ID NO: 98) encoded part of the amino acid signal sequence which was not found in mature Can f II. The 3' portion of Can f II (FIG. 15B) (SEQ ID NO: 99) was synthesized in an analogous manner as the 5' end except that single stranded cDNA was used as a template and APA (FIG. 16) (SEQ ID NO: 100) was used as a 3' primer and D2–4,(SEQ ID NO: 77), D2–5 (SEQ ID NO: 78) and D2–6 (SEQ ID NO: 79) (FIGS. 14 and 16) were used as internal primers in PCR. Direct sequencing of the PCR product from the 3° reaction revealed the presence of 8 amino acids of the known Can f II sequence followed by 8 amino acids downstream of the known sequence.

Figure 17:
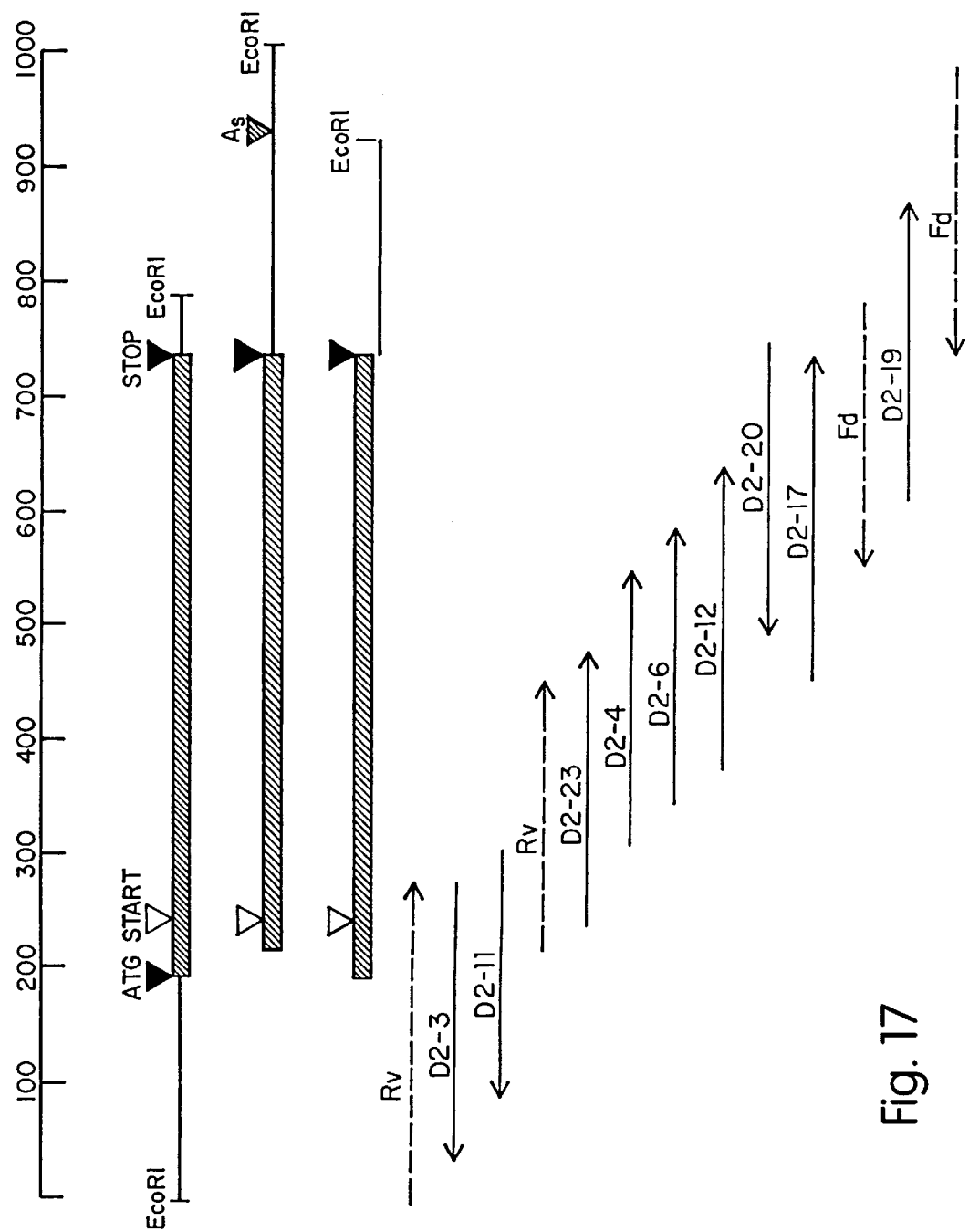
FIG. 17 shows the sequence strategy used to determine the nucleotide sequence of the Can f II cDNA clones 1a, 1c and 1j. The figure depicts inserts of the cDNA clones 1a (793 bp), 1c (791 bp) and 1j (774 bp). The hatched bars represent coding sequence. The triangles indicate the position of an initiator methionine codon (ATG); the codon specifying the N-terminal amino acid residue of the mature protein (START); the position of a termination codon (STOP); and the position of a polyadenylation signal (As). The arrows indicate the extent and direction of the sequencing reactions.

In order to clone the full length Can f II cDNA, a cDNA library was prepared and screened using standard published procedures (Gubler and Hoffman, Ausubel at al., supra). The lambda cDNA library was custom made by Clontech Laboratories, Inc. as follows: the first strand cDNA was primed from poly(A) RNA by oligo d(T)15. The blunt ended double stranded cDNA was ligated to an Eco RI linker CCGGAATTCCGG (SEQ ID NO: 101), digested with EcoRI, size selected in order to obtain fragments larger than 500bp, and ligated into EcoRI cut and dephosphorylated vector λgt 10. The DNA was then packaged into lambda particles, plated on C600-hfl and C-600 E. Coli strains and the library titer was determined. The unamplified library consisted of 1.53×106 independent clones (clear plaques on C-600 hfl host) which contained inserts ranging in size from 0.6kb to 3–4kb. The average size of the insert as determined by PCR using Clontech λgt10 primers was 1.2 kb. 100,000 clones were plated on C-600hfl host and screened using Can f II specific probe. All manipulations leading to the cloning and sequencing of Can f II cDNA were done according to Protocols in Molecular Biology (Ausubel et al., supra). A Can f II probe was obtained by PCR amplification of dog cDNA using D2–9 (SEQ ID NO: 80) and D2–13 (SEQ ID NO: 83) primers (FIG. 16). The PCR product was then 32p labeled by random priming. 20 positive clones were plaque purified, phage DNA was extracted from individual clones, digested with EcoRI and subcloned into pUC18. The presence of inserts was verified by digestion of the plasmid DNA with EcoRI and the nucleotide sequence of three individual clones was determined using Sequenase (United States Biochemicals) and AmpliTaq Cycle Sequencing kit (Perkin Elmer Cetus, Norwalk Conn.) according to manufacturer's instructions. PCR cycle sequencing analysis served to resolve some DNA sequence ambiguities resulting most probably from the formation of secondary structures on GC-rich Can f II template. The sequencing strategy is depicted in FIG. 17. Primers used in the sequencing/amplification included commercially available 16-mer Reverse Sequencing Primer (–21) and 17-mer Sequencing Primer (–20) from New England BioLabs as well as the Can f II specific primers listed in FIG. 16.

The nucleotide sequence of the three clones revealed the presence of an open reading frame which included 38 N-terminal amino acid residues (amino acids 1 to 38 on FIG. 13)(SEQ ID NO: 88) of mature Can f II identified earlier by protein sequencing and PCR sequencing of partial cDNA (see above). Sequencing strategy and features of three cDNA clones 1a, 1c and 1j are shown on the FIG. 17. Clone 1c of 791 bp (SEQ ID NO: 67) encodes the full length Can f II precursor protein (including signal sequence) and contains 5' (bases 1 through 194) and 3' (bases 738 trough 791) untranslated regions. Clones 1a of 793 bp (SEQ ID NO: 69) and 1j of 774 bp (SEQ ID NO: 71), encode precursor Can f II proteins in which part of the signal sequence is missing and contain 3' untranslated regions which are longer then in 1c. The sequence alignment revealed a polymorphism among three clones (FIG. 18). The nucleotide sequence of 1a contains one nucleotide substitution (C to T at the position 607) and one deletion (at the position 752) compared to 1c (FIG. 18). The nucleotide sequence of 1j contains two nucleotide substitutions compared to 1a and 1c at positions 347 (T to C) and 401 (G to T). In addition, the sequence of clones 1a and 1c differ significantly at their 5' and 3' ends. The G to T substitution at the position 401 changes the predicted amino acid sequence of Can f II at residue 68 from glycine (GGC) to valine (GTC). All other nucleotide changes do not alter the amino acid sequence of Can f II since they are either silent mutations or they lie outside of the coding sequence of mature Can f II. The polymorphism among the cDNA clones may reflect the expression of Can f II genes from different alleles. It may also represent a cloning artifact due to the reverse trancriptase mediated synthesis of cDNA which may introduce errors (Holland et al., (1982) *Science,* 215:1577–1585). For example, the purified HIV-1 reverse transcriptase was found to introduce misincorporations at a rate of 1/2000 to 1/4000 (Preston et al., (1988) *Science,* 242:1168–1171). It is also possible that the formation of secondary structures on the GC-rich Can f II mRNA template may cause pausing of reverse transcriptase or abnormal termination of the synthesis.

The predicted sequence of Can f II protein shown in FIG. 18 (SEQ ID NO: 68) contains a 19 amino acid signal sequence encoded by base 195 through base 251 of the cDNA shown in FIG. 18 (SEQ ID NO: 67). This signal sequence is not found in the mature Can f II protein which is encoded by bases 252 through 734. The methionine codon at the position -19 is true initiator methionine codon and not just an internal methionine residue because: 1) the predicted amino acid sequence of a signal peptide (residues –19 to –1) is highly similar and identical in length to the signal sequences of proteins that are related to Can f II (see below); and 2) although another in-frame methionine codon is found 5' of the presumed initiatior metionine (position –53) it is unlikely to be true because the deduced amino acid sequence of a peptide starting at the residue –53 is much longer than any known signal sequence and does not show any similarity to any known signal sequence. The Can f II cDNA encodes a protein having a predicted molecular weight of 18.2 kDa, with a single potential N-linked glycosylation site. Because 1) no amino acid signal was found at residue 25 during protein sequence analysis, and 2) the asparagine residue resides within a consensus sequence for N-linked glycosylation (N26 K27 S28), these data strongly suggest that the N26 residue is modified by N-linked glycosylation. N-linked glycosylation may increase the molecular weight of the mature protein. The deduced amino acid sequence of the mature protein encoded by the nucleic acid sequence is identical to the known NH2-terminal and internal amino acid sequence determined by amino acid sequence analysis of purified Can f II protein conducted as described in Example 3.

Figure 20:
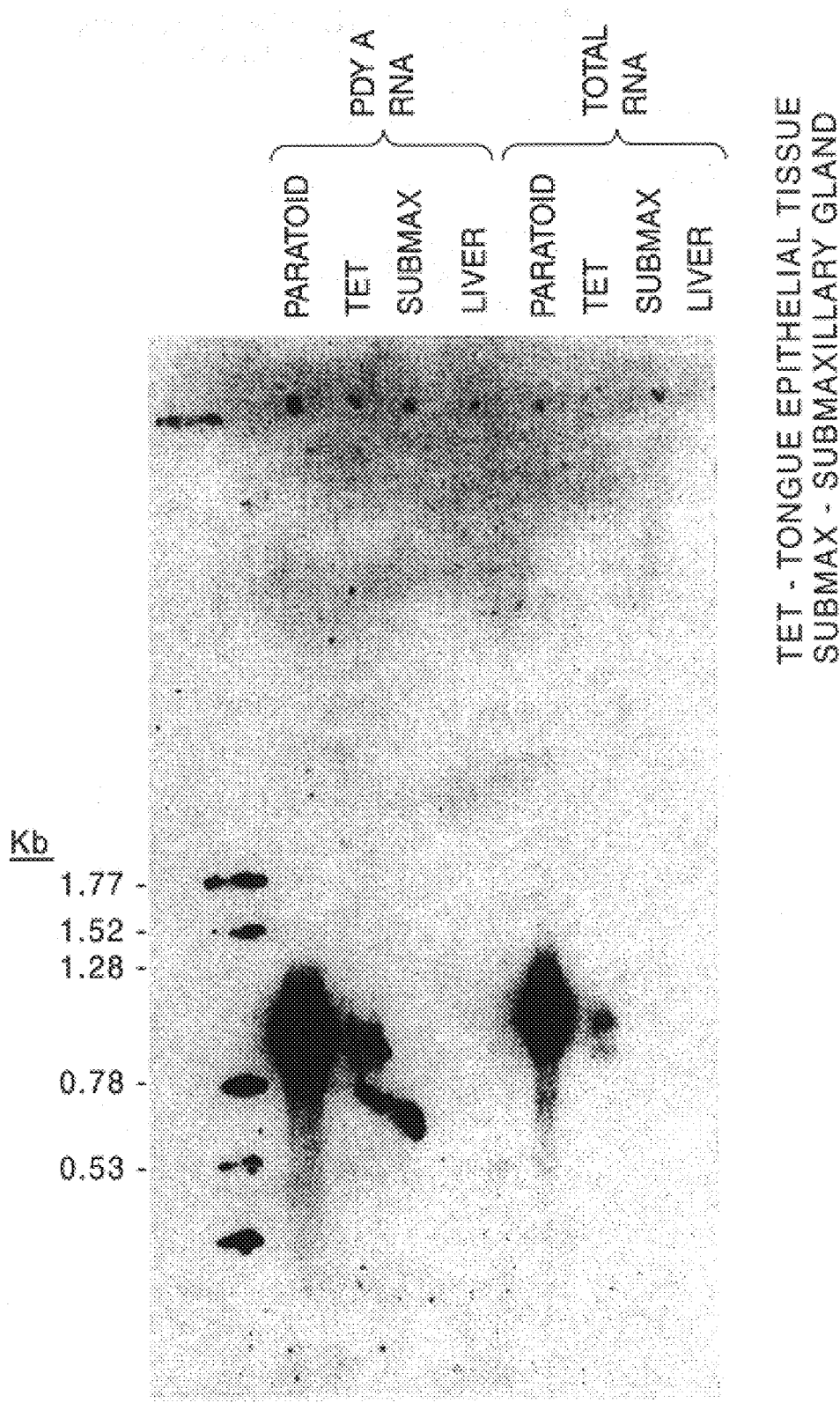
FIG. 20 shows northern analysis of mRNA of different dog tissues. Total cellular RNA (25 mg) from dog tongue epithelial tissue, parotid salivary gland, skin, mandibular and submaxiliary glands, liver and spleen was subjected to Northern analysis using Can f II cDNA as a probe. The position of RNA markers are indicated in kilobases (kb).

The expression of Can f II in various tissues was studied using the Northern blot technique. Poly (A) RNA or total RNA from various tissues was separated by electrophoresis through a 1.5% agarose gel containing 2.2 M formaldehyde. (Ausubel et al., supra). After electrophoresis, the separated RNAs were transferred onto GeneScreen membrane (NEN). Transfer, hybridization with a 32P labeled Can f II probe [obtained by PCR mediated amplification using D2–9 (SEQ ID NO: 14) and D2–13 (SEQ ID NO: 83) (FIG. 16) primers] and washings of the filter were performed according to the manufacturer's instructions. It appeared that the Can f II probe hybridized specifically at high stringency to RNA from dog parotid gland and to RNA from tongue epithelial tissue (FIG. 20). It did not hybridize to RNA from liver, or submaxiliary gland. Hybridization was observed to two bands of about 800 bp and 900 bp long, suggesting that Can f II may be encoded by two mRNA species. It is unlikely that two RNAs are transcribed from two different genes since a Southern blot experiment suggested that only a single copy Can f II geneis present in the dog genome. The two mRNAs encoding Can f II may be due to alternative splicing or to degradation of the mRNA. The former possibility seems very likely since different splicing configurations in the 3' noncoding region has been described for proteins which are similar to Can f II (Clark et al., (1984) *EMBO J.*, 3:1045–1052, see also below).

In order to infer the possible biological function of Can f II, its amino acid sequence was compared to those in the GenBank, GenBankUpdate, EMBL, and EMBL Update sequence data bases using the NCBI BLAST network service (Altschul, S. F., et al., (1990) *J. Mol Biol.*, 215:403–410). Can f II precursor protein displayed high similarity to two groups of related proteins: 1) Mouse Urinary Proteins (MUPs) (FIG. 21) (SEQ ID NO: 90) and 2) urinary a-2-globulins of rat (A2U) (FIG. 21) (SEQ ID NO: 89). The sequences of MUPs and A2Us show them both to be members of the lipocalin protein family (Cavaggioni et al., (1987) *FEBS Lett.*, 212:225–228). These are small proteins capable of binding hydrophobic molecules with high affinity and selectivity. This family now contains over 20 different proteins, principally identified through sequence homology (Flower et al., (1991) *Biochim. Biophys. Res. Commun.*, 180:69–74). The function of MUP and A2U remains unclear, but it is proposed that rodent urinary proteins are responsible for binding pheromones and their subsequent release from drying urine (Bocskei et al., (1992) *Nature*, 360:186–188). They are synthesized at different levels in the liver and in the submaxillary, lachrymal, sublingual, parotid and mammary glands (Shahan et al., (1987) *Mol. Cell. Biol.*, 7:1947–1954). MUP IV for example, is expressed predominantly in the lachrymal and parotid glands, but not in liver (Shahan et al., supra). The amino acid similarity of Can f II, MUP and A2U as well as their pattern of expression may indicate that Can f II is canine homolog of lipocalins. Interestingly, immunologic and biochemical studies of MUPs and MUP-related proteins have shown that these proteins are important human allergens (Lorusso et al., (1986) *J. Allergy Clin. Immunol.*, 78:928; Platts-Mills et al., (1987) *J. Allergy Clin. Immunol.*, 79:505; Gurka et al., (1989) *J. Allergy Clin. Immunol.*, 83:945–954).

EXAMPLE 5

Bacterial Expression of Can f I

Figure 6A:
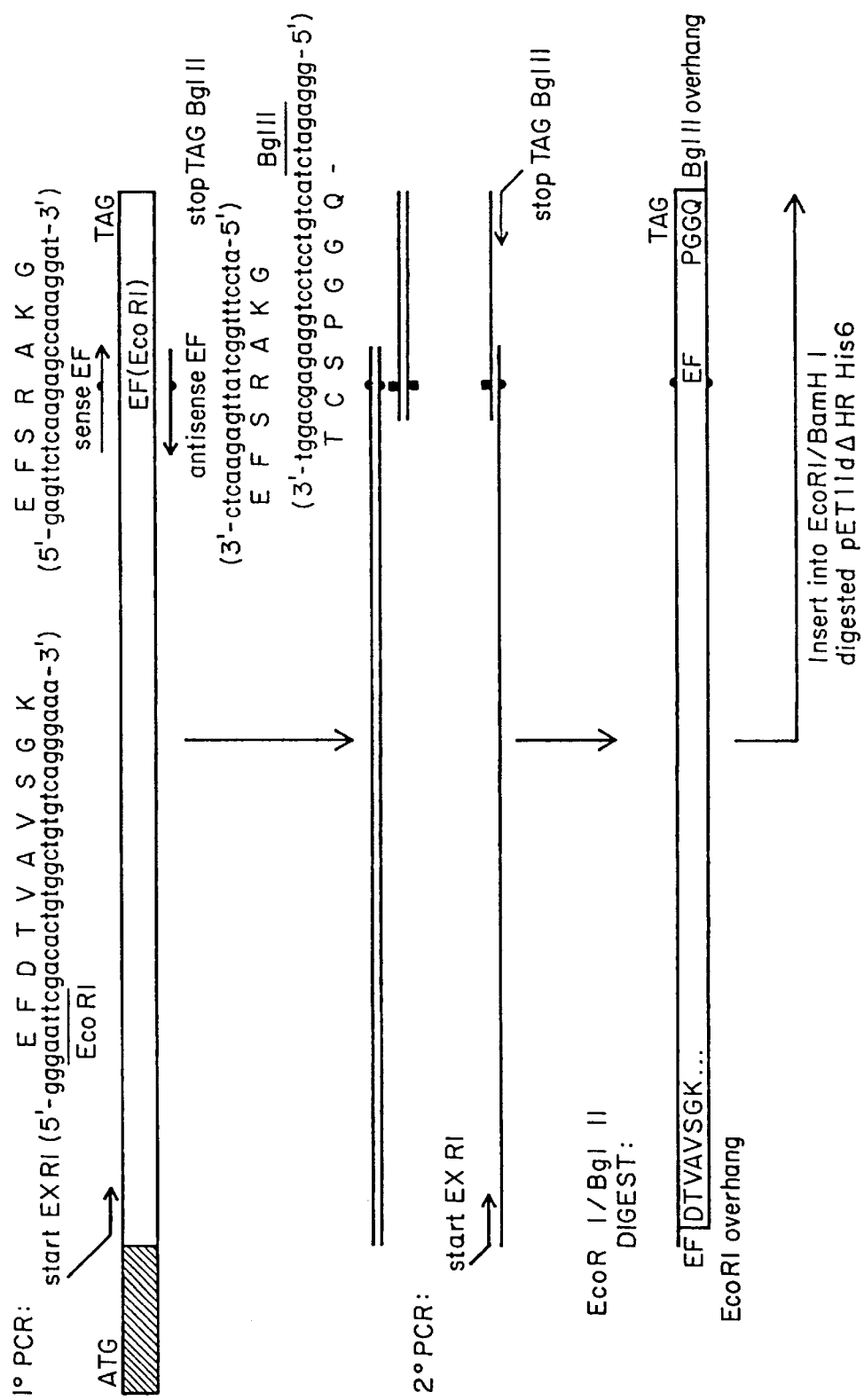
FIG. 6 is a schematic representation of the strategy used to express Can f I recombinant protein in bacteria.
Figure 6B:
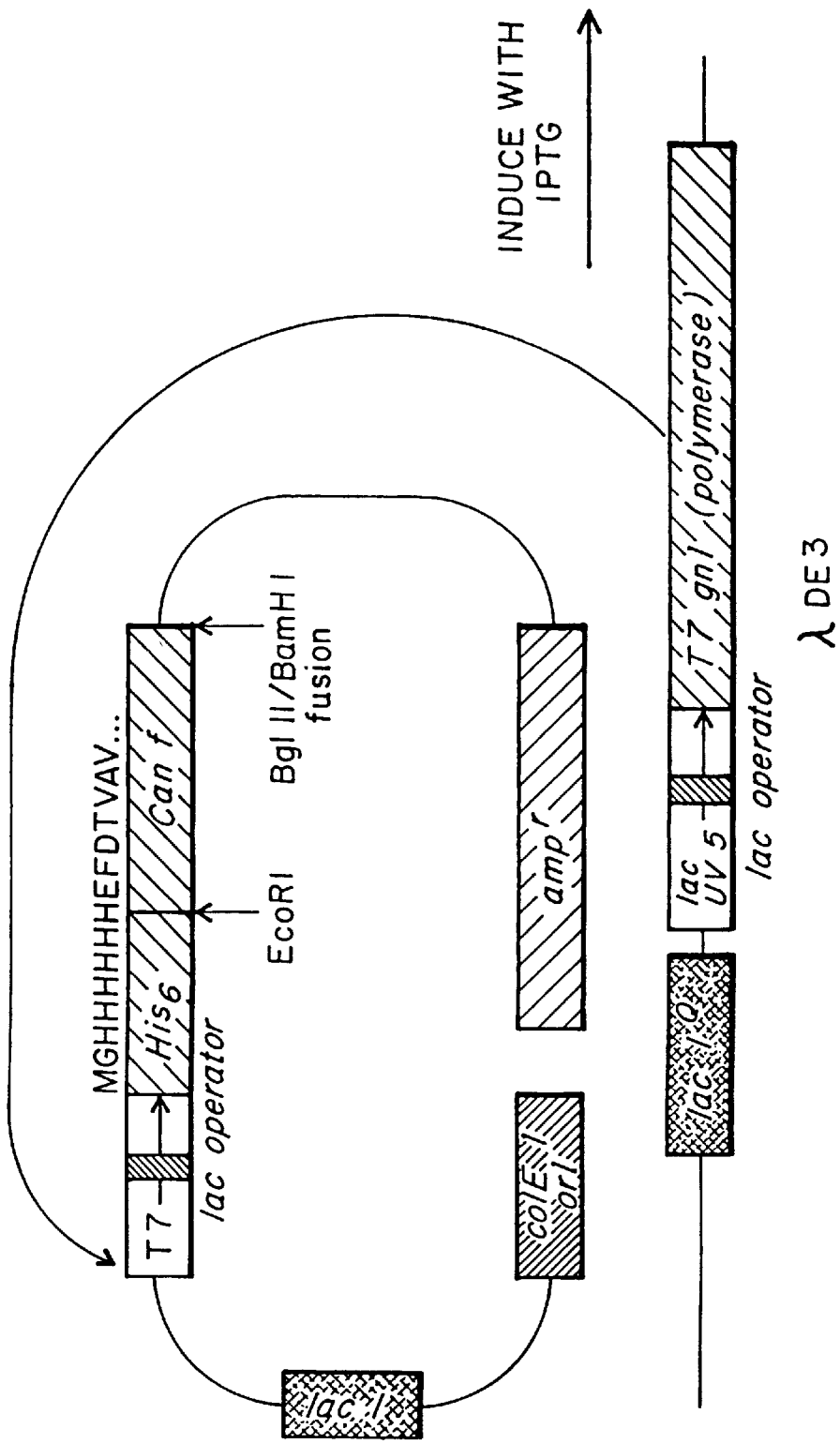

Bacterial expression of Can f I was performed as follows. The vector pET11d ΔHR His6 (Novagen, Madison, Wis.; modified at ImmuLogic Pharmaceutical Corporation by J. P. Morgenstern) was modified for expression of Can f I in *E. coli*, by removal of the internal EcoR I restriction site (at residues E143F144) from the Can f I cDNA to be inserted in the vector. This modification was necessary since all DNA fragments in this vector are cloned in frame with the His6 NH2 terminal leader sequence at a mutual 5' EcoR I site. Hence, EcoR I sites internal to the insert must be avoided. The pET11d ΔHR His6 vector also requires that inserts have a 3' BamH I site. However, since restriction sites such as Bgl II and Bcl I are compatible with BamH I overhangs, they could be placed at the 3' end of the Can f I cDNA, avoiding the need to mutate the internal BamH I site. A cDNA encoding the mature Can f I protein had its internal EcoR I site removed, a unique EcoR I site placed at its 5' end, and a Bgl II site placed at its 3' end in a two step PCR reaction (Ho et al., supra) using Pfu I DNA polymerase to minimize errors during amplification (FIG. 6). Two halves of the Can f I cDNA were amplified in primary PCR reactions (template: PCR fragment from cycle sequencing, program: 40×[95° 30 seconds/60° C. 45 seconds/75° C. 45 seconds]) with the 5' portion of the molecule being amplified with the Start ex (SEQ ID NO:46 and SEQ ID NO:47)/EF antisense (SEQ ID NO:50 and SEQ ID NO:48) primer pair and the 3' portion amplified with the sense EF (SEQ ID NO:49 and SEQ ID NO:48)/TAG Bgl II (SEQ ID NO:51 and SEQ ID NO:52) primer pair. Both EF primers were designed to introduce a point mutation in the EcoR I site at residues E143F144 of Can f I from GAATTC to GAGTTC, which would maintain the E143 residue since glutamate can be encoded by GAA or GAG codons.

Amplified DNA fragments of the expected size were isolated in gel slices from a 0.6% low melt agarose gel, melted at 70° C., mixed and used as template in a secondary (2°) PCR reaction with Start ex and TAG Bgl II primers. Mutagenized regions bearing the E143F144 pair should hybridize in the initial stages of the reaction to link the 5' and 3' ends of the Can f I cDNA, while the extreme 5' and 3' primers should serve to amplify the intact mutagenized cDNA. The entire reaction was phenol/chloroform extracted, EtOH precipitated, 70% EtOH washed, and digested with EcoR I and Bgl II. A band of the expected size (~450 bp) was isolated as a gel slice from a 0.6% low melt agarose gel, melted at 70° C., ligated at room temperature to EcoR I/BamH I digested pET 11dΔHR His6 plasmid, and the ligation transformed into XL-1 bacteria (Stratagene). Miniprep analysis of a 3 ml culture of one of the transformed colonies (using a Qiagen [Foster City, Calif.] plasmid mini kit) by Eco RV digestion revealed the presence of an insert of the appropriate size within the expression vector. A 300 ml culture seeded with this colony was grown, plasmid DNA extracted (Qiagen plasmid midi kit) and subjected to DNA sequence analysis. The entire 453 bp insert was shown to have the correct sequence for mature Can f I cDNA (including the mutated E143 codon from GAA to GAG), with the addition of an in-frame His6 reporter group (SEQ ID NO:53) encoded at its 5' end. This His6 reporter group was to be used in metal ion affinity purification of the recombinant protein using NTA Ni++ chelating resin (Qiagen; Hochuli et al., supra).

A single colony of BL21(DE3) pET 11d ΔHR His6Can f IdRI bacteria was inoculated into a 2 ml brain heart infusion (BHI) culture (+200 μg/ml ampicillin) and incubated at 37° C. until turbid but not saturated. At this point 6 μl was removed and added to 600 μl of BHI and mixed. 100 μl was spread onto each of 6 BHI agar plates (+200 μg ampicillin) and incubated overnight at 37° C. The next morning the bacterial lawn was scraped off of the plates, pooled and resuspended in 20 ml of BHI media, and then aliquoted 1 ml each into each of 18 500 ml BHI cultures (+200 µg/ml ampicillin) in 2 liter Ehrlenmeyer flasks. Cultures were incubated at 37° and shaken at 300 rpm until the A600 reached 1.0. Isopropyl-β-D-thiogalactopyranoside (IPTG) was than added to final concentration of 1 mM to induce expression of the T7 RNA polymerase gene which would in turn induce expression of His6Can f I protein from the hybrid T7 gn10/lac 0 promoter. Expression was allowed to proceed for 2 hours after which the bacteria were pelleted and resuspended in 6 M guanidine hydrochloride (GuHCl), 100 mM NaPO4, 10 mM Tris, 100 mM 2-mercaptoethanol pH 8.0. Extraction was carried out for 1 hour with vigorous shaking and terminated by pelleting of the insoluble material at 10 K rpm in a JA-10 rotor (Beckman) for 1 hour. Supernatant was removed, and its pH adjusted to 8.0 before loading onto a 50 ml NTA agarose column that had been equilibrated in 6 M GuHCl, 100 mM NaPO4, 10 mM Tris, pH 8.0. The column was washed by step gradient as follows: 1) 6 M GuHCl, 100 mM NaPO4, 10 mM Tris, pH 8.0, 2) 8 M urea, 100 mM NaPO4, 10 mM Tris, pH 8.0, 3) 8 M urea, 100 mM NaOAc, 10 mM Tris, pH 6.3 with each wash proceeding until the A280 of the effluent from the column reached background. Recombinant His6Can f I protein was eluted from the column with 8 M urea, 100 mM NaOAc, 10 mM Tris, pH 4.5. Yield of the pooled peak fractions was ~100 mg with a purity of ~80% as determined by densitometry of a sample of the material analyzed by SDS-PAGE.

E. coli transformed with the vector pET11d containing the nucleic acid encoding Can f I have been deposited with the ATCC at accession number 69167.

EXAMPLE 6

Mammalian Expression of Can f I Protein

To produce a possibly glycosylated form of recombinant Can f I protein expessed in mammalian cells, Can f I expression was carried out as follows. Full length Can f I protein (including the leader sequence not found in the mature protein) when expressed in mammalian cells should be properly folded, glycosylated, and secreted. Two systems for high level transient expression of recombinant Can f I were employed. First, transient expression of recombinant Can f I with a His6 reporter group fused to its COOH terminus was performed in NIH 3T3 cells using the pJ7Ω expression vector (Morgenstern, J. P. and Land, H., (1990) Nuc. Acids Res., 18:1068). pJ7Ω drives expression of genes inserted into its polylinker to high levels during transient transfection from its SCMV IE94 promoter (Morgenstern and Land, supra).

Figure 7:
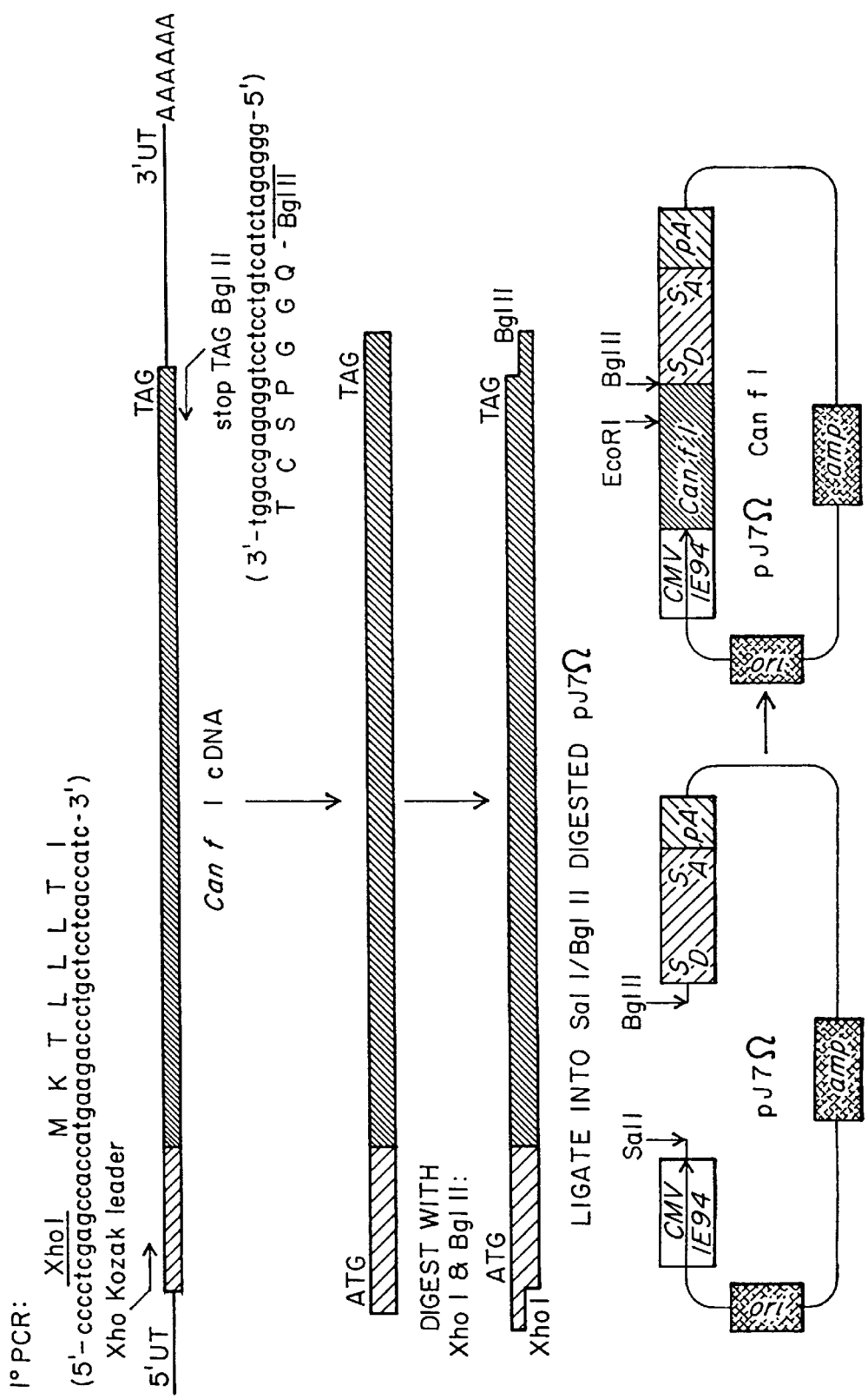
FIG. 7 is a schematic representation of the strategy used to express Can f I recombinant protein in a mammalian cell using the pJ7L expression vector.

A cDNA encompassing the entire Can f I coding sequence was amplified using Pfu I mediated PCR of total dog parotid cDNA with the 5' Kozak leader (SEQ ID NO:54)/3' TAG Bgl II (SEQ ID NO:51 and SEQ ID NO:52) primer pair (see FIG. 7). The entire PCR reaction was phenol-chloroform extracted, EtOH precipitated, 70% EtOH washed and digested with Xho I and Bgl II to generate correct overhangs for insertion into pJ7Ω. A band of the expected size (~600 bp) to encode the entire Can f I cDNA was isolated as a gel slice on a 0.6% low melt agarose gel, melted at 70° C. and ligated to Sal I/Bgl II digested pJ7Ω at room temperature (see FIG. 7). The ligation was transformed into competent XL-1 Blue E. coli and positive colonies selected on ampicillin (200 µg/ml) dishes. DNA sequence analysis of the 5' and 3' ends of inserts was performed on plasmid obtained from 3 ml cultures of two colonies (using a Qiagen plasmid mini kit). Both plasmids had inserts with the correct sequence of the 5' and 3' ends of full length Can f I.

Figure 8:
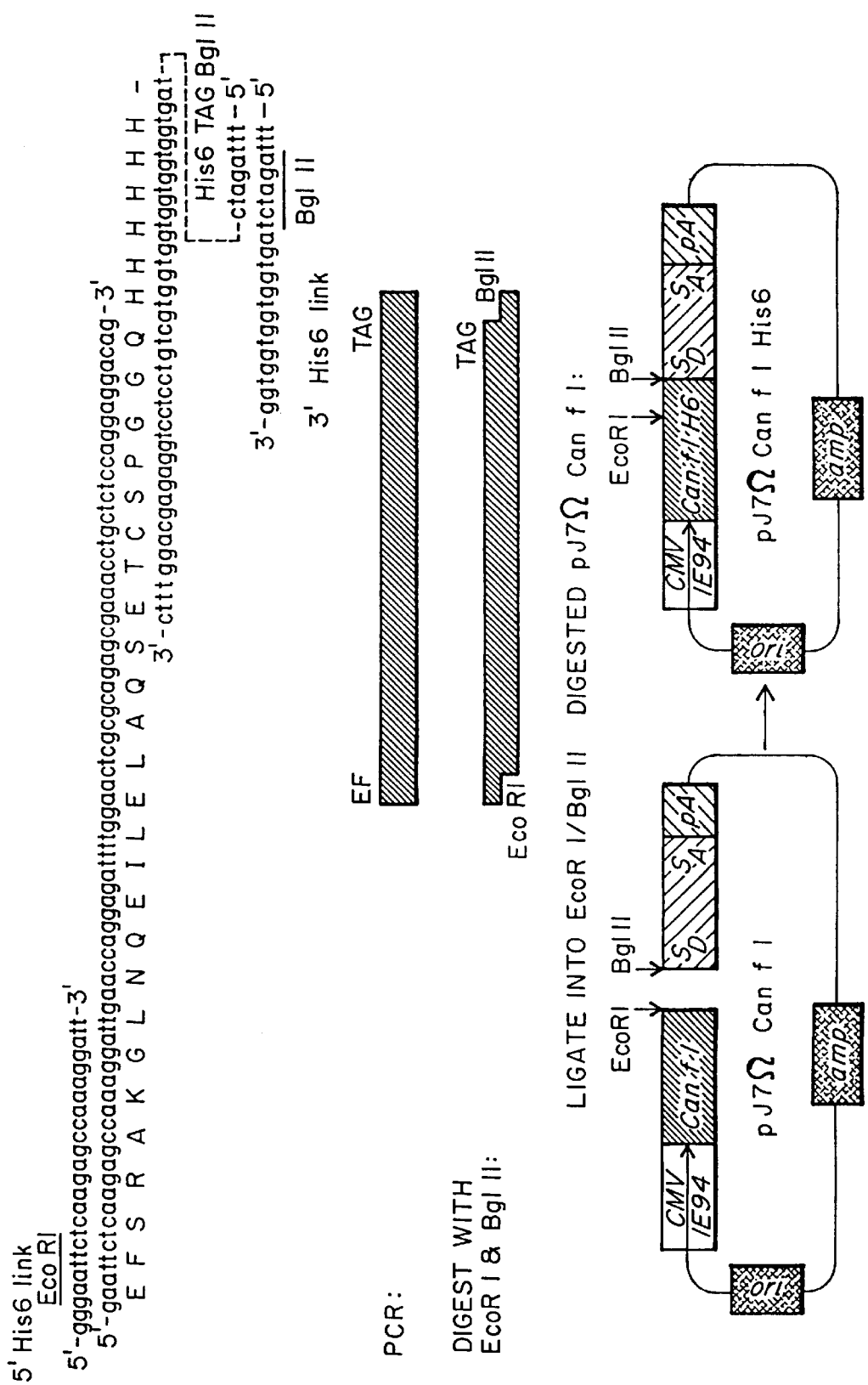
FIG. 8 is a schematic representation of the strategy used to insert a His6 reporter group at the carboxy terminus of the recombinant Can f I protein to aid purification of the protein.

Next, to aid in purification of recombinant Can f I protein produced in mammalian cells (Jankecht, R., et al., (1991) Proc. Natl. Acad. Sci. USA, 88:8972–8976), a His6 reporter group was to be fused at its COOH terminus. This was accomplished by excising the DNA fragment encoding the COOH terminus of Can f I as an EcoRI - Bgl II fragment and exchanging it with an EcoR I -Bgl II fragment encoding the COOH terminus of the protein that had been modified with the addition 6 histidines (FIG. 8). The COOH terminal His6 DNA fragment was generated by PCR of overlapping synthetic oligonucleotides as follows: a sense oligonucleotide (SEQ ID NO:56) encoding residues E123 to Q148 of the mature Can f I protein (SEQ ID NO:55); Sense 3' His6 link (SEQ ID NO:57); an antisense oligonucleotide encoding residues E141 to Q148/a His 6 tract/stop codon (SEQ ID NO:50 and SEQ ID NO:59); and 3' His6 TAG BglII (SEQ ID NO:60), were synthesized and purified by OPC column chromatography (Applied Biosystems, Foster City, Calif.). In addition, smaller primers composed of the first 24 nucleotides of the aforementioned oligonucleotides, 5' His6 link and 3' His6 link, were also synthesized. Linking and amplifying the two long oligonucleotides to generate the EcoR I - Bgl II DNA fragment encoding the Can f I COOH terminus-His6 fusion was performed by PCR. 10 pmoles of each large oligonucleotide were used as substrate in Pfu I mediated PCR with 1 µM primers using the program 40× (95° C. 30 seconds/60° C. 45 seconds/75° C. 30 seconds). The entire PCR reaction was phenol-chloroform extracted, EtOH precipitated, 70% EtOH washed and digested with EcoR I and Bgl II to generate correct overhangs for insertion into pJ7Ω Can f I. A band of the expected size (~110 bp) to encode the Can f I COOH terminus/His6 fusion was isolated as a gel slice on a 2.0% NuSieve agarose gel, melted at 70° C. and ligated to EcoR I/Bgl II digested pJ7Ω Can f I at room temperature. The ligation was transformed into competent XL-1 Blue E. coli and positive colonies selected on ampicillin (200 µg/ml) dishes. Plasmid was isolated from 4 cultures inoculated with different colonies and subjected to DNA sequence analysis at the 3' end of the insert. Clone #3 contained the expected His6 residues linked in frame to the COOH terminus of Can f I, so a large scale grow of this culture was undertaken to obtain large quantities of the pJ7Ω Can f I His6 plasmid for transfection. A one liter culture was amplified in 15 µM chloramphenicol once A600 reached 0.6. 800 µg of plasmid were isolated after alkaline lysis and two successive rounds of CsCl banding (Sambrook et al., supra).

Ten plates of NIH 3T3 cells were seeded at a density of 1.7×106 cells per 15 cm tissue culture dish, and the following morning, subjected to calcium phosphate transfection with 20 µg/dish of pJ7Ω Can f I His6 plasmid (Parker, B. A., and Stark, G. R., (1979) J. Virol., 31:360–369). 48 hours post transfection, supernatant was pooled from the dishes, filtered through a 0.45µ unit (Costar), and brought to a concentration of 1 µM imidazole, with the addition of protease inhibitors 1 mM PMSF, 1 µg/ml, pepstatin 1 µg/ml soybean trypsin inhibitor, and 1 µg/ml leupeptin. Metal ion affinity purification of the Can f IHis6 protein was achieved by loading the supernatant onto a 2 ml NTA agarose (Qiagen) column that had been equilibrated in 1 ×PBS, 1 mM imidazole, 1 mM PMSF, 1 µg/ml pepstatin, 1 µg/ml soybean trypsin inhibitor, and 1 µg/ml leupeptin. Non-specifically bound proteins were washed off the column with 10 column volumes of 1×PBS, 20 mM imidazole, 1 mM PMSF, 1 µg/ml pepstatin, 1 µg/ml soybean trypsin inhibitor, and 1 µg/ml leupeptin. Can f I His6 protein was specifically eluted from the column in 1×PBS, 80 mM imidazole, 1 mM PMSF, 1 μg/ml pepstatin, 1 μg/ml soybean trypsin inhibitor, and 1 μg/ml leupeptin (Hoffmann, A. and Roeder, R. G., (1991) *Nuc. Acids. Res.,* 19:6337–6338, and Janknecht et al., supra). Aliquots of the eluted fractions were analyzed by 12% SDS PAGE. Coomasie blue staining of the gel revealed three major bands of molecular weight ~70 kDa, 45 KDa, and 25 KDa. Since the molecular weight of native immunoaffinity purified Can f I is 25 KDa (Schou et al., supra and de Groot et al., supra) it was suspected that the smallest band on the SDS gel was recombinant Can f I His6.

EXAMPLE 7

Direct Binding of Human IgE to Recombinant Can f I by ELISA and Western blot

Figure 11:
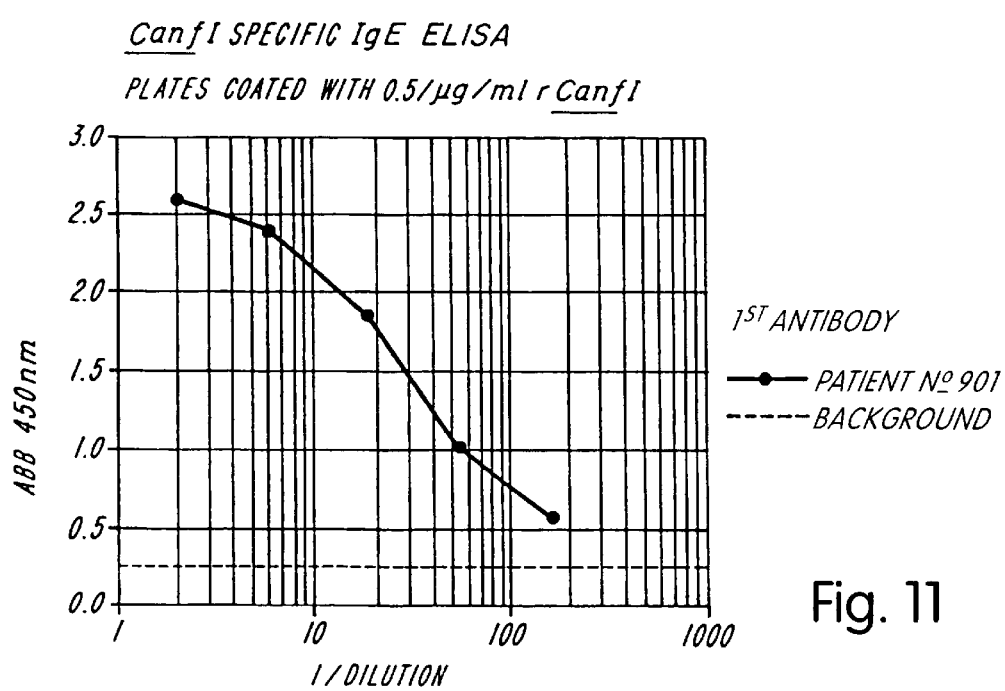
FIG. 11 is a graphic representation of a direct binding assay of IgE from a single dog allergic patient to bacterially expressed recombinant Can f I.

An ELISA plate (IMMULON II Dynatech, Chantilly, Va.) was coated with bacterially expressed recombinant Can f I, (rCan f I) at 0.5 μg/well in PBS-Tween and incubated overnight at 4° C. The coating antigen was removed and the wells were blocked with 0.5% gelatin in PBS, 200 μl/well for two hours at room temperature. Plasma from a skin test positive dog allergic patient, #901, was serially diluted with PBS-Tween and 100 μl was added per well and incubated overnight at 4° C. (the plasma dilutions were tested in duplicate). The second antibody (biotinylated goat anti-human IgE 1:1000, Kirkegaard & Perry Laboratories) was added at 100 μl/well for one hour at room temperature. This solution was removed and streptavidin-HRPO at 1:10,000, (Southern Biotecnology Associates, Inc. Birmingham, Ala.) was added for one hour at room temperature. TMB Membrane Peroxidase Substrate system (Kirkegaard & Perry Laboratories) was freshly mixed and added at 100 μl. The color was allowed to develop for 2–5 minutes. The reaction was stopped by the addition of 100 μl/well of 1M phosphoric acid. The plate was read on a Mircoplate EL 310 Autoreader (Biotek Instruments, Winooski, Vt.) with a 450 nm filter. The absorbance levels of duplicate wells were averaged. The graphed results are shown in FIG. 11. The data shows that patient #901 has a high level of anti-Can f specific IgE such that at 1/162 dilution (the highest plasma dilutin used) the binding level to the recombinant Can f I is still two-fold above background. A known negative patient (#250) was also tested and shown to be negative by this assay.

Figure 12:
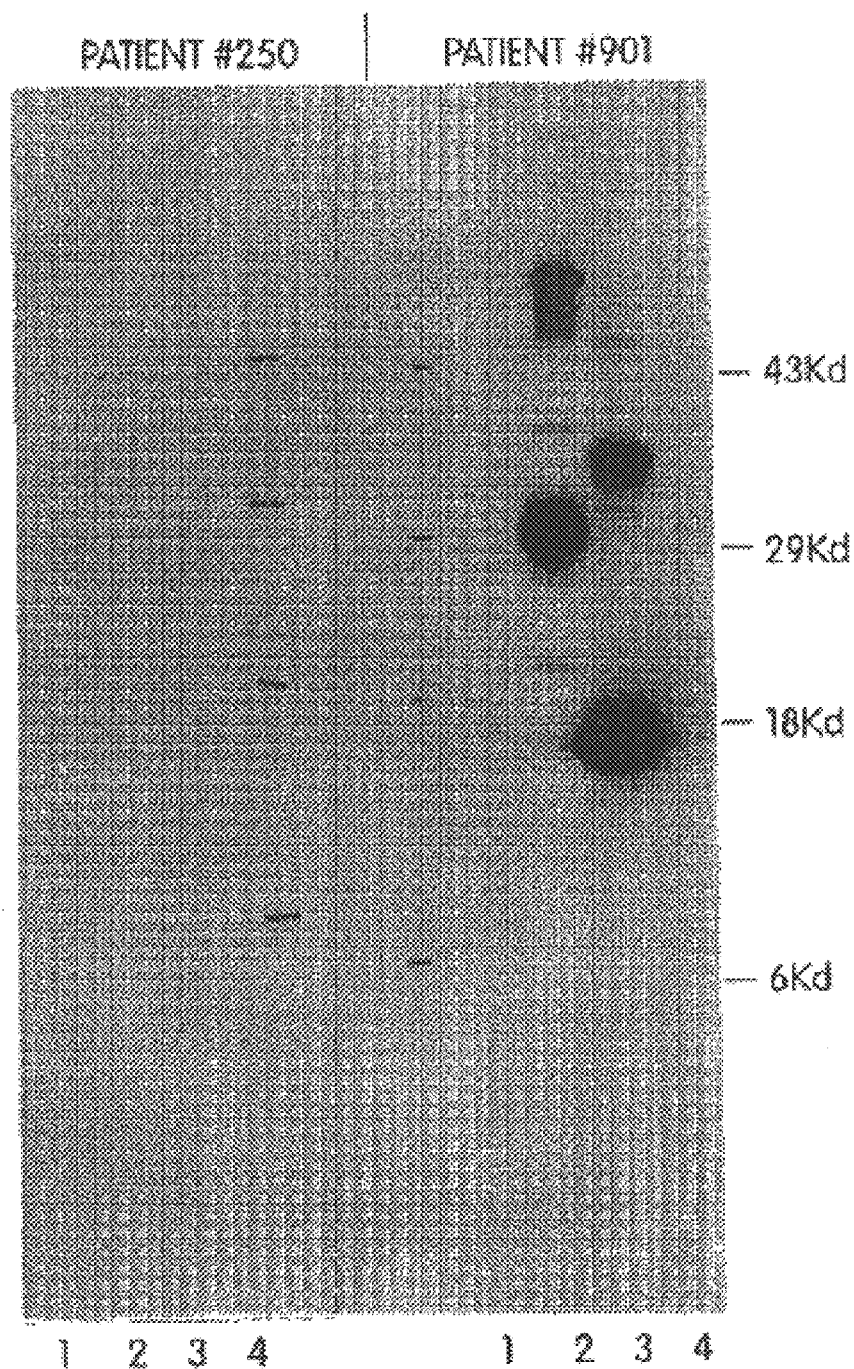
FIG. 12 shows Western blot analysis of four protein preparations (Lane 1: dog hair extract; Lane 2: dog saliva; Lane 3: bacterially expressed recombinant Can f I; and Lane 4: recombinant Can f I expressed in a mammalian cell culture system) probed with plasma from a dog allergic patient (#901) or with plasma from a negative control patient (#250).

Western Blot analysis of four different protein preparations as potential sources Can f I was performed. The four different prepparations used for Western blotting were: dog hair extract, dog saliva, bacterially expressed rCan f I (used for the ELISA) and rCan f I as expressed in a mammalian cell culture system. These preparations were loaded on a 15% acrylamide SDS-PAGE (lanes 1–4, respectively) at 5 μg/lane. The protein concentrations were based on the Bicinchoninic acid (BCA) assay (Pierce, Rockford, Ill.). Following electrophoresis, the proteins were transferred to nitrocellulose and stained with India Ink. The nitrocellulose sections were blocked by incubation in Tween solution with 1% milk/1% BSA for 30 minutes room temperature, then probed with patient #901 plasma or negative control patient #250 at a 1:20 dilution in tween mild solution. This first antibody incubation was carried out overnight at room temperature. Biotinylated goat anti-human IgE (KPL) was used as the second antibody at a 1:5000 dilution for a two hour incubation. Streptavidin-HRPO (1:20,000 dilution) and the ECL Western Blot Detection system (Amersham, Arlington Heights, Ill.) were used for detection by chemiluminescence. A 20 second exposure was performed and the film developed. The results from this assay show no recognition of the protein preparations by patient #250 IgE. The IgE from dog allergic patient #901 shows distinct binding to Can f I proteins in the saliva and the bacterially expressed recombinant Can f I (lanes 2 and 3, FIG. 12). The sizes of the protein forms are different between the two preparations and this is due to fact that the native Can f I protein found in dog saliva is glycosylated and runs with an apparent molecular weight of 28,000 daltons whereas the recombinant form from bacteria has no carbohydrate modification. The binding of IgE from serum of patients #901 to the mammalian expressed rCan f I is extremely faint and at present is only suggestive of positive expression. The full length bacterially produced form, lane 3, has an apparent molecular weight of 18,000 daltons and the larger IgE binding proteins in both lanes 2 and 3 are most likely dimeric structures of the lower molecular weight proteins.

EXAMPLE 8

Bacterial Expression of Can f II

Figure 13:
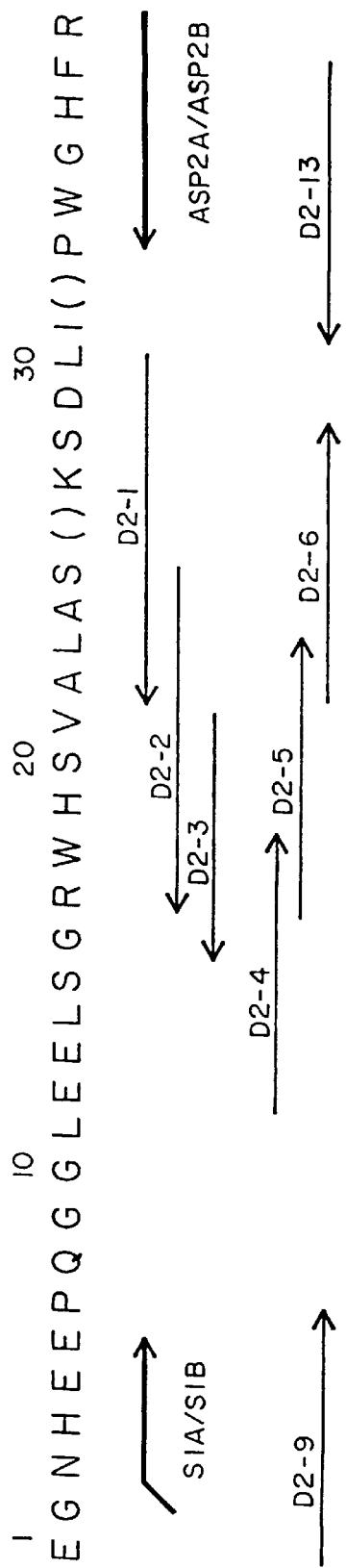
FIG. 13 shows the design of primers based on a partial amino acid sequence of mature Can f II and the sequence strategy for Can f II. () denotes residues which were not determined.

In an attempt to readily produce large amounts of pure recombinant Can f II protein, expression of Can f II in bacteria was carried out as follows. Full length cDNA encoding mature Can f II protein was obtained by amplification of the molecule from total parotid cDNA in PCR using D2–3pet (SEQ ID NO: 103) and D2–5pet (SEQ ID NO: 104) primer pair (FIG. 13). Primers were designed to introduce EcoRI and BamHI restriction sites at 5' and 3' of cDNA molecule respectively. The pET11d ΔHR His6 vector requires that inserts have 5' EcoRI site and 3' BamHI site.

Amplified DNA fragment of the expected size was purified by electrophpresis in low melting agarose and ligated at room temperature to EcoRI/BamHI digested pET11d ΔHR His6 plasmid and the ligation mixture was used to transform XL-1 Blue bacteria (Stratagene). Miniprep analysis of several transformed colonies (using Qiagen [Foster City, Calif.] plasmid mini kit) revealed the presence of an insert of the appropriate size within the expression vector. A 300 ml culture inoculated with one colony was grown, plasmid DNA extracted and subjected to sequence analysis. The entire 486 bp insert was shown to have the correct sequence for the mature Can f II cDNA with the addition of a reporter group encoded at the 5' end. This His6 reporter group was to be used in metal ion affinity purification of the recombinant protein using NTA Ni++ chelating resin (Qiagen). A single colony of BL21(DE3) pET 11d ΔHR His6Can f II bacteria was inoculated into a 2 ml brain heart infusion (BHI) culture (+200 μg/ml ampicillin) and incubated at 37° C. until turbid but not saturated. At this point 6 μl was removed and added to 600 μl of BHI and mixed. 100 μl was spread onto each of 6 BHI agar plates (+200 μg ampicillin) and incubated overnight at 37° C. The next morning the bacterial lawn was scraped off of the the plates, pooled and resuspended in 20 ml of BHI media, and then aliquoted 1 ml each into each of 18 500 ml BHI cultures (+200 μg/ml ampicillin) in 2 liter Ehrlenmeyer flasks. Cultures were incubated at 37° C. and shaken at 300 rpm until the A600 reached 1.0. Isopropyl-β-D-thiogalactopyranoside (IPTG) was than added to 1 mM to induce expression of the T7 RNA polymerase gene which would in turn induce expression of His6Can f II protein from the hybrid T7 gn 10/lac O promoter.

Expression was allowed to proceed for 2 hours after which the bacteria were pelleted and resuspended in 6 M guanidine hydrochloride (GuHCl), 100 mM NaPO4, 10 mM Tris, 100 mM 2-mercaptoethanol pH 8.0. Extraction was carried out for 1 hour with vigorous shaking and terminated by pelleting of the insoluble material at 10 K rpm in a JA-10 rotor (Beckman) for 1 hour. Supernatant was removed, and its pH adjusted to 8.0 before loading onto a 50 ml NTA agarose column that had been equilibrated in 6 M GuHCl, 100 mM NaPO4, 10 mM Tris, pH 8.0. The column was washed by step gradient as follows: 1) 6 M GuHCl, 100 mM NaPO4, 10 mM Tris, pH 8.0, 2) 8 M urea, 100 mM NaPO4, 10 mM Tris, pH 8.0, 3) 8 M urea, 100 mM NaOAc, 10 mM Tris, pH 6.3 with each wash proceeding until the A280 of the effluent from the column reached background. Recombinant His6Can f II protein was eluted from the column with 8 M urea, 100 mM NaOAc, 10 mM Tris, pH 4.5. Yield of the pooled peak fractions was ~100 mg with a purity of ~80% as determined by densitometry of a sample of the material analyzed by SDS-PAGE.

*E. coli* transformed with the vector pET11d containing the nucleic acid encoding Can f II have been deposited with the ATCC at accession number 69167.

EXAMPLE 9

Direct Binding of Human IgE to Native and Recombinant Can f II

Plasma samples from 14 dog-allergic patients (skin test 4+) were assayed for IgE binding to native Can f II and rCan f II. An ELISA plate (Immulon II Dynatech, Chantilly, Va.) was coated with native and bacterially expressed recombinant Can f II at 0.5 µg/well in PBS-Tween and incubated overnight at 4° C. The coating antigen was removed and the wells were blocked with 0.5% gelatin in PBS, 200 µl/well for two hours at room temperature. Binding of human IgE to the coating antigen was detected using biotinylated goat-anti-human IgE, streptavidin linked to peroxidase and TMB substrate. Reactions were read on a plate reader at 450 nm (A450). Of 14 plasma samples tested for IgE to native Can f II, 5 contained detectable antibody binding (FIG. 22A), with plasma from patients #901 and #227 containg the highest levels. Similarly, of 23 plasma samples tested for IgE to recombinant, bacterially expressed Can f II, several contained detectable antibody binding (FIGS. 22B and C).

EXAMPLE 10

Can f I Human T Cell Proliferation Analysis

To identify peptides having Can f I T cell stimulating activity several peptides derived from Can f I were produced and cultured with human T cell lines primed with recombinant Can f I protein and the responses were determined by standard T cell proliferation assays. A set of peptides derived from Can f I (Construct 1 (SEQ ID NO: 105), Construct 2 (SEQ ID NO: 106), and Construct 3 (SEQ ID NO: 107)), each representing a portion of the Can f I protein were used in proliferation assays. In addition, the assays included two peptides (A0095 (SEQ ID NO:108), amino acids 7 through 19; and A0096 (SEQ ID NO:109); amino acids 42 through 54) which were selected as containing potential T cell epitopes using the algorithm described in Hill et al., *Journal of Immunology* 147:184–197.

Constructs 1, 2 and 3 were produced by expressing and purifying portions of the Can f I protein in *E. coli* using standard techniques. DNA fragments encoding Construct 1 (amino acids 1 through 65 of Can f I) and Construct 2 (amino acids 56 through 108) were obtained by amplification from a plasmid pET11dΔ HRHis6Can f IΔ containing full length Can f I cDNA and were subcloned into an EcoRI/BamHI site of pET11d vector containing a His6 reporter sequence. A DNA fragment encoding Construct 3 (amino acids 90 through 148) was amplified from the same plasmid and subcloned into an EcoRI site of pET11d vector. Recombinant proteins were affinity purified on a NTA Ni$^{++}$ chelating resin (Qiagen) according to published protocol.

In order to perform in vitro assays of human T cell proliferative response to Can f I and the five Can f I peptides described above, whole blood obtained from subjects allergic to Can f I in a skin prick test was passed through a Lymphocyte Separation Media (LSM) to remove platelets, red blood cells and granulocytes. The resulting peripheral blood mononuclear cells (PBMC) were stimulated with 50 µg/ml of recombinant Can f I produced as described in Example 2 for 6 days in RPMI 1640 medium supplemented with 5% heat inactivated human AB serum, 2 mM L-glutamine,10 mM HEPES, 50 µM 2-mercapto-ethanol and 100 U/ml penicillin and streptomycin.

A second separation LSM was performed to remove high density cell debris and dead cells. The resulting PBMC cells were allowed to proliferate for 12–18 days. During this time the medium was supplemented with additions of recombinant IL2 (5units/ml) and IL4 (5 units/ml.).

When the lymphocytes reached a point of rest (determined such that an overnight pulse of 20,000 cells with $^3$H thymidine was within the 2000–4000 CPM range), the cells were restimulated for analysis in secondary proliferation assays. Secondary T cell proliferation assays included $2\times10^4$ T cells/well, $5\times10^4$ PBMC/well (irradiated with 3500 rads) as antigen presenting cells. Antigens were assayed in duplicate or triplicate wells at the following concentrations:

rCan f I: 4, 20 and 100 µg/ml.

Peptides: 3, 15, and 75 µg/ml.

Dog extract: 3, 15 and 75 µg of protein/ml. The concentration of Can f I in this preparation dog extract is unknown.

Constructs: initially at a single concentration of 20 µg/ml, then at 3, 15, and 75 µg/ml.

Constructs were insoluble at 75 µg/ml.

PHA was added at 1 µg/ml to indicate nonspecific activation ability. Tetanus toxoid, an irrelevant antigen, was added at dilutions of 1:2000, 1:4000 and 1:8000 to indicate T cell specificity.

After 3 days of culture under conditions of secondary assay 1 µCi of $^3$H thymidine was added to each culture well for overnight incubation. Cultures were harvested on glass fiber filters and $^3$H thymidine incorporation was measured by β scintillation counting. Stimulation indices which measure the strength of a T cell response to a peptide were calculated by dividing $^3$H thymidine uptake of treated cultures by $^3$H thymidine uptake of untreated medium controls.

The results of the secondary T cell proliferation assays are shown in FIGS. 24–25. FIG. 24 graphically compares the stimulation indices of individual subjects to rCan f I, peptides A0095–A0096 and Constructs 1–3. This comparison indicates that significant areas of T cell reactivity in the Can f I protein are found at all three parts of the protein, as shown by the substantial stimulation indices of Constructs 1–3 which, together, encompass the entire Can f I protein sequence.

Positivity indices for the peptides shown in FIG. 10 were calculated by multiplying the mean T cell stimulation index (FIG. 25) by the percent of the tested individuals who had a positive response or a T cell stimulation index of at least two. The percentage of positive responders for each tested peptide were as follows: rCan f I: 89%, A0095: 43%, A0096: 43%, Construct 1: 64%, Construct 2: 73%, Construct 3: 82%. Comparison of positivity indices (FIG. 10) which measures both the strength of a T cell response to a peptide (S.I.) and the frequency of a T cell response to a peptide in a population of dog dander allergen sensitive individuals indicates that both N terminal (amino acids 1 through 65) and C terminal (amino acids 90 through 108) ends of the Can f I protein contain a number of T cell epitopes.

EQUIVALENTS

Although the invention has been described with reference to its preferred embodiments, other embodiments can achieve the same results. Those skilled in the art will recognize or be able to ascertain using no more than routine experimentation, numerous equivalents to the specific embodiments described herein. Such equivalents are considered to be within the scope of this invention and are encompassed by the following claims.

What is claimed is:

1. A method of detecting the presence of an IgE mediated immune response to dog dander in a mammal sensitive to dog dander, comprising administering to said mammal an isolated dog dander allergen selected from the group consisting of Can f I and Can f II, wherein said allergen comprises the amino acid sequence of SEQ ID NO:2, SEQ ID NO:68, or the mature portions thereof, detecting the presence of the immune response in said mammal, and correlating the presence of the immune response with the presence of said dog dander allergen in the mammal.

2. A method of detecting the presence of an IgE mediated immune response to dog dander allergen in a mammal sensitive to such allergen, comprising administering to said mammal an antigenic fragment of a dog dander allergen selected from the group consisting of Can f I and Can f II, wherein said allergen comprises the amino acid sequence of SEQ ID NO:2 or SEQ ID NO:68, wherein said antigenic fragment comprises at least one epitope of said dog dander allergen, detecting the presence of the immune response in said mammal, and correlating the presence of the immune response with the presence of said dog dander allergen in the mammal.

3. The method of 2, wherein the epitope is a T cell epitope.

4. A method of detecting the presence of an IgE mediated immune response to dog dander allergen in a mammal sensitive to such allergen, comprising administering to said mammal an isolated dog dander allergen or antigenic fragment thereof capable of stimulating T cells specific for a dog dander allergen comprising the amino acid sequence of SEQ ID NO:2 or SEQ ID NO:68, detecting the presence of the immune response in said mammal, and correlating the presence of the immune response with the presence of said dog dander allergen in the mammal.

\* \* \* \* \*

SEQUENCE LISTING (1) GENERAL INFORMATION:

(iii) NUMBER OF SEQUENCES: 109

(2) INFORMATION FOR SEQ ID NO: 1:

(i) SEQUENCE CHARACTERISTICS:
      (A) LENGTH: 525 base pairs
      (B) TYPE: nucleic acid
      (C) STRANDEDNESS: single
      (D) TOPOLOGY: linear (ii) MOLECULE TYPE: cDNA (ix) FEATURE:
      (A) NAME/KEY: CDS
      (B) LOCATION: 1..525

(ix) FEATURE:
      (A) NAME/KEY: mat_peptide
      (B) LOCATION: 79..525

(xi) SEQUENCE DESCRIPTION: SEQ ID NO: 1:

```
ATG AAG ACC CTG CTC CTC ACC ATC GGC TTC AGC CTC ATT GCG ATC CTG        48
Met Lys Thr Leu Leu Leu Thr Ile Gly Phe Ser Leu Ile Ala Ile Leu
-26 -25                 -20                 -15

CAG GCC CAG GAT ACC CCA GCC TTG GGA AAG GAC ACT GTG GCT GTG TCA        96
Gln Ala Gln Asp Thr Pro Ala Leu Gly Lys Asp Thr Val Ala Val Ser
-10                  -5                   1                   5

GGG AAA TGG TAT CTG AAG GCC ATG ACA GCA GAC CAG GAG GTG CCT GAG       144
Gly Lys Trp Tyr Leu Lys Ala Met Thr Ala Asp Gln Glu Val Pro Glu
                10                  15                  20

AAG CCT GAC TCA GTG ACT CCC ATG ATC CTC AAA GCC CAG AAG GGG GGC       192
Lys Pro Asp Ser Val Thr Pro Met Ile Leu Lys Ala Gln Lys Gly Gly
                25                  30                  35

AAC CTG GAA GCC AAG ATC ACC ATG CTG ACA AAT GGT CAG TGC CAG AAC       240
Asn Leu Glu Ala Lys Ile Thr Met Leu Thr Asn Gly Gln Cys Gln Asn
    40                  45                  50

ATC ACG GTG GTC CTG CAC AAA ACC TCT GAG CCT GGC AAA TAC ACG GCA       288
Ile Thr Val Val Leu His Lys Thr Ser Glu Pro Gly Lys Tyr Thr Ala
55                  60                  65                  70

TAC GAG GGC CAG CGT GTC GTG TTC ATC CAG CCG TCC CCG GTG AGG GAC       336
Tyr Glu Gly Gln Arg Val Val Phe Ile Gln Pro Ser Pro Val Arg Asp
                75                  80                  85

CAC TAC ATT CTC TAC TGC GAG GGC GAG CTC CAT GGG AGG CAG ATC CGA       384
His Tyr Ile Leu Tyr Cys Glu Gly Glu Leu His Gly Arg Gln Ile Arg
                90                  95                 100

ATG GCC AAG CTT CTG GGA AGG GAT CCT GAG CAG AGC CAA GAG GCC TTG       432
Met Ala Lys Leu Leu Gly Arg Asp Pro Glu Gln Ser Gln Glu Ala Leu
               105                 110                 115
```

```
GAG GAT TTT CGG GAA TTC TCA AGA GCC AAA GGA TTG AAC CAG GAG ATT        480
Glu Asp Phe Arg Glu Phe Ser Arg Ala Lys Gly Leu Asn Gln Glu Ile
120                 125                 130

TTG GAA CTC GCG CAG AGC GAA ACC TGC TCT CCA GGA GGA CAG TAG            525
Leu Glu Leu Ala Gln Ser Glu Thr Cys Ser Pro Gly Gly Gln
135                 140                 145
```

(2) INFORMATION FOR SEQ ID NO: 2:

(i) SEQUENCE CHARACTERISTICS:
        (A) LENGTH: 174 amino acids
        (B) TYPE: amino acid
        (D) TOPOLOGY: linear (ii) MOLECULE TYPE: protein (xi) SEQUENCE DESCRIPTION: SEQ ID NO: 2:

```
Met Lys Thr Leu Leu Leu Thr Ile Gly Phe Ser Leu Ile Ala Ile Leu
-26 -25                 -20                 -15

Gln Ala Gln Asp Thr Pro Ala Leu Gly Lys Asp Thr Val Ala Val Ser
-10                 -5                  1                   5

Gly Lys Trp Tyr Leu Lys Ala Met Thr Ala Asp Gln Glu Val Pro Glu
                10                  15                  20

Lys Pro Asp Ser Val Thr Pro Met Ile Leu Lys Ala Gln Lys Gly Gly
            25                  30                  35

Asn Leu Glu Ala Lys Ile Thr Met Leu Thr Asn Gly Gln Cys Gln Asn
40                  45                  50

Ile Thr Val Val Leu His Lys Thr Ser Glu Pro Gly Lys Tyr Thr Ala
55                  60                  65                  70

Tyr Glu Gly Gln Arg Val Val Phe Ile Gln Pro Ser Pro Val Arg Asp
                75                  80                  85

His Tyr Ile Leu Tyr Cys Glu Gly Glu Leu His Gly Arg Gln Ile Arg
                90                  95                  100

Met Ala Lys Leu Leu Gly Arg Asp Pro Glu Gln Ser Gln Glu Ala Leu
                105                 110                 115

Glu Asp Phe Arg Glu Phe Ser Arg Ala Lys Gly Leu Asn Gln Glu Ile
120                 125                 130

Leu Glu Leu Ala Gln Ser Glu Thr Cys Ser Pro Gly Gly Gln
135                 140                 145
```

(2) INFORMATION FOR SEQ ID NO: 3:

(i) SEQUENCE CHARACTERISTICS:
        (A) LENGTH: 7 amino acids
        (B) TYPE: amino acid
        (D) TOPOLOGY: linear (ii) MOLECULE TYPE: peptide (v) FRAGMENT TYPE: internal (xi) SEQUENCE DESCRIPTION: SEQ ID NO: 3:

```
Trp Tyr Leu Lys Ala Met Thr
1               5
```

(2) INFORMATION FOR SEQ ID NO: 4:

(i) SEQUENCE CHARACTERISTICS:
        (A) LENGTH: 25 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO: 4:

GGGAATTCTG GTAYTTRGCN ATGAC                                                      25

(2) INFORMATION FOR SEQ ID NO: 5:

(i) SEQUENCE CHARACTERISTICS:
              (A) LENGTH: 28 base pairs
              (B) TYPE: nucleic acid
              (C) STRANDEDNESS: single
              (D) TOPOLOGY: linear (ii) MOLECULE TYPE: cDNA (xi) SEQUENCE DESCRIPTION: SEQ ID NO: 5:

GGGAATTCTG GTAYCTNAAR GCNATGAC                                                   28

(2) INFORMATION FOR SEQ ID NO: 6:

(i) SEQUENCE CHARACTERISTICS:
              (A) LENGTH: 8 amino acids
              (B) TYPE: amino acid
              (D) TOPOLOGY: linear (ii) MOLECULE TYPE: peptide (v) FRAGMENT TYPE: internal (xi) SEQUENCE DESCRIPTION: SEQ ID NO: 6:

Asp Gln Glu Val Pro Glu Lys Pro
  1               5

(2) INFORMATION FOR SEQ ID NO: 7:

(i) SEQUENCE CHARACTERISTICS:
              (A) LENGTH: 23 base pairs
              (B) TYPE: nucleic acid
              (C) STRANDEDNESS: single
              (D) TOPOLOGY: linear (ii) MOLECULE TYPE: cDNA (xi) SEQUENCE DESCRIPTION: SEQ ID NO: 7:

GAYCARGARG TNCCDGARAA RCC                                                        23

(2) INFORMATION FOR SEQ ID NO: 8:

(i) SEQUENCE CHARACTERISTICS:
              (A) LENGTH: 7 amino acids
              (B) TYPE: amino acid
              (D) TOPOLOGY: linear (ii) MOLECULE TYPE: peptide (v) FRAGMENT TYPE: internal (xi) SEQUENCE DESCRIPTION: SEQ ID NO: 8:

Tyr Ile Leu Tyr Cys Glu Gly
  1               5

(2) INFORMATION FOR SEQ ID NO: 9:

(i) SEQUENCE CHARACTERISTICS:
              (A) LENGTH: 20 base pairs
              (B) TYPE: nucleic acid
              (C) STRANDEDNESS: single
              (D) TOPOLOGY: linear (ii) MOLECULE TYPE: cDNA (xi) SEQUENCE DESCRIPTION: SEQ ID NO: 9:

TACATTCTNT AYTGTGARGG                                                    20

(2) INFORMATION FOR SEQ ID NO: 10:

(i) SEQUENCE CHARACTERISTICS:
        (A) LENGTH: 8 amino acids
        (B) TYPE: amino acid
        (D) TOPOLOGY: linear (ii) MOLECULE TYPE: peptide (v) FRAGMENT TYPE: internal (xi) SEQUENCE DESCRIPTION: SEQ ID NO: 10:

Met Ile Leu Lys Ala Gln Lys Gly
 1               5

(2) INFORMATION FOR SEQ ID NO: 11:

(i) SEQUENCE CHARACTERISTICS:
        (A) LENGTH: 29 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO: 11:

GGGGATCCYT TYTGNGCYTT YAADATCAT                                          29

(2) INFORMATION FOR SEQ ID NO: 12:

(i) SEQUENCE CHARACTERISTICS:
        (A) LENGTH: 29 base pairs
        (B) TYPE: nucleic acid
        (C) STRANDEDNESS: single
        (D) TOPOLOGY: linear (ii) MOLECULE TYPE: cDNA (iv) ANTI-SENSE: yes (xi) SEQUENCE DESCRIPTION: SEQ ID NO: 12:

GGGGATCCYT TYTGNGCYTT YAGDATCAT                                          29

(2) INFORMATION FOR SEQ ID NO: 13:

(i) SEQUENCE CHARACTERISTICS:
        (A) LENGTH: 26 base pairs
        (B) TYPE: nucleic acid
        (C) STRANDEDNESS: single
        (D) TOPOLOGY: linear (ii) MOLECULE TYPE: cDNA (iv) ANTI-SENSE: yes (xi) SEQUENCE DESCRIPTION: SEQ ID NO: 13:

GGGGATCCYT CACARTAYAA DATRTA                                             26

(2) INFORMATION FOR SEQ ID NO: 14:

(i) SEQUENCE CHARACTERISTICS:
        (A) LENGTH: 26 base pairs
        (B) TYPE: nucleic acid (C) STRANDEDNESS: single
        (D) TOPOLOGY: linear (ii) MOLECULE TYPE: cDNA (iv) ANTI-SENSE: yes (xi) SEQUENCE DESCRIPTION: SEQ ID NO: 14:

GGGGATCCYT CACARTANAG DATRTA                                                26

(2) INFORMATION FOR SEQ ID NO: 15:

(i) SEQUENCE CHARACTERISTICS:
        (A) LENGTH: 7 amino acids
        (B) TYPE: amino acid
        (D) TOPOLOGY: linear (ii) MOLECULE TYPE: peptide (v) FRAGMENT TYPE: internal (xi) SEQUENCE DESCRIPTION: SEQ ID NO: 15:

Gly Gln Arg Val Val Phe Ile
 1               5

(2) INFORMATION FOR SEQ ID NO: 16:

(i) SEQUENCE CHARACTERISTICS:
        (A) LENGTH: 29 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO: 16:

GGGCTCGAGG CCAGCGTGTC GTGTTCATC                                             29

(2) INFORMATION FOR SEQ ID NO: 17:

(i) SEQUENCE CHARACTERISTICS:
        (A) LENGTH: 7 amino acids
        (B) TYPE: amino acid
        (D) TOPOLOGY: linear (ii) MOLECULE TYPE: peptide (v) FRAGMENT TYPE: internal (xi) SEQUENCE DESCRIPTION: SEQ ID NO: 17:

Gln Pro Ser Pro Val Arg Asp
 1               5

(2) INFORMATION FOR SEQ ID NO: 18:

(i) SEQUENCE CHARACTERISTICS:
        (A) LENGTH: 30 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO: 18:

GGGCTCGAGC AGCCGTCCCC GGTGAGGGAC                                            30

(2) INFORMATION FOR SEQ ID NO: 19:

(i) SEQUENCE CHARACTERISTICS:

(A) LENGTH: 7 amino acids
        (B) TYPE: amino acid
        (D) TOPOLOGY: linear (ii) MOLECULE TYPE: peptide (v) FRAGMENT TYPE: internal (xi) SEQUENCE DESCRIPTION: SEQ ID NO: 19:

Gln Glu Leu Ala Glu Asp Phe
 1               5

(2) INFORMATION FOR SEQ ID NO: 20:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO: 20:

CARGARGCNC TDGARGAYTT                                              20

(2) INFORMATION FOR SEQ ID NO: 21:

(i) SEQUENCE CHARACTERISTICS:
        (A) LENGTH: 34 base pairs
        (B) TYPE: nucleic acid
        (C) STRANDEDNESS: single
        (D) TOPOLOGY: linear (ii) MOLECULE TYPE: cDNA (iv) ANTI-SENSE: yes (xi) SEQUENCE DESCRIPTION: SEQ ID NO: 21:

GGGGAGATCT CGAGAGGAAG CTGCGGCCGC TGCA                              34

(2) INFORMATION FOR SEQ ID NO: 22:

(i) SEQUENCE CHARACTERISTICS:
        (A) LENGTH: 58 base pairs
        (B) TYPE: nucleic acid
        (C) STRANDEDNESS: single
        (D) TOPOLOGY: linear (ii) MOLECULE TYPE: cDNA (iv) ANTI-SENSE: yes (xi) SEQUENCE DESCRIPTION: SEQ ID NO: 22:

CGAATACGAC TCACTATAGG AAGCTGCGGC CGCTGCAGTA CTTTTTTTTT TTTTTTTT    58

(2) INFORMATION FOR SEQ ID NO: 23:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: cDNA (iv) ANTI-SENSE: yes (xi) SEQUENCE DESCRIPTION: SEQ ID NO: 23:

CGAATACGAC TCACTATAGG                                              20

(2) INFORMATION FOR SEQ ID NO: 24:

(i) SEQUENCE CHARACTERISTICS:
        (A) LENGTH: 26 base pairs
        (B) TYPE: nucleic acid
        (C) STRANDEDNESS: single
        (D) TOPOLOGY: linear (ii) MOLECULE TYPE: cDNA (iv) ANTI-SENSE: yes (xi) SEQUENCE DESCRIPTION: SEQ ID NO: 24:

CCTAGGAGGA AGCTGCGGCC GCTGCA                                    26

(2) INFORMATION FOR SEQ ID NO: 25:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO: 25:

GGGTCTAGAG GTACCGTCCG                                            20

(2) INFORMATION FOR SEQ ID NO: 26:

(i) SEQUENCE CHARACTERISTICS:
        (A) LENGTH: 30 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO: 26:

GGGTCTAGAG GTACCGTCCG ATCGATCATT                              30

(2) INFORMATION FOR SEQ ID NO: 27:

(i) SEQUENCE CHARACTERISTICS:
        (A) LENGTH: 13 base pairs
        (B) TYPE: nucleic acid
        (C) STRANDEDNESS: single
        (D) TOPOLOGY: linear (ii) MOLECULE TYPE: cDNA (iv) ANTI-SENSE: yes (xi) SEQUENCE DESCRIPTION: SEQ ID NO: 27:

AATGATCGAT GCT                                                            13

(2) INFORMATION FOR SEQ ID NO: 28:

(i) SEQUENCE CHARACTERISTICS:
        (A) LENGTH: 10 amino acids
        (B) TYPE: amino acid
        (D) TOPOLOGY: linear (ii) MOLECULE TYPE: peptide (v) FRAGMENT TYPE: internal (xi) SEQUENCE DESCRIPTION: SEQ ID NO: 28:

Lys Trp Tyr Leu Lys Ala Met Thr Ala Asp (2) INFORMATION FOR SEQ ID NO: 29:

(i) SEQUENCE CHARACTERISTICS:
        (A) LENGTH: 30 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO: 29:

```
AARTGGTAYC TNAARGCNAT GACAGCAGAC                              30
```

(2) INFORMATION FOR SEQ ID NO: 30:

(i) SEQUENCE CHARACTERISTICS:
        (A) LENGTH: 7 amino acids
        (B) TYPE: amino acid
        (D) TOPOLOGY: linear (ii) MOLECULE TYPE: peptide (v) FRAGMENT TYPE: internal (xi) SEQUENCE DESCRIPTION: SEQ ID NO: 30:

```
Gln Glu Val Pro Glu Lys Pro
  1               5
```

(2) INFORMATION FOR SEQ ID NO: 31:

(i) SEQUENCE CHARACTERISTICS:
        (A) LENGTH: 29 base pairs
        (B) TYPE: nucleic acid
        (C) STRANDEDNESS: single
        (D) TOPOLOGY: linear (ii) MOLECULE TYPE: cDNA (iv) ANTI-SENSE: yes (xi) SEQUENCE DESCRIPTION: SEQ ID NO: 31:

```
GGGGATCCAG GCTTCTCAGG CACCTCCTG                               29
```

(2) INFORMATION FOR SEQ ID NO: 32:

(i) SEQUENCE CHARACTERISTICS:
        (A) LENGTH: 6 amino acids
        (B) TYPE: amino acid
        (D) TOPOLOGY: linear (ii) MOLECULE TYPE: peptide (v) FRAGMENT TYPE: internal (xi) SEQUENCE DESCRIPTION: SEQ ID NO: 32:

```
Asp Ser Val Thr Pro Met
  1               5
```

(2) INFORMATION FOR SEQ ID NO: 33:

(i) SEQUENCE CHARACTERISTICS:
        (A) LENGTH: 25 base pairs
        (B) TYPE: nucleic acid
        (C) STRANDEDNESS: single
        (D) TOPOLOGY: linear (ii) MOLECULE TYPE: cDNA (iv) ANTI-SENSE: yes (xi) SEQUENCE DESCRIPTION: SEQ ID NO: 33:

GGGGATCCAT GGGAGTCACT GAGTC                                              25

(2) INFORMATION FOR SEQ ID NO: 34:

(i) SEQUENCE CHARACTERISTICS:
            (A) LENGTH: 8 amino acids
            (B) TYPE: amino acid
            (D) TOPOLOGY: linear (ii) MOLECULE TYPE: peptide (v) FRAGMENT TYPE: internal (xi) SEQUENCE DESCRIPTION: SEQ ID NO: 34:

Met Lys Thr Leu Leu Leu Thr Ile
 1               5

(2) INFORMATION FOR SEQ ID NO: 35:

(i) SEQUENCE CHARACTERISTICS:
            (A) LENGTH: 31 base pairs
            (B) TYPE: nucleic acid
            (C) STRANDEDNESS: single
            (D) TOPOLOGY: linear (ii) MOLECULE TYPE: cDNA (xi) SEQUENCE DESCRIPTION: SEQ ID NO: 35:

CCTCGAGATG AAGACCCTGC TCCTCACCAT C                                       31

(2) INFORMATION FOR SEQ ID NO: 36:

(i) SEQUENCE CHARACTERISTICS:
            (A) LENGTH: 33 base pairs
            (B) TYPE: nucleic acid
            (C) STRANDEDNESS: single
            (D) TOPOLOGY: linear (ii) MOLECULE TYPE: cDNA (iv) ANTI-SENSE: yes (xi) SEQUENCE DESCRIPTION: SEQ ID NO: 36:

GGGAGATCTC AGAGGGTCAT GGAGCTGCTG CCC                                     33

(2) INFORMATION FOR SEQ ID NO: 37:

(i) SEQUENCE CHARACTERISTICS:
            (A) LENGTH: 35 base pairs
            (B) TYPE: nucleic acid
            (C) STRANDEDNESS: single
            (D) TOPOLOGY: linear (ii) MOLECULE TYPE: cDNA (xi) SEQUENCE DESCRIPTION: SEQ ID NO: 37:

CCCTCGAGGA CACTGTGGCT GTGTCAGGGA AATGG                                   35

(2) INFORMATION FOR SEQ ID NO: 38:

(i) SEQUENCE CHARACTERISTICS:
            (A) LENGTH: 18 base pairs
            (B) TYPE: nucleic acid
            (C) STRANDEDNESS: single
            (D) TOPOLOGY: linear (ii) MOLECULE TYPE: cDNA (xi) SEQUENCE DESCRIPTION: SEQ ID NO: 38:

CCTGAGAAGC CTGACTCA                                                        18

(2) INFORMATION FOR SEQ ID NO: 39:

(i) SEQUENCE CHARACTERISTICS:
               (A) LENGTH: 21 base pairs
               (B) TYPE: nucleic acid
               (C) STRANDEDNESS: single
               (D) TOPOLOGY: linear (ii) MOLECULE TYPE: cDNA (xi) SEQUENCE DESCRIPTION: SEQ ID NO: 39:

ACTGCATACG AGGGCCAGCG T                                                    21

(2) INFORMATION FOR SEQ ID NO: 40:

(i) SEQUENCE CHARACTERISTICS:
               (A) LENGTH: 29 base pairs
               (B) TYPE: nucleic acid
               (C) STRANDEDNESS: single
               (D) TOPOLOGY: linear (ii) MOLECULE TYPE: cDNA (xi) SEQUENCE DESCRIPTION: SEQ ID NO: 40:

GGGAATTCCA GCCGTCCCCG GTGAGGGAC                                            29

(2) INFORMATION FOR SEQ ID NO: 41:

(i) SEQUENCE CHARACTERISTICS:
               (A) LENGTH: 21 base pairs
               (B) TYPE: nucleic acid
               (C) STRANDEDNESS: single
               (D) TOPOLOGY: linear (ii) MOLECULE TYPE: cDNA (xi) SEQUENCE DESCRIPTION: SEQ ID NO: 41:

ATCACCATGC TGACAAATGG T                                                    21

(2) INFORMATION FOR SEQ ID NO: 42:

(i) SEQUENCE CHARACTERISTICS:
               (A) LENGTH: 21 base pairs
               (B) TYPE: nucleic acid
               (C) STRANDEDNESS: single
               (D) TOPOLOGY: linear (ii) MOLECULE TYPE: cDNA (iv) ANTI-SENSE: yes (xi) SEQUENCE DESCRIPTION: SEQ ID NO: 42:

AATCTCCTGG TTCAATCCTT T                                                    21

(2) INFORMATION FOR SEQ ID NO: 43:

(i) SEQUENCE CHARACTERISTICS:
               (A) LENGTH: 21 base pairs
               (B) TYPE: nucleic acid
               (C) STRANDEDNESS: single
               (D) TOPOLOGY: linear (ii) MOLECULE TYPE: cDNA (iv) ANTI-SENSE: yes (xi) SEQUENCE DESCRIPTION: SEQ ID NO: 43:

ACGCTGGCCC TCGTATGCAG T                                              21

(2) INFORMATION FOR SEQ ID NO: 44:

(i) SEQUENCE CHARACTERISTICS:
            (A) LENGTH: 25 base pairs
            (B) TYPE: nucleic acid
            (C) STRANDEDNESS: single
            (D) TOPOLOGY: linear (ii) MOLECULE TYPE: cDNA (iv) ANTI-SENSE: yes (xi) SEQUENCE DESCRIPTION: SEQ ID NO: 44:

GGGGATCCAT GGGAGTCACT GAGTC                                          25

(2) INFORMATION FOR SEQ ID NO: 45:

(i) SEQUENCE CHARACTERISTICS:
            (A) LENGTH: 21 base pairs
            (B) TYPE: nucleic acid
            (C) STRANDEDNESS: single
            (D) TOPOLOGY: linear (ii) MOLECULE TYPE: cDNA (iv) ANTI-SENSE: yes (xi) SEQUENCE DESCRIPTION: SEQ ID NO: 45:

GTGCAGGACC ACCGTGATGT T                                              21

(2) INFORMATION FOR SEQ ID NO: 46:

(i) SEQUENCE CHARACTERISTICS:
            (A) LENGTH: 10 amino acids
            (B) TYPE: amino acid
            (D) TOPOLOGY: linear (ii) MOLECULE TYPE: peptide (v) FRAGMENT TYPE: internal (xi) SEQUENCE DESCRIPTION: SEQ ID NO: 46:

Glu Phe Asp Thr Val Ala Val Ser Gly Lys
  1               5                  10

(2) INFORMATION FOR SEQ ID NO: 47:

(i) SEQUENCE CHARACTERISTICS:
            (A) LENGTH: 31 base pairs
            (B) TYPE: nucleic acid
            (C) STRANDEDNESS: single
            (D) TOPOLOGY: linear (ii) MOLECULE TYPE: cDNA (xi) SEQUENCE DESCRIPTION: SEQ ID NO: 47:

GGAATTCGAC ACTGTGGCTG TGTCAGGGAA A                                   31

(2) INFORMATION FOR SEQ ID NO: 48:

(i) SEQUENCE CHARACTERISTICS:
            (A) LENGTH: 7 amino acids
            (B) TYPE: amino acid
            (D) TOPOLOGY: linear (ii) MOLECULE TYPE: peptide (v) FRAGMENT TYPE: internal (xi) SEQUENCE DESCRIPTION: SEQ ID NO: 48:

Glu Phe Ser Arg Ala Lys Gly
  1               5

(2) INFORMATION FOR SEQ ID NO: 49:

(i) SEQUENCE CHARACTERISTICS:
            (A) LENGTH: 22 base pairs
            (B) TYPE: nucleic acid
            (C) STRANDEDNESS: single
            (D) TOPOLOGY: linear (ii) MOLECULE TYPE: cDNA (xi) SEQUENCE DESCRIPTION: SEQ ID NO: 49:

GAGTTCTCAA GAGCCAAAGG AT                                                22

(2) INFORMATION FOR SEQ ID NO: 50:

(i) SEQUENCE CHARACTERISTICS:
            (A) LENGTH: 22 base pairs
            (B) TYPE: nucleic acid
            (C) STRANDEDNESS: single
            (D) TOPOLOGY: linear (ii) MOLECULE TYPE: cDNA (iv) ANTI-SENSE: yes (xi) SEQUENCE DESCRIPTION: SEQ ID NO: 50:

ATCCTTTGGC TATTGAGAAC TC                                                22

(2) INFORMATION FOR SEQ ID NO: 51:

(i) SEQUENCE CHARACTERISTICS:
            (A) LENGTH: 31 base pairs
            (B) TYPE: nucleic acid
            (C) STRANDEDNESS: single
            (D) TOPOLOGY: linear (ii) MOLECULE TYPE: cDNA (iv) ANTI-SENSE: yes (xi) SEQUENCE DESCRIPTION: SEQ ID NO: 51:

GGGAGATCTA CTGTCCTCCT GGAGAGCAGG T                                      31

(2) INFORMATION FOR SEQ ID NO: 52:

(i) SEQUENCE CHARACTERISTICS:
            (A) LENGTH: 7 amino acids
            (B) TYPE: amino acid
            (D) TOPOLOGY: linear (ii) MOLECULE TYPE: peptide (v) FRAGMENT TYPE: internal (xi) SEQUENCE DESCRIPTION: SEQ ID NO: 52:

Thr Cys Ser Pro Gly Gly Gln
  1               5

(2) INFORMATION FOR SEQ ID NO: 53:

(i) SEQUENCE CHARACTERISTICS:
        (A) LENGTH: 15 amino acids
        (B) TYPE: amino acid
        (D) TOPOLOGY: linear (ii) MOLECULE TYPE: peptide (v) FRAGMENT TYPE: internal (xi) SEQUENCE DESCRIPTION: SEQ ID NO: 53:

Met Gly His His His His His His Glu Phe Asp Thr Val Ala Val
 1               5                  10                  15

(2) INFORMATION FOR SEQ ID NO: 54:

(i) SEQUENCE CHARACTERISTICS:
        (A) LENGTH: 37 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO: 54:

CCCCTCGAGC CACATGAAGA CCCTGCTCCT CACCATC                           37

(2) INFORMATION FOR SEQ ID NO: 55:

(i) SEQUENCE CHARACTERISTICS:
        (A) LENGTH: 27 amino acids
        (B) TYPE: amino acid
        (D) TOPOLOGY: linear (ii) MOLECULE TYPE: peptide (v) FRAGMENT TYPE: internal (xi) SEQUENCE DESCRIPTION: SEQ ID NO: 55:

Glu Phe Ser Arg Ala Asn Lys Gly Leu Asn Gln Glu Ile Leu Glu Leu
 1               5                  10                  15

Ala Gln Ser Glu Thr Cys Ser Pro Gly Gly Gln
            20                  25

(2) INFORMATION FOR SEQ ID NO: 56:

(i) SEQUENCE CHARACTERISTICS:
        (A) LENGTH: 78 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO: 56:

GAATTCTCAA GAGCCAAAGG ATTGAACCAG GAGATTTTGG AACTCGCGCA GAGCGAAACC   60

TGCTCTCCAG GAGGACAG                                                78

(2) INFORMATION FOR SEQ ID NO: 57:

(i) SEQUENCE CHARACTERISTICS:
        (A) LENGTH: 26 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO: 57:

```
GGGAATTCTC AAGAGCCAAA AGGATT                                                    26
```

(2) INFORMATION FOR SEQ ID NO: 58:

(i) SEQUENCE CHARACTERISTICS:
        (A) LENGTH: 14 amino acids
        (B) TYPE: amino acid
        (D) TOPOLOGY: linear (ii) MOLECULE TYPE: peptide (v) FRAGMENT TYPE: internal (xi) SEQUENCE DESCRIPTION: SEQ ID NO: 58:

```
Glu Thr Cys Ser Pro Gly Gly Gln His His His His His His
 1               5                  10
```

(2) INFORMATION FOR SEQ ID NO: 59:

(i) SEQUENCE CHARACTERISTICS:
        (A) LENGTH: 52 base pairs
        (B) TYPE: nucleic acid
        (C) STRANDEDNESS: single
        (D) TOPOLOGY: linear (ii) MOLECULE TYPE: cDNA (iv) ANTI-SENSE: yes (xi) SEQUENCE DESCRIPTION: SEQ ID NO: 59:

```
TTTAGATCTA GTGGTGGTGG TGGTGGTGCT GTCCTCCTGG AGAGCAGGTT TC          52
```

(2) INFORMATION FOR SEQ ID NO: 60:

(i) SEQUENCE CHARACTERISTICS:
        (A) LENGTH: 23 base pairs
        (B) TYPE: nucleic acid
        (C) STRANDEDNESS: single
        (D) TOPOLOGY: linear (ii) MOLECULE TYPE: cDNA (iv) ANTI-SENSE: yes (xi) SEQUENCE DESCRIPTION: SEQ ID NO: 60:

```
TTTAGATCTA GTGGTGGTGG TGG                                          23
```

(2) INFORMATION FOR SEQ ID NO: 61:

(i) SEQUENCE CHARACTERISTICS:
        (A) LENGTH: 145 amino acids
        (B) TYPE: amino acid
        (D) TOPOLOGY: linear (ii) MOLECULE TYPE: peptide (v) FRAGMENT TYPE: internal (xi) SEQUENCE DESCRIPTION: SEQ ID NO: 61:

```
Asp Thr Val Ala Val Ser Gly Lys Trp Tyr Leu Lys Ala Met Thr Ala
 1               5                  10                  15

Asp Gln Glu Val Pro Glu Lys Pro Asp Ser Val Thr Pro Met Ile Leu
            20                  25                  30

Lys Ala Gln Lys Gly Gly Asn Leu Glu Ala Lys Ile Thr Met Leu Thr
        35                  40                  45

Asn Gly Gln Cys Gln Asn Ile Thr Val Val Leu His Lys Thr Ser Glu
    50                  55                  60
```

```
Pro Gly Lys Tyr Thr Ala Tyr Glu Gly Gln Arg Val Val Phe Ile Gln
 65                  70                  75                  80

Pro Ser Pro Val Arg Asp Arg Tyr Ile Leu Tyr Cys Glu Gly Asp Leu
                 85                  90                  95

Leu Pro Gln Ala His Leu Leu His Pro Ser Cys His His His Ser Leu
                100                 105                 110

Leu Gln Ala His His Arg Leu Leu Leu Pro His Lys Lys Leu Leu Gln
                115                 120                 125

Gly Asp Pro Cys Val Ala Gln Trp Phe Ser Ala Cys Leu Gly Leu Arg
            130                 135                 140

Ala
145

(2) INFORMATION FOR SEQ ID NO: 62:

(i) SEQUENCE CHARACTERISTICS:
        (A) LENGTH: 144 amino acids
        (B) TYPE: amino acid
        (D) TOPOLOGY: linear (ii) MOLECULE TYPE: peptide (v) FRAGMENT TYPE: internal (xi) SEQUENCE DESCRIPTION: SEQ ID NO: 62:

Asp Thr Val Ala Val Ser Gly Lys Trp Tyr Leu Lys Ala Met Thr Ala
  1               5                  10                  15

Asp Gln Glu Val Pro Glu Lys Pro Asp Ser Val Thr Pro Met Ile Leu
                 20                  25                  30

Lys Ala Gln Lys Gly Gly Asn Leu Glu Ala Lys Ile Thr Met Leu Thr
                 35                  40                  45

Asn Gly Gln Cys Gln Asn Ile Thr Val Val Leu His Lys Thr Ser Glu
 50                  55                  60

Pro Gly Lys Tyr Thr Ala Tyr Glu Gly Gln Arg Val Val Phe Ile Gln
 65                  70                  75                  80

Pro Ser Pro Val Arg Asp His Tyr Ile Leu Tyr Cys Glu Gly Glu Leu
                 85                  90                  95

His Gly Arg Gln Ile Arg Met Ala Lys Leu Leu Gly Arg Asp Pro Glu
                100                 105                 110

Gln Ala His His Arg Leu Leu Leu Pro His Lys Lys Leu Leu Gln Gly
                115                 120                 125

Asp Pro Cys Val Ala Gln Trp Phe Ser Ala Cys Leu Gly Leu Arg Ala
            130                 135                 140

(2) INFORMATION FOR SEQ ID NO: 63:

(i) SEQUENCE CHARACTERISTICS:
        (A) LENGTH: 105 amino acids
        (B) TYPE: amino acid
        (D) TOPOLOGY: linear (ii) MOLECULE TYPE: peptide (v) FRAGMENT TYPE: internal (xi) SEQUENCE DESCRIPTION: SEQ ID NO: 63:

Pro Glu Lys Pro Asp Ser Val Thr Pro Met Ile Leu Lys Ala Gln Lys
  1               5                  10                  15

Gly Gly Asn Leu Glu Ala Lys Ile Thr Met Leu Thr Asn Gly Gln Cys
                 20                  25                  30
```

```
Gln Asn Ile Thr Val Val Leu His Lys Thr Ser Glu Pro Gly Lys Tyr
            35                  40                  45

Thr Ala Tyr Glu Gly Gln Arg Val Val Phe Ile Gln Pro Ser Pro Val
        50                  55                  60

Arg Asp His Tyr Ile Leu Tyr Cys Glu Gly Glu Leu His Gly Arg Gln
65                  70                  75                  80

Ile Arg Met Ala Lys Gly Leu Asn Gln Glu Ile Leu Glu Leu Ala Gln
                85                  90                  95

Ser Glu Thr Cys Ser Pro Gly Gly Gln
                100                 105

(2) INFORMATION FOR SEQ ID NO: 64:

(i) SEQUENCE CHARACTERISTICS:
        (A) LENGTH: 11 amino acids
        (B) TYPE: amino acid
        (D) TOPOLOGY: linear (ii) MOLECULE TYPE: peptide (v) FRAGMENT TYPE: internal (xi) SEQUENCE DESCRIPTION: SEQ ID NO: 64:

Met Ala Lys Leu Leu Gly Arg Asp Pro Glu Gln
1               5                   10

(2) INFORMATION FOR SEQ ID NO: 65:

(i) SEQUENCE CHARACTERISTICS:
        (A) LENGTH: 38 amino acids
        (B) TYPE: amino acid
        (D) TOPOLOGY: linear (ii) MOLECULE TYPE: peptide (v) FRAGMENT TYPE: internal (xi) SEQUENCE DESCRIPTION: SEQ ID NO: 65:

Met Ala Lys Leu Leu Gly Arg Asp Pro Glu Gln Ser Gln Glu Ala Leu
1               5                   10                  15

Glu Asp Phe Glu Phe Ser Ala Lys Gly Leu Asn Gln Glu Ile Leu Glu
                20                  25                  30

Leu Ala Gln Ser Glu Thr
                35

(2) INFORMATION FOR SEQ ID NO: 66:

(i) SEQUENCE CHARACTERISTICS:
        (A) LENGTH: 8 amino acids
        (B) TYPE: amino acid
        (D) TOPOLOGY: linear (ii) MOLECULE TYPE: peptide (v) FRAGMENT TYPE: internal (xi) SEQUENCE DESCRIPTION: SEQ ID NO: 66:

Asp Pro Glu Gln Ser Glu Glu Ala
1               5

(2) INFORMATION FOR SEQ ID NO: 67:

(i) SEQUENCE CHARACTERISTICS:
        (A) LENGTH: 791 base pairs
        (B) TYPE: nucleic acid
        (C) STRANDEDNESS: single
```

(D) TOPOLOGY: linear (ii) MOLECULE TYPE: cDNA (ix) FEATURE:
    (A) NAME/KEY: CDS
    (B) LOCATION: 195..734

(ix) FEATURE:
    (A) NAME/KEY: mat_peptide
    (B) LOCATION: 253..734

(xi) SEQUENCE DESCRIPTION: SEQ ID NO: 67:

```
AGAGCTGGAC CCGTGTGTGT GCTGGCCAAT GAGCCCTGGA GGGTCCGGCT CCAGAGTACC        60

CTCTTGGCAC AGGGCCGAGT CCATCGGGAC AGATGAACCT AGAGGACTCC ACTGCCCTCC       120

CATCCACGGG GCCGGGTCAC CAGACTCTGC AAGTCTCCAG CTGTCGCCAA ACCCAGACAG       180

AAGGTGCTGT GGAC ATG CAG CTC CTA CTG CTG ACC GTG GGC CTG GCA CTG        230
              Met Gln Leu Leu Leu Leu Thr Val Gly Leu Ala Leu
              -19             -15                 -10

ATC TGT GGC CTC CAG GCT CAG GAG GGA AAC CAT GAG GAG CCC CAG GGA        278
Ile Cys Gly Leu Gln Ala Gln Glu Gly Asn His Glu Glu Pro Gln Gly
        -5                 1                 5

GGC CTA GAG GAG CTG TCT GGG AGG TGG CAC TCC GTT GCC CTG GCC TCC        326
Gly Leu Glu Glu Leu Ser Gly Arg Trp His Ser Val Ala Leu Ala Ser
 10                 15                 20                 25

AAC AAG TCC GAT CTG ATC AAA CCC TGG GGG CAC TTC AGG GTT TTC ATC        374
Asn Lys Ser Asp Leu Ile Lys Pro Trp Gly His Phe Arg Val Phe Ile
             30                 35                 40

CAC AGC ATG AGC GCA AAG GAC GGC AAC CTG CAC GGG GAT ATC CTT ATA        422
His Ser Met Ser Ala Lys Asp Gly Asn Leu His Gly Asp Ile Leu Ile
             45                 50                 55

CCG CAG GAC GGC CAG TGC GAG AAA GTC TCC CTC ACT GCG TTC AAG ACT        470
Pro Gln Asp Gly Gln Cys Glu Lys Val Ser Leu Thr Ala Phe Lys Thr
         60                 65                 70

GCC ACC AGC AAC AAA TTT GAC CTG GAG TAC TGG GGA CAC AAT GAC CTG        518
Ala Thr Ser Asn Lys Phe Asp Leu Glu Tyr Trp Gly His Asn Asp Leu
         75                 80                 85

TAC CTG GCA GAG GTA GAC CCC AAG AGC TAC CTG ATT CTC TAC ATG ATC        566
Tyr Leu Ala Glu Val Asp Pro Lys Ser Tyr Leu Ile Leu Tyr Met Ile
 90                 95                 100                105

AAC CAG TAC AAC GAT GAC ACC AGC CTG GTG GCT CAC TTG ATG GTC CGG        614
Asn Gln Tyr Asn Asp Asp Thr Ser Leu Val Ala His Leu Met Val Arg
             110                 115                 120

GAC CTC AGC AGG CAG CAG GAC TTC CTG CCG GCA TTC GAA TCT GTA TGT        662
Asp Leu Ser Arg Gln Gln Asp Phe Leu Pro Ala Phe Glu Ser Val Cys
         125                 130                 135

GAA GAC ATC GGT CTG CAC AAG GAC CAG ATT GTG GTT CTG AGC GAT GAC        710
Glu Asp Ile Gly Leu His Lys Asp Gln Ile Val Val Leu Ser Asp Asp
         140                 145                 150

GAT CGC TGC CAG GGT TCC AGA GAC TAGGGCCTCA GCCACGCAGA GAGCCAAGCA       764
Asp Arg Cys Gln Gly Ser Arg Asp
 155                 160

GCAGGATCTC ACCTGCCTGA GTACGGT                                           791
```

(2) INFORMATION FOR SEQ ID NO: 68:

(i) SEQUENCE CHARACTERISTICS:
        (A) LENGTH: 180 amino acids
        (B) TYPE: amino acid
        (D) TOPOLOGY: linear (ii) MOLECULE TYPE: protein (xi) SEQUENCE DESCRIPTION: SEQ ID NO: 68:

```
Met Gln Leu Leu Leu Leu Thr Val Gly Leu Ala Leu Ile Cys Gly Leu
-19              -15              -10                   -5

Gln Ala Gln Glu Gly Asn His Glu Glu Pro Gln Gly Gly Leu Glu Glu
             1               5                  10

Leu Ser Gly Arg Trp His Ser Val Ala Leu Ala Ser Asn Lys Ser Asp
         15              20                  25

Leu Ile Lys Pro Trp Gly His Phe Arg Val Phe Ile His Ser Met Ser
         30              35                  40                  45

Ala Lys Asp Gly Asn Leu His Gly Asp Ile Leu Ile Pro Gln Asp Gly
                 50                  55                  60

Gln Cys Glu Lys Val Ser Leu Thr Ala Phe Lys Thr Ala Thr Ser Asn
             65                  70                  75

Lys Phe Asp Leu Glu Tyr Trp Gly His Asn Asp Leu Tyr Leu Ala Glu
         80                  85                  90

Val Asp Pro Lys Ser Tyr Leu Ile Leu Tyr Met Ile Asn Gln Tyr Asn
         95             100                 105

Asp Asp Thr Ser Leu Val Ala His Leu Met Val Arg Asp Leu Ser Arg
110                 115                 120                 125

Gln Gln Asp Phe Leu Pro Ala Phe Glu Ser Val Cys Glu Asp Ile Gly
                130                 135                 140

Leu His Lys Asp Gln Ile Val Val Leu Ser Asp Asp Arg Cys Gln
                145                 150                 155

Gly Ser Arg Asp
        160
```

(2) INFORMATION FOR SEQ ID NO: 69:

(i) SEQUENCE CHARACTERISTICS:
        (A) LENGTH: 793 base pairs
        (B) TYPE: nucleic acid
        (C) STRANDEDNESS: single
        (D) TOPOLOGY: linear (ii) MOLECULE TYPE: cDNA (ix) FEATURE:
        (A) NAME/KEY: CDS
        (B) LOCATION: 3..533

(xi) SEQUENCE DESCRIPTION: SEQ ID NO: 69:

```
AC AGC ACC TTC TGT CTG GGT TTG GCA CTG ATC TGT GGC CTC CAG GCT        47
   Ser Thr Phe Cys Leu Gly Leu Ala Leu Ile Cys Gly Leu Gln Ala
     1               5                  10                  15

CAG GAG GGA AAC CAT GAG GAG CCC CAG GGA GGC CTA GAG GAG CTG TCT       95
Gln Glu Gly Asn His Glu Glu Pro Gln Gly Gly Leu Glu Glu Leu Ser
             20                  25                  30

GGG AGG TGG CAC TCC GTT GCC CTG GCC TCC AAC AAG TCC GAT CTG ATC      143
Gly Arg Trp His Ser Val Ala Leu Ala Ser Asn Lys Ser Asp Leu Ile
             35                  40                  45

AAA CCC TGG GGG CAC TTC AGG GTT TTC ATC CAC AGC ATG AGC GCA AAG      191
Lys Pro Trp Gly His Phe Arg Val Phe Ile His Ser Met Ser Ala Lys
         50                  55                  60

GAC GGC AAC CTG CAC GGG GAT ATC CTT ATA CCG CAG GAC GGC CAG TGC      239
Asp Gly Asn Leu His Gly Asp Ile Leu Ile Pro Gln Asp Gly Gln Cys
 65                  70                  75

GAG AAA GTC TCC CTC ACT GCG TTC AAG ACT GCC ACC AGC AAC AAA TTT      287
Glu Lys Val Ser Leu Thr Ala Phe Lys Thr Ala Thr Ser Asn Lys Phe
 80                  85                  90                  95
```

```
GAC CTG GAG TAC TGG GGA CAC AAT GAC CTG TAC CTG GCA GAG GTA GAC        335
Asp Leu Glu Tyr Trp Gly His Asn Asp Leu Tyr Leu Ala Glu Val Asp
                    100                 105                 110

CCC AAG AGC TAC CTG ATT CTC TAC ATG ATC AAC CAG TAC AAC GAT GAC        383
Pro Lys Ser Tyr Leu Ile Leu Tyr Met Ile Asn Gln Tyr Asn Asp Asp
                115                 120                 125

ACC AGC CTG GTG GCT CAC CTG ATG GTC CGG GAC CTC AGC AGG CAG CAG        431
Thr Ser Leu Val Ala His Leu Met Val Arg Asp Leu Ser Arg Gln Gln
            130                 135                 140

GAC TTC CTG CCG GCA TTC GAA TCT GTA TGT GAA GAC ATC GGT CTG CAC        479
Asp Phe Leu Pro Ala Phe Glu Ser Val Cys Glu Asp Ile Gly Leu His
        145                 150                 155

AAG GAC CAG ATT GTG GTT CTG AGC GAT GAC GAT CGC TGC CAG GGT TCC        527
Lys Asp Gln Ile Val Val Leu Ser Asp Asp Asp Arg Cys Gln Gly Ser
160                 165                 170                 175

AGA GAC TAGGGCCTCA GCCTACGCAG AGAGCCAAGC AGCAGGATCT CACCTGCCTG         583
Arg Asp

AGGACTCAGA CCTATAGGCT CGGGGGACAC CGTACTCAGC TCTGCGTCCC TCTCTGCGAA      643

CCCTCCAGGT GATCCCAGCA ACAACACCCA CCTGNGCTTC CATGTGCGGN CCTGTCCAGC      703

CTGCGCCCAC TCCCTGCCTG GGCAGCCACA CACTCCCCAG CCCCCTGCTA TGGTCCCTCC      763

TCGCATAATA AAGGACATTC CGTTCAAAAA                                        793

(2) INFORMATION FOR SEQ ID NO: 70:

(i) SEQUENCE CHARACTERISTICS:
        (A) LENGTH: 177 amino acids
        (B) TYPE: amino acid
        (D) TOPOLOGY: linear (ii) MOLECULE TYPE: protein (xi) SEQUENCE DESCRIPTION: SEQ ID NO: 70:

Ser Thr Phe Cys Leu Gly Leu Ala Leu Ile Cys Gly Leu Gln Ala Gln
 1               5                  10                  15

Glu Gly Asn His Glu Glu Pro Gln Gly Gly Leu Glu Glu Leu Ser Gly
                20                  25                  30

Arg Trp His Ser Val Ala Leu Ala Ser Asn Lys Ser Asp Leu Ile Lys
            35                  40                  45

Pro Trp Gly His Phe Arg Val Phe Ile His Ser Met Ser Ala Lys Asp
        50                  55                  60

Gly Asn Leu His Gly Asp Ile Leu Ile Pro Gln Asp Gly Gln Cys Glu
65                  70                  75                  80

Lys Val Ser Leu Thr Ala Phe Lys Thr Ala Thr Ser Asn Lys Phe Asp
                85                  90                  95

Leu Glu Tyr Trp Gly His Asn Asp Leu Tyr Leu Ala Glu Val Asp Pro
                100                 105                 110

Lys Ser Tyr Leu Ile Leu Tyr Met Ile Asn Gln Tyr Asn Asp Asp Thr
            115                 120                 125

Ser Leu Val Ala His Leu Met Val Arg Asp Leu Ser Arg Gln Gln Asp
        130                 135                 140

Phe Leu Pro Ala Phe Glu Ser Val Cys Glu Asp Ile Gly Leu His Lys
145                 150                 155                 160

Asp Gln Ile Val Val Leu Ser Asp Asp Asp Arg Cys Gln Gly Ser Arg
                165                 170                 175

Asp
```

(2) INFORMATION FOR SEQ ID NO: 71:

(i) SEQUENCE CHARACTERISTICS:
        (A) LENGTH: 774 base pairs
        (B) TYPE: nucleic acid
        (C) STRANDEDNESS: single
        (D) TOPOLOGY: linear (ii) MOLECULE TYPE: cDNA (ix) FEATURE:
        (A) NAME/KEY: CDS
        (B) LOCATION: 1..537

(xi) SEQUENCE DESCRIPTION: SEQ ID NO: 71:

```
CAG CTC CTA CTG CTG ACC GTG GGC CTG GCA CTG ATC TGT GGC CTC CAG        48
Gln Leu Leu Leu Leu Thr Val Gly Leu Ala Leu Ile Cys Gly Leu Gln
 1               5                  10                  15

GCT CAG GAG GGA AAC CAT GAG GAG CCC CAG GGA GGC CTA GAG GAG CTG        96
Ala Gln Glu Gly Asn His Glu Glu Pro Gln Gly Gly Leu Glu Glu Leu
                20                  25                  30

TCT GGG AGG TGG CAC TCC GTT GCC CTG GCC TCC AAC AAG TCC GAT CTG       144
Ser Gly Arg Trp His Ser Val Ala Leu Ala Ser Asn Lys Ser Asp Leu
            35                  40                  45

ACC AAA CCC TGG GGG CAC TTC AGG GTT TTC ATC CAC AGC ATG AGC GCA       192
Thr Lys Pro Trp Gly His Phe Arg Val Phe Ile His Ser Met Ser Ala
        50                  55                  60

AAG GAC GTC AAC CTG CAC GGG GAT ATC CTT ATA CCG CAG GAC GGC CAG       240
Lys Asp Val Asn Leu His Gly Asp Ile Leu Ile Pro Gln Asp Gly Gln
    65                  70                  75                  80

TGC GAG AAA GTC TCC CTC ACT GCG TTC AAG ACT GCC ACC AGC AAC AAA       288
Cys Glu Lys Val Ser Leu Thr Ala Phe Lys Thr Ala Thr Ser Asn Lys
                85                  90                  95

TTT GAC CTG GAG TAC TGG GGA CAC AAT GAC CTG TAC CTG GCA GAG GTA       336
Phe Asp Leu Glu Tyr Trp Gly His Asn Asp Leu Tyr Leu Ala Glu Val
                100                 105                 110

GAC CCC AAG AGC TAC CTG ATT CTC TAC ATG ATC AAC CAG TAC AAC GAT       384
Asp Pro Lys Ser Tyr Leu Ile Leu Tyr Met Ile Asn Gln Tyr Asn Asp
            115                 120                 125

GAC ACC AGC CTG GTG GCT CAC CTG ATG GTC CGG GAC CTC AGC AGG CAG       432
Asp Thr Ser Leu Val Ala His Leu Met Val Arg Asp Leu Ser Arg Gln
        130                 135                 140

CAG GAC TTC CTG CCG GCA TTC GAA TCT GTA TGT GAA GAC ATC GGT CTG       480
Gln Asp Phe Leu Pro Ala Phe Glu Ser Val Cys Glu Asp Ile Gly Leu
145                 150                 155                 160

CAC AAG GAC CAG ATT GTG GTT CTG AGC GAT GAC GAT CGC TGC CAG GGT       528
His Lys Asp Gln Ile Val Val Leu Ser Asp Asp Asp Arg Cys Gln Gly
                165                 170                 175

TCC AGA GAC TAGGGCCTCA GCCCACGCAG AGAGCCAAGC AGCAGGATCT               577
Ser Arg Asp

CACCTGCCTG AGGACTCAGA CCTATAGGCT CGGGGGACAC CGTACTCAGC TCTGCGTCCC     637

TCTCTGCGAA CCCTCCAGGT GATCCCAGCA ACAACACCCA CCTGCGCTTC CATGTGCGGC     697

CCTGTCCAGC CTGCGCCCAC TCCCTGCCTG GGCAGCCACA CACTCCCCAG CCCCCTGCTA     757

TGGTCCCTCC TCGCATA                                                    774
```

(2) INFORMATION FOR SEQ ID NO: 72:

(i) SEQUENCE CHARACTERISTICS:
        (A) LENGTH: 179 amino acids
        (B) TYPE: amino acid
        (D) TOPOLOGY: linear (ii) MOLECULE TYPE: protein (xi) SEQUENCE DESCRIPTION: SEQ ID NO: 72:

Gln Leu Leu Leu Leu Thr Val Gly Leu Ala Leu Ile Cys Gly Leu Gln
 1               5                  10                  15

Ala Gln Glu Gly Asn His Glu Glu Pro Gln Gly Gly Leu Glu Glu Leu
            20                  25                  30

Ser Gly Arg Trp His Ser Val Ala Leu Ala Ser Asn Lys Ser Asp Leu
        35                  40                  45

Thr Lys Pro Trp Gly His Phe Arg Val Phe Ile His Ser Met Ser Ala
    50                  55                  60

Lys Asp Val Asn Leu His Gly Asp Ile Leu Ile Pro Gln Asp Gly Gln
65                  70                  75                  80

Cys Glu Lys Val Ser Leu Thr Ala Phe Lys Thr Ala Thr Ser Asn Lys
                85                  90                  95

Phe Asp Leu Glu Tyr Trp Gly His Asn Asp Leu Tyr Leu Ala Glu Val
            100                 105                 110

Asp Pro Lys Ser Tyr Leu Ile Leu Tyr Met Ile Asn Gln Tyr Asn Asp
        115                 120                 125

Asp Thr Ser Leu Val Ala His Leu Met Val Arg Asp Leu Ser Arg Gln
    130                 135                 140

Gln Asp Phe Leu Pro Ala Phe Glu Ser Val Cys Glu Asp Ile Gly Leu
145                 150                 155                 160

His Lys Asp Gln Ile Val Val Leu Ser Asp Asp Arg Cys Gln Gly
                165                 170                 175

Ser Arg Asp (2) INFORMATION FOR SEQ ID NO: 73:

(i) SEQUENCE CHARACTERISTICS:
        (A) LENGTH: 998 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO: 73:

```
AGAGCTGGAC CCGTGTGTGT GCTGGCCAAT GAGCCCTGGA GGGTCCGGCT CCAGAGTACC      60
CTCTTGGCAC AGGGCCGAGT CCATCGGGAC AGATGAACCT AGAGGACTCC ACTGCCCTCC     120
CATCCACGGG GCCGGGTCAC CAGACTCTGC AAGTCTCCAG CTGTCGCCAA ACCCAGACAG     180
AAGGTGCTGT GGACATGCAG CTCCTACWGC ACYKWCYGTC TGGGYYTGGC ACTGATCTGT     240
GGCCTCCAGG CTCAGGAGGG AAACCATGAG GAGCCCCAGG GAGGCCTAGA GGAGCTGTCT     300
GGGAGGTGGC ACTCCGTTGC CCTGGCCTCC AACAAGTCCG ATCTGAYCAA ACCCTGGGGG     360
CACTTCAGGG TTTTCATCCA CAGCATGAGC GCAAAGGACG KCAACCTGCA CGGGGATATC     420
CTTATACCGC AGGACGGCCA GTGCGAGAAA GTCTCCCTCA CTGCGTTCAA GACTGCCACC     480
AGCAACAAAT TTGACCTGGA GTACTGGGGA CACAATGACC TGTACCTGGC AGAGGTAGAC     540
CCCAAGAGCT ACCTGATTCT CTACATGATC AACCAGTACA ACGATGACAC CAGCCTGGTG     600
GCTCACYTGA TGGTCCGGGA CCTCAGCAGG CAGCAGGACT TCCTGCCGGC ATTCGAATCT     660
GTATGTGAAG ACATCGGTCT GCACAAGGAC CAGATTGTGG TTCTGAGCGA TGACGATCGC     720
TGCCAGGGTT CCAGAGACTA GGGCCTCAGC CYACGCAGAG AGCCAAGCAG CAGGATCTCA     780
```

```
CCTGCCTGAG GACTCAGACC TATAGGCTCG GKGGACACCG TACTCAGCTC TGCGTCCCTC    840

TCTGCGAACC CTCCAGGTGA TCCCAGCAAC AACACCCACC TGCGCTTCCA TGTGCGGCCC    900

TGTCCAGCCT GCGCCCACTC CCTGCCTGGG CAGCCACACA CTCCCCAGCC CCCTGCTATG    960

GTCCCTCCTC GCATAATAAA GGACATTCCG TTCAAAAA                            998
```

(2) INFORMATION FOR SEQ ID NO: 74:

(i) SEQUENCE CHARACTERISTICS:
        (A) LENGTH: 30 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO: 74:

```
GGGGGATCCC AGATCGGACT TATTGGAGGC                                      30
```

(2) INFORMATION FOR SEQ ID NO: 75:

(i) SEQUENCE CHARACTERISTICS:
        (A) LENGTH: 27 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO: 75:

```
GGGGGATCCG GAGGCCAGGG CAACGGA                                         27
```

(2) INFORMATION FOR SEQ ID NO: 76:

(i) SEQUENCE CHARACTERISTICS:
        (A) LENGTH: 27 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO: 76:

```
GGGGGATCCA ACGGAGTGCC ACCTCCC                                         27
```

(2) INFORMATION FOR SEQ ID NO: 77:

(i) SEQUENCE CHARACTERISTICS:
        (A) LENGTH: 31 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO: 77:

```
GGGGGAATTC GAGGAGCTGT CTGGGAGGTG G                                    31
```

(2) INFORMATION FOR SEQ ID NO: 78:

(i) SEQUENCE CHARACTERISTICS:
        (A) LENGTH: 31 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO: 78:

GGGGGAATTC AGGTGGCACT CCGTTGCCCT G                                31

(2) INFORMATION FOR SEQ ID NO: 79:

(i) SEQUENCE CHARACTERISTICS:
        (A) LENGTH: 31 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO: 79:

GGGGGAATTC GCCCTGGCCT CCAACAAGTC C                                31

(2) INFORMATION FOR SEQ ID NO: 80:

(i) SEQUENCE CHARACTERISTICS:
        (A) LENGTH: 30 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO: 80:

GGGGGAATTC GAGGGAAACC ATGAGGAGCC                                  30

(2) INFORMATION FOR SEQ ID NO: 81:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO: 81:

GGACTTGTTG GAGGCCAGGG C                                           21

(2) INFORMATION FOR SEQ ID NO: 82:

(i) SEQUENCE CHARACTERISTICS:
        (A) LENGTH: 30 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO: 82:

GGGGGAATTC ATCAAACCCT GGGGGCACTT                                  30

(2) INFORMATION FOR SEQ ID NO: 83:

(i) SEQUENCE CHARACTERISTICS:
        (A) LENGTH: 29 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO: 83:

GGGGGATCCA AGTGCCCCCA GGGTTTGAT                                   29

(2) INFORMATION FOR SEQ ID NO: 84:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO: 84:

```
CACGGGGATA TCCTTATACC                                            20
```

(2) INFORMATION FOR SEQ ID NO: 85:

(i) SEQUENCE CHARACTERISTICS:
        (A) LENGTH: 18 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO: 85:

```
GTACAACGAT GACACCAG                                              18
```

(2) INFORMATION FOR SEQ ID NO: 86:

(i) SEQUENCE CHARACTERISTICS:
        (A) LENGTH: 16 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO: 86:

```
TGTCCCCGA GCCTAT                                                 16
```

(2) INFORMATION FOR SEQ ID NO: 87:

(i) SEQUENCE CHARACTERISTICS:
        (A) LENGTH: 18 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO: 87:

```
TCCATCTGCT GACCGTGG                                              18
```

(2) INFORMATION FOR SEQ ID NO: 88:

(i) SEQUENCE CHARACTERISTICS:
        (A) LENGTH: 38 amino acids
        (B) TYPE: amino acid
        (D) TOPOLOGY: linear (ii) MOLECULE TYPE: peptide (v) FRAGMENT TYPE: internal (xi) SEQUENCE DESCRIPTION: SEQ ID NO: 88:

```
Glu Gly Asn His Glu Glu Pro Gln Gly Gly Leu Glu Glu Leu Ser Gly
 1               5                  10                  15

Arg Trp His Ser Val Ala Leu Ala Ser Xaa Lys Ser Asp Leu Ile Xaa
            20                  25                  30
```

```
Pro Trp Gly His Phe Arg
            35

(2) INFORMATION FOR SEQ ID NO: 89:

(i) SEQUENCE CHARACTERISTICS:
        (A) LENGTH: 182 amino acids
        (B) TYPE: amino acid
        (D) TOPOLOGY: linear (ii) MOLECULE TYPE: peptide (v) FRAGMENT TYPE: internal (xi) SEQUENCE DESCRIPTION: SEQ ID NO: 89:

Met Lys Leu Ile Leu Leu Leu Cys Leu Gly Leu Ile Leu Val Cys
1               5                   10                  15

Glx Gly His Ala Glu Glu Ala Asn Ser Glu Arg Gly Asn Leu Asp Val
            20                  25                  30

Asp Lys Leu Asn Gly Asp Trp Phe Ser Ile Val Val Ala Ser Asn Lys
            35                  40                  45

Arg Glu Lys Ile Glu Glu Asn Gly Ser Met Arg Val Phe Met Gln His
        50                  55                  60

Ile Asp Val Leu Glu Asn Ser Leu Gly Phe Lys Leu Cys Ile Lys Glu
65                  70                  75                  80

Asn Gly Glu Cys Arg Lys Leu Tyr Ser Val Ala Tyr Lys Thr Pro Lys
                85                  90                  95

Ile Gly Glu Tyr Phe Leu Glu Tyr Asp Gly Gly Asn Thr Phe Thr Ile
                100                 105                 110

Leu Lys Thr Asp Tyr Glu Arg Tyr Val Met Phe His Leu Val Asn Val
            115                 120                 125

Asn Asn Gly Glu Ala Phe Gln Leu Met Glu Leu Tyr Gly Arg Thr Lys
    130                 135                 140

Asp Leu Ser Ser Asp Ile Lys Glu Lys Phe Ala Lys Leu Cys Glu Ala
145                 150                 155                 160

His Gly Ile Thr Arg Asp Asn Ile Ile Asp Leu Thr Lys Thr Asp Arg
                165                 170                 175

Cys Leu Gln Ala Arg Gly
            180

(2) INFORMATION FOR SEQ ID NO: 90:

(i) SEQUENCE CHARACTERISTICS:
        (A) LENGTH: 182 amino acids
        (B) TYPE: amino acid
        (D) TOPOLOGY: linear (ii) MOLECULE TYPE: peptide (v) FRAGMENT TYPE: internal (xi) SEQUENCE DESCRIPTION: SEQ ID NO: 90:

Met Lys Glx Met Leu Leu Leu Cys Leu Gly Leu Ile Leu Val Cys
1               5                   10                  15

Glx Val His Ala Glu Glu Ala Ser Ser Thr Gly Arg Asn Phe Asn Val
            20                  25                  30

Glu Lys Ile Asn Gly Glu Trp His Thr Ile Ile Leu Ala Ser Cys Lys
            35                  40                  45

Arg Glu Lys Ile Glu Asp Asn Gly Asn Phe Arg Leu Phe Leu Glu Gln
        50                  55                  60
```

```
Ile His Val Leu Glu Asn Ser Leu Val Leu Lys Phe His Thr Val Arg
 65                  70                  75                  80

Asp Glu Glu Cys Ser Glu Leu Ser Met Val Ala Asp Lys Thr Glu Lys
                 85                  90                  95

Ala Gly Glu Tyr Ser Val Thr Tyr Asp Gly Phe Asn Thr Phe Thr Ile
                100                 105                 110

Pro Lys Thr Asp Tyr Asp Asn Phe Leu Met Ala His Leu Ile Asn Glu
                115                 120                 125

Lys Asp Gly Glu Thr Phe Gln Leu Met Gly Leu Tyr Gly Arg Glu Pro
130                 135                 140

Asp Leu Met Ser Asp Ile Lys Glu Arg Phe Ala Gln Leu Cys Glu Glu
145                 150                 155                 160

His Gly Ile Leu Arg Glu Asn Ile Ile Asp Leu Ser Asn Ala Asn Arg
                165                 170                 175

Cys Leu Gln Ala Arg Glu
                180
```

(2) INFORMATION FOR SEQ ID NO: 91:

(i) SEQUENCE CHARACTERISTICS:
        (A) LENGTH: 24 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO: 91:

GGGAATTCAA TCCATCGAAG GAAG                                24

(2) INFORMATION FOR SEQ ID NO: 92:

(i) SEQUENCE CHARACTERISTICS:
        (A) LENGTH: 24 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO: 92:

GGGAATTCAA TCGATCGAAG GAAG                                24

(2) INFORMATION FOR SEQ ID NO: 93:

(i) SEQUENCE CHARACTERISTICS:
        (A) LENGTH: 29 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO: 93:

CGTACGGAAA GATGCTGACC CCAGATCGG                            29

(2) INFORMATION FOR SEQ ID NO: 94:

(i) SEQUENCE CHARACTERISTICS:
        (A) LENGTH: 27 base pairs
        (B) TYPE: nucleic acid
        (C) STRANDEDNESS: single
        (D) TOPOLOGY: linear

```
        (ii) MOLECULE TYPE: cDNA (xi) SEQUENCE DESCRIPTION: SEQ ID NO: 94:

CTCTGAAAGA TGCTGACCCC AGATCGG                                      27

(2) INFORMATION FOR SEQ ID NO: 95:

(i) SEQUENCE CHARACTERISTICS:
            (A) LENGTH: 20 base pairs
            (B) TYPE: nucleic acid
            (C) STRANDEDNESS: single
            (D) TOPOLOGY: linear (ii) MOLECULE TYPE: cDNA (xi) SEQUENCE DESCRIPTION: SEQ ID NO: 95:

GGGTCTAGAG GTACCGTCCG                                              20

(2) INFORMATION FOR SEQ ID NO: 96:

(i) SEQUENCE CHARACTERISTICS:
            (A) LENGTH: 33 base pairs
            (B) TYPE: nucleic acid
            (C) STRANDEDNESS: single
            (D) TOPOLOGY: linear (ii) MOLECULE TYPE: cDNA (xi) SEQUENCE DESCRIPTION: SEQ ID NO: 96:

GGGTCTAGAG GTACCGTCCG ATCGTCGATC ATT                               33

(2) INFORMATION FOR SEQ ID NO: 97:

(i) SEQUENCE CHARACTERISTICS:
            (A) LENGTH: 13 amino acids
            (B) TYPE: amino acid
            (D) TOPOLOGY: linear (ii) MOLECULE TYPE: peptide (v) FRAGMENT TYPE: internal (xi) SEQUENCE DESCRIPTION: SEQ ID NO: 97:

Gly Arg Trp His Ser Val Ala Leu Ala Ser Lys Ser Asp
1               5                   10

(2) INFORMATION FOR SEQ ID NO: 98:

(i) SEQUENCE CHARACTERISTICS:
            (A) LENGTH: 47 base pairs
            (B) TYPE: nucleic acid
            (C) STRANDEDNESS: single
            (D) TOPOLOGY: linear (ii) MOLECULE TYPE: cDNA (xi) SEQUENCE DESCRIPTION: SEQ ID NO: 98:

ATCTGTGGCC TCCAGGCTCA GGAGGGAAAC CATGAGGAGC CCCAGGG                47

(2) INFORMATION FOR SEQ ID NO: 99:

(i) SEQUENCE CHARACTERISTICS:
            (A) LENGTH: 45 base pairs
            (B) TYPE: nucleic acid
            (C) STRANDEDNESS: single
            (D) TOPOLOGY: linear (ii) MOLECULE TYPE: cDNA
```

(xi) SEQUENCE DESCRIPTION: SEQ ID NO: 99:

AAACCCTGGG GGCACTTCAG GGTTTTCATC CACAGCATGA GCGCA         45

(2) INFORMATION FOR SEQ ID NO: 100:

(i) SEQUENCE CHARACTERISTICS:
        (A) LENGTH: 35 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO: 100:

GGGCTCGAGG TCGAGTTTTT TTTTTTTTTT TTGAC         35

(2) INFORMATION FOR SEQ ID NO: 101:

(i) SEQUENCE CHARACTERISTICS:
        (A) LENGTH: 12 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO: 101:

CCGGAATTCC GG         12

(2) INFORMATION FOR SEQ ID NO: 102:

(i) SEQUENCE CHARACTERISTICS:
        (A) LENGTH: 13 base pairs
        (B) TYPE: nucleic acid
        (C) STRANDEDNESS: single
        (D) TOPOLOGY: linear (ii) MOLECULE TYPE: cDNA (iv) ANTI-SENSE: yes (xi) SEQUENCE DESCRIPTION: SEQ ID NO: 102:

AATGATCGAT GCT         13

(2) INFORMATION FOR SEQ ID NO: 103:

(i) SEQUENCE CHARACTERISTICS:
        (A) LENGTH: 27 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO: 103:

GGGGGATCCC TAGTCTCTGG AACCCTG         27

(2) INFORMATION FOR SEQ ID NO: 104:

(i) SEQUENCE CHARACTERISTICS:
        (A) LENGTH: 27 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO: 104:

```
GGGGAATTCG AGGGAAACCA TGAGGAG                                              27
```

(2) INFORMATION FOR SEQ ID NO: 105:

(i) SEQUENCE CHARACTERISTICS:
        (A) LENGTH: 65 amino acids
        (B) TYPE: amino acid
        (D) TOPOLOGY: linear (ii) MOLECULE TYPE: peptide (v) FRAGMENT TYPE: internal (xi) SEQUENCE DESCRIPTION: SEQ ID NO: 105:

```
Asp Thr Val Ala Val Ser Gly Lys Trp Tyr Leu Lys Ala Met Thr Ala
 1               5                  10                  15

Asp Gln Glu Val Pro Glu Lys Pro Asp Ser Val Thr Pro Met Ile Leu
                20                  25                  30

Lys Ala Gln Lys Gly Gly Asn Leu Glu Ala Lys Ile Thr Met Leu Thr
            35                  40                  45

Asn Gly Gln Cys Gln Asn Ile Thr Val Val Leu His Lys Thr Ser Glu
        50                  55                  60

Pro
 65
```

(2) INFORMATION FOR SEQ ID NO: 106:

(i) SEQUENCE CHARACTERISTICS:
        (A) LENGTH: 53 amino acids
        (B) TYPE: amino acid
        (D) TOPOLOGY: linear (ii) MOLECULE TYPE: peptide (v) FRAGMENT TYPE: internal (xi) SEQUENCE DESCRIPTION: SEQ ID NO: 106:

```
Thr Val Val Leu His Lys Thr Ser Glu Pro Gly Lys Tyr Thr Ala Tyr
 1               5                  10                  15

Glu Gly Gln Arg Val Val Phe Ile Gln Pro Ser Pro Val Arg Asp His
                20                  25                  30

Tyr Ile Leu Tyr Cys Glu Gly Glu Leu His Gly Arg Gln Ile Arg Met
            35                  40                  45

Ala Lys Leu Leu Gly
        50
```

(2) INFORMATION FOR SEQ ID NO: 107:

(i) SEQUENCE CHARACTERISTICS:
        (A) LENGTH: 60 amino acids
        (B) TYPE: amino acid
        (D) TOPOLOGY: linear (ii) MOLECULE TYPE: peptide (v) FRAGMENT TYPE: internal (xi) SEQUENCE DESCRIPTION: SEQ ID NO: 107:

```
Leu Tyr Cys Glu Gly Glu Leu His Gly Arg Gln Ile Arg Met Ala Lys
 1               5                  10                  15

Leu Leu Gly Arg Asp Pro Glu Gln Ser Gln Glu Ala Leu Glu Asp Phe
                20                  25                  30

Arg Glu Phe Ser Arg Ala Lys Gly Leu Asn Gln Glu Ile Leu Glu Leu
            35                  40                  45
```

-continued

```
Ala Gln Ser Glu Thr Cys Ser Pro Gly Gly Gln Xaa
    50                  55                  60
```

(2) INFORMATION FOR SEQ ID NO: 108:

(i) SEQUENCE CHARACTERISTICS:
        (A) LENGTH: 13 amino acids
        (B) TYPE: amino acid
        (D) TOPOLOGY: linear (ii) MOLECULE TYPE: peptide (v) FRAGMENT TYPE: internal (xi) SEQUENCE DESCRIPTION: SEQ ID NO: 108:

```
Gly Lys Trp Tyr Leu Lys Ala Met Thr Ala Asp Gln Glu
 1               5                   10
```

(2) INFORMATION FOR SEQ ID NO: 109:

(i) SEQUENCE CHARACTERISTICS:
        (A) LENGTH: 13 amino acids
        (B) TYPE: amino acid
        (D) TOPOLOGY: linear (ii) MOLECULE TYPE: peptide (v) FRAGMENT TYPE: internal (xi) SEQUENCE DESCRIPTION: SEQ ID NO: 109:

```
Ala Lys Ile Thr Met Leu Thr Asn Gly Gln Cys Gln Asn
 1               5                   10
```